(12) United States Patent
Skubitz et al.

(10) Patent No.: US 12,303,682 B2
(45) Date of Patent: May 20, 2025

(54) MEDICAL LEAD WITH SEGMENTED ELECTRODES

(71) Applicant: Medtronic, Inc., Minneapolis, MN (US)

(72) Inventors: Sean P. Skubitz, Forest Lake, MN (US); Jacob Silverberg, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 160 days.

(21) Appl. No.: 17/208,645

(22) Filed: Mar. 22, 2021

(65) Prior Publication Data

US 2021/0205612 A1 Jul. 8, 2021

Related U.S. Application Data

(63) Continuation of application No. 16/030,334, filed on Jul. 9, 2018, now Pat. No. 10,953,221.

(Continued)

(51) Int. Cl.
*A61N 1/375* (2006.01)
*A61N 1/05* (2006.01)
(Continued)

(52) U.S. Cl.
CPC .............. *A61N 1/05* (2013.01); *A61N 1/0534* (2013.01); *H01R 24/58* (2013.01);
(Continued)

(58) Field of Classification Search
CPC ....................................................... A61N 1/05
See application file for complete search history.

(56) References Cited

U.S. PATENT DOCUMENTS 5,385,578 A 1/1995 Bush et al.
8,788,063 B2 7/2014 Chen
(Continued)

FOREIGN PATENT DOCUMENTS

CN 102665818 A 9/2012
CN 103002947 A 3/2013
(Continued)

OTHER PUBLICATIONS

Notice of Allowance from U.S. Appl. No. 16/039,811 dated Jun. 11, 2021 (8 pp).

(Continued)

*Primary Examiner* — Michael J D'Abreu
(74) *Attorney, Agent, or Firm* — Shumaker & Sieffert, P.A.

(57) ABSTRACT

A medical lead system includes a lead body, a plurality of electrical conductors, and a plurality of electrodes. The lead body may include a distal end and a proximal end defining a longitudinal axis of the lead body. The plurality of electrical conductors extending about the longitudinal axis of the lead body. The plurality of electrodes is positioned around an outer perimeter of the lead body. An inner surface of each of the plurality of electrodes defines an inner perimeter. Each respective electrode of the plurality of electrodes is electrically coupled to a respective electrical conductor of the plurality of electrical conductors. Each electrode of the plurality of electrodes includes at least one electrode locking feature extending into the lead body from the inner perimeter.

20 Claims, 26 Drawing Sheets

Related U.S. Application Data

(60) Provisional application No. 62/552,139, filed on Aug. 30, 2017.

(51) Int. Cl.
| | |
|---|---|
| *H01R 24/58* | (2011.01) |
| *A61N 1/36* | (2006.01) |
| *A61N 1/372* | (2006.01) |
| *B29C 45/14* | (2006.01) |
| *B29K 75/00* | (2006.01) |
| *B29L 31/00* | (2006.01) |
| *H01R 24/86* | (2011.01) |

(52) U.S. Cl.
CPC ...... *A61N 1/36182* (2013.01); *A61N 1/37217* (2013.01); *B29C 45/14639* (2013.01); *B29K 2075/00* (2013.01); *B29K 2995/0056* (2013.01); *B29L 2031/753* (2013.01); *H01R 24/86* (2013.01); *H01R 2201/12* (2013.01)

(56) References Cited

U.S. PATENT DOCUMENTS

| | | | |
|---|---|---|---|
| 8,862,242 B2 | 10/2014 | Pianca | |
| 8,887,387 B2 | 11/2014 | Pianca | |
| 9,248,272 B2 | 2/2016 | Romero | |
| 9,270,070 B2 | 2/2016 | Pianca | |
| 9,295,830 B2 | 3/2016 | Pianca | |
| 9,381,348 B2 | 7/2016 | Romero et al. | |
| 9,498,620 B2 | 11/2016 | Romero et al. | |
| 10,953,221 B2 | 3/2021 | Skubitz et al. | |
| 2006/0089691 A1 | 4/2006 | Kaplan et al. | |
| 2006/0173262 A1* | 8/2006 | Hegland | A61N 1/0551 |
| | | | 600/373 |
| 2010/0094387 A1 | 4/2010 | Pianca et al. | |
| 2010/0269338 A1* | 10/2010 | Dye | A61N 1/0534 |
| | | | 29/874 |
| 2011/0030817 A1 | 6/2011 | Chen | |
| 2011/0130818 A1 | 6/2011 | Chen | |
| 2012/0005896 A1 | 1/2012 | Dye et al. | |
| 2012/0197375 A1* | 8/2012 | Pianca | A61N 1/0534 |
| | | | 607/148 |
| 2012/0203320 A1 | 8/2012 | Digiore et al. | |
| 2014/0309719 A1 | 10/2014 | Oster et al. | |
| 2015/0066120 A1 | 3/2015 | Govea | |
| 2015/0142090 A1* | 5/2015 | Duijsens | A61N 1/05 |
| | | | 607/116 |
| 2016/0030731 A1 | 2/2016 | Finley et al. | |
| 2016/0144165 A1 | 5/2016 | Young et al. | |
| 2016/0228692 A1 | 8/2016 | Steinke et al. | |
| 2019/0060634 A1 | 2/2019 | Skubitz et al. | |
| 2022/0016414 A1 | 1/2022 | Skubitz et al. | |

FOREIGN PATENT DOCUMENTS

| | | |
|---|---|---|
| CN | 105263566 A | 1/2016 |
| CN | 105263568 A | 1/2016 |
| EP | 2056926 A1 | 5/2009 |
| WO | 2008/024526 A1 | 2/2008 |

OTHER PUBLICATIONS

Extended Search Report from counterpart European Application No. 21203253.6 dated Jan. 17, 2022, 8 pp.
Invitation to Pay Additional Fees from International Application No. PCT/US2018/042689, dated Oct. 8, 2018, 11 pp.
Notification Concerning Transmittal of International Preliminary Report on Patentability, dated Mar. 12, 2020, from International Application No. PCT/US2018/042689, filed Jul. 18, 2018, 10 pages.
Search Report from counterpart European Application No. PCT/US2018/042689, dated Jan. 2, 2019, 18 pp.
Prosecution History from U.S. Appl. No. 16/039,811, dated Feb. 14, 2020 through Feb. 3, 2021, 63 pp.
Prosecution History from U.S. Appl. No. 16/030,334, dated Feb. 14, 2020 through Dec. 24, 2020, 37 pp.
First Office Action and Search Report, and translation thereof, from counterpart Chinese Application No. 201810924851.3 dated Dec. 29, 2022, 15 pp.
First Office Action and Search Report, and translation thereof, from counterpart Chinese Application No. 201810922456.1 dated Dec. 26, 2022, 18 pp.
First Office Action and Search Report, and translation thereof, from counterpart Chinese Application No. 201810924568.0 dated Dec. 29, 2022, 18 pp.
Office Action from U.S. Appl. No. 17/492,110 dated Dec. 22, 2023, 11 pp.
Final Office Action from U.S. Appl. No. 17/492,110 dated Jul. 12, 2024, 12 pp.
Communication pursuant to Article 94(3) EPC from counterpart European Application No. 21203253.6 dated Jul. 6, 2023, 3 pp.
Second Office Action and Search Report, and translation thereof, from counterpart Chinese Application No. 201810922456.1 dated Jul. 20, 2023, 11 pp.
Response to Office Action dated Dec. 22, 2023 from U.S. Appl. No. 17/492,110 filed Mar. 22, 2024, 10 pp.
Final Office Action from U.S. Appl. No. 17/492,110 dated Oct. 21, 2024, 12 pp.
Response to Final Office Action dated Jul. 12, 2024 from U.S. Appl. No. 17/492,110, filed Sep. 12, 2024, 6 pp.
Response to Final Office Action dated Oct. 21, 2024 from U.S. Appl. No. 17/492,110 filed Dec. 13, 2024, 10 pp.
Notice of Allowance from U.S. Appl. No. 17/492,110 dated Feb. 12, 2025, 7 pp.

* cited by examiner

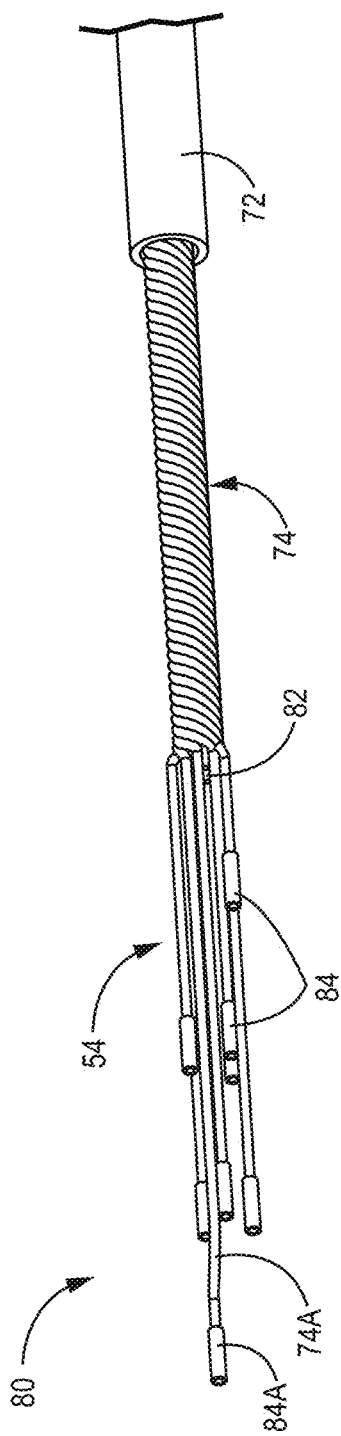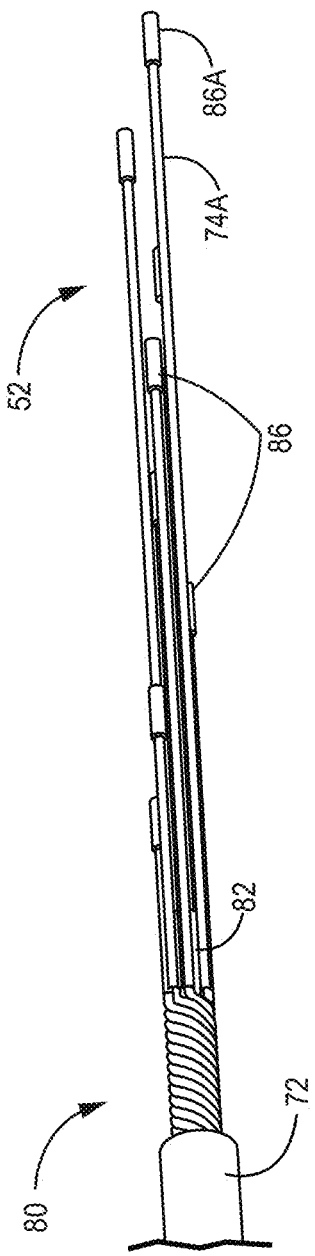
FIG. 4A
FIG. 4B

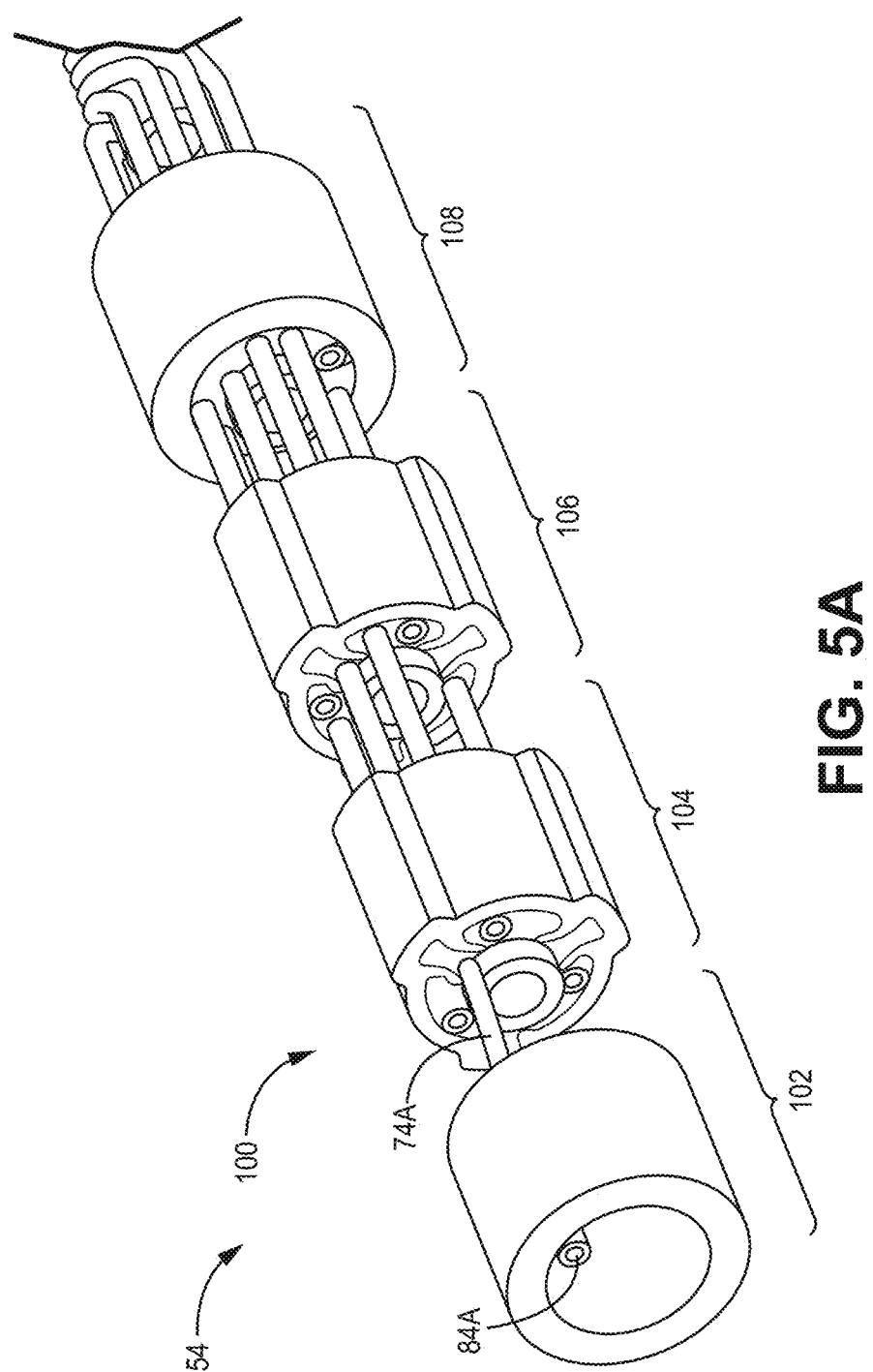

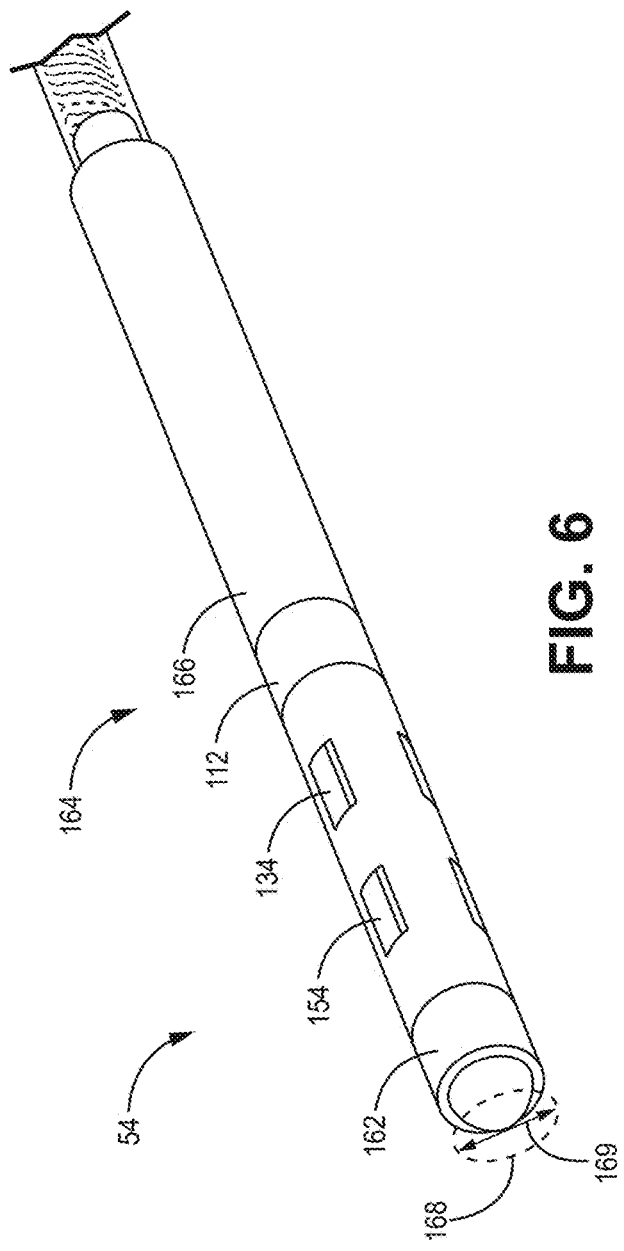
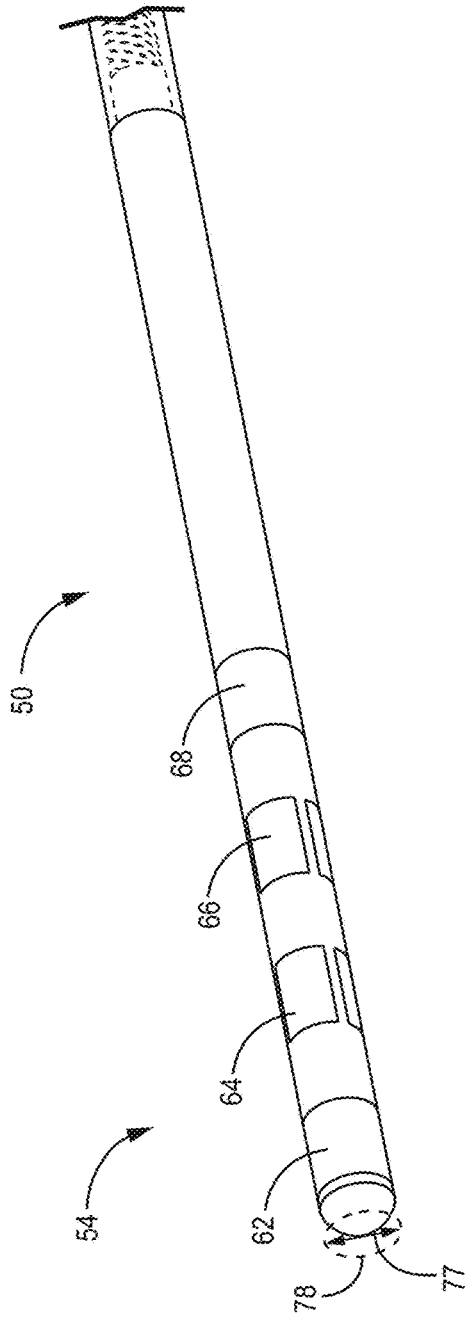
FIG. 6
FIG. 7

MEDICAL LEAD WITH SEGMENTED ELECTRODES

This application is a continuation of U.S. patent application Ser. No. 16/030,334, filed Jul. 9, 2018, which claims the benefit of U.S. Provisional Application No. 62/552,139 filed Aug. 30, 2017, both of which are incorporated herein by reference in their entirety.

TECHNICAL FIELD

This disclosure relates to medical device systems including one or more leads.

BACKGROUND

Medical devices may be used to deliver therapy to a patient to treat symptoms or conditions such as chronic pain, seizure disorders (e.g., epilepsy), heart arrhythmias (e.g., fibrillation), tremor, Parkinson's disease, other types of movement disorders, obesity, mood disorders, urinary or fecal incontinence, or other types of symptoms or conditions. The therapy may be electrical stimulation therapy. Medical devices, such as implantable medical devices (IMDs), may be used for therapies such as deep brain stimulation (DBS), spinal cord stimulation (SC S), sacral neuromodulation, pelvic stimulation, gastric stimulation, peripheral nerve stimulation, cardiac stimulation, functional electrical stimulation, or other types of stimulation.

A medical device may include one or more leads carrying one or more electrodes. The medical device may deliver the electrical stimulation therapy to one or more target tissue sites within the patient and/or sense one or more electrical signals via the lead.

SUMMARY

In some examples, a medical lead may be formed from preformed electrode and terminal segments, or "electrode preforms" and "terminal preforms". The electrode and terminal preforms may be electrically conductive rings filled with an insulator that includes channels. The preforms may be configured for placement onto a conductor assembly. Each conductor of the conductor assembly may be fitted into a channel of one or more preforms. The conductive ring of each preform may be coupled to one or more conductors. Each preform may be a rigid and precisely fabricated structure that allows for stable and accurate assembly of the medical lead.

For electrode preforms that are coupled to more than one conductor, the conductive ring may be segmented to form separate electrodes, where each segmented electrode couples to a single conductor. This segmentation may be achieved by designing the electrode preform to have a larger perimeter than a final outer perimeter of the medical lead. Portions of the electrode preform outside the outer perimeter may be removed during manufacture, resulting in segmented portions of the conductive ring that act as electrodes.

The electrode preforms may also include other features. Electrode preforms may include electrode locking features extending into the insulator, such that the electrode locking features secure the segmented electrodes into the medical lead after segmentation. Electrode preforms may also include electrode portions having curved perimeters along a circumferential plane of the medical lead that form curved electrode perimeters in the final medical lead. These curved perimeters may operate with reduced current density along edges.

In some examples, the disclosure describes an assembly for forming a medical lead. The assembly includes at least one electrode preform. The at least one electrode preform includes an electrically conductive ring and an insulator portion within the electrically conductive ring. The insulator portion includes at least one connection channel and at least a portion of the at least one connection channel is bounded by the electrically conductive ring.

In some examples of the assembly described above, the at least one electrode preform is a ring electrode preform and the electrically conductive ring includes at least one raised portion extending around a perimeter of the ring and at least one electrode portion.

In some examples of the assembly described above, the at least one electrode preform is a segmented electrode preform and the electrically conductive ring includes a plurality of electrode portions and a plurality of raised portions. The at least one electrode preform is configured such that respective electrode portions alternate with respective raised portions continuously around the ring. Each of the plurality of electrode portions is continuous at a radius from a center of the electrically conductive ring that corresponds to an outer perimeter of the medical lead. The insulator portion has a plurality of projections extending into a respective raised portion of the ring radially outward of the radius from the center of the conductive ring that corresponds to the outer perimeter of the medical lead. The at least one connection channel includes a respective connection channel for each of the plurality of electrode portions.

In some examples of the assembly described above, the assembly further includes a lead body and a plurality of electrical conductors. The lead body includes a distal end and a proximal end defining a longitudinal axis of the lead body. The plurality of electrical conductors extends about the longitudinal axis of the lead body. The at least one segmented electrode preform includes an electrically conductive ring and an insulator portion. Each respective electrode portion of the plurality of electrode portions is electrically coupled to a respective electrical conductor of the plurality of electrical conductors through a connection channel of the at least one connection channel.

In some examples, the disclosure describes a medical lead system that includes a lead body, a plurality of electrical conductors, and a plurality of electrodes. The lead body includes a distal end and a proximal end defining a longitudinal axis of the lead body. The plurality of electrical conductors extending about the longitudinal axis of the lead body. The plurality of electrodes positioned around an outer perimeter of the lead body the outer perimeter defining a circumferential plane. Each respective electrode of the plurality of electrodes is electrically coupled to a respective electrical conductor of the plurality of electrical conductors. Each electrode of the plurality of electrodes has a circumferential perimeter that includes a curved portion having a radius of a curve of the curved portion.

In some examples, the disclosure describes a medical lead system that includes a lead body, a plurality of electrical conductors, and a plurality of electrodes. The lead body includes a distal end and a proximal end defining a longitudinal axis of the lead body. The plurality of electrical conductors extending about the longitudinal axis of the lead body, each electrical conductor having a conductor body and a distal connection portion. The plurality of electrodes positioned around an outer perimeter of the distal end of the lead body. Each respective electrode of the plurality of electrodes is electrically coupled to the distal connection portion of a respective electrical conductor of the plurality of electrical conductors. The lead body includes a plurality of conductor channels and a plurality of connector channels. The conductor body of each electrical conductor extends through at least one conductor channel of the plurality of conductor channels and the distal connection portion of each electrical conductor is positioned in a connection channel of the plurality of connection channels. A diameter of the conductor channel is greater than or equal to a diameter of the connection channel of a respective electrical conductor of the plurality of electrical conductors.

In some examples, the disclosure describes a medical lead system that includes a lead body, a plurality of electrical conductors, and a plurality of electrodes. The lead body may include a distal end and a proximal end defining a longitudinal axis of the lead body. The plurality of electrical conductors extending about the longitudinal axis of the lead body. The plurality of electrodes is positioned around an outer perimeter of the lead body. An inner surface of each of the plurality of electrodes defines an inner perimeter. Each respective electrode of the plurality of electrodes is electrically coupled to a respective electrical conductor of the plurality of electrical conductors. Each electrode of the plurality of electrodes includes at least one electrode locking feature extending into the lead body from the inner perimeter.

In some examples, the disclosure describes an assembly for forming a medical lead. The assembly includes a lead body, the plurality of electrical conductors, and at least one ring electrode preform. The lead body including a distal end and a proximal end defining a longitudinal axis of the lead body. The plurality of electrical conductors extends about the longitudinal axis of the lead body. The at least one ring electrode preform includes an electrically conductive ring and an insulator portion. The electrically conductive ring includes at least one raised portion extending around a perimeter of the ring and at least one electrode portion. The insulator portion is within the electrically conductive ring. The at least one electrode portion is electrically coupled to a respective electrical conductor of the plurality of electrical conductors.

In some examples, the disclosure describes a method of making a medical lead. The method includes providing an assembly that includes a lead body and a plurality of electrical conductors. The lead body includes a distal end and a proximal end defining a longitudinal axis of the lead body. The plurality of electrical conductors extending about the longitudinal axis of the lead body, each electrical conductor having a conductor body and a distal connection sleeve. The method further includes positioning at least one segmented electrode preform around at least a portion of the plurality of electrical conductors at the distal end. The segmented electrode preform includes an electrically conductive ring and an insulator portion within the electrically conductive ring. The ring is configured such that respective electrode portions alternate with respective raised portions continuously around the ring. Each of the plurality of electrode portions is continuous at a radius from the longitudinal axis corresponding to an outer perimeter of the medical lead. The insulator portion has a plurality of projections each extending into a respective raised portion of the ring beyond the radius from the longitudinal axis corresponding to the outer perimeter of the medical lead. The insulator portion includes at least one channel. The method further includes electrically coupling an electrode portion of the segmented electrode preform to the distal connection sleeve of a corresponding electrical conductor. The method further includes forming an overmold on at least the segmented electrode preform and grinding the segmented electrode preform to the outer perimeter.

In some examples, the disclosure describes a method of making a preformed segment for a medical lead. The method includes forming an electrically conductive ring and forming an insulator portion within the electrically conductive ring. The insulator portion includes a plurality of channels, wherein at least a portion of each channel of the plurality of channels is bounded by the electrically conductive ring.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIG. 4A is a conceptual diagram illustrating a distal end of an example conductor preassembly for a medical lead.

FIG. 4B is a conceptual diagram illustrating a proximal end of an example conductor preassembly for a medical lead.

FIG. 5A is a conceptual diagram illustrating a distal portion of an example preform preassembly for a medical lead.

FIG. 6 is a conceptual diagram illustrating a pre-grind distal end preassembly for a medical lead.

FIG. 7 is a conceptual diagram illustrating a distal end of a lead.

DETAILED DESCRIPTION

As described above, some examples of the disclosure relate to medical device leads (also referred to as "lead systems," "medical leads," or "leads") including one or more electrodes. Using the lead and electrode, a medical device may deliver or sense electrical signals to provide therapy to a patient to treat a patient condition. Medical leads may include a conductive electrode member electrically and mechanically connected to one or more conductive lead wires (also may be referred to as "conductors") extending through the lead body. Electrical stimulation from a medical device may be conductive along the lead wire to be delivered across the electrode surface.

In some instances, a medical lead manufacturing process may involve forming a pre-electrode assembly that includes a lead body and electrical conductors extending through the lead body. Electrodes may be fitted around the pre-electrode assembly and coupled to the electrical conductors to form a medical lead. Due to this superficial placement of electrodes on a surface of the lead, electrode features may be limited to the surface of the lead, and the electrodes may not be securely attached to the lead body.

According to principles of the disclosure, electrodes and/or terminals of a medical lead may be formed using pre-formed segments. A preformed segment may include a conductive ring and an insulator portion in the conductive ring. The conductive ring may act as one or more electrodes or terminals, while the insulator portion may act as a conductor hub for connecting conductors to the electrode or terminal and passing through conductors intended for other electrodes or terminals. The conductive ring of a preformed segment may remain intact up to a final processing step to provide support for intermediate assemblies during processing. The preformed segments and conductors may be configured for modular and sequential placement of the preformed segments onto conductor preassemblies. Because the conductive ring is not limited to a surface of the medical lead, the conductive ring may include electrode locking features that extend into the preformed segments and curved electrode edges designed to reduce variations in current density at edges of the electrode. A lead formed from the preformed segments described above may be more durable, more precisely manufactured, and more resistant to current leakage.

In some examples, a medical lead may be formed from preformed segments ("preforms") as follows. Preforms may be positioned on and secured to a conductor preassembly that includes conductors extending through a lead body and thereby form a preform preassembly. The preform preassembly may be covered with an overmold to form a solid pre-grind preassembly. An outside surface of the pre-grind preassembly may be ground down to remove portions of the preforms and expose and/or isolate electrode portions of the preforms and thereby form a medical lead.

Figure 1:
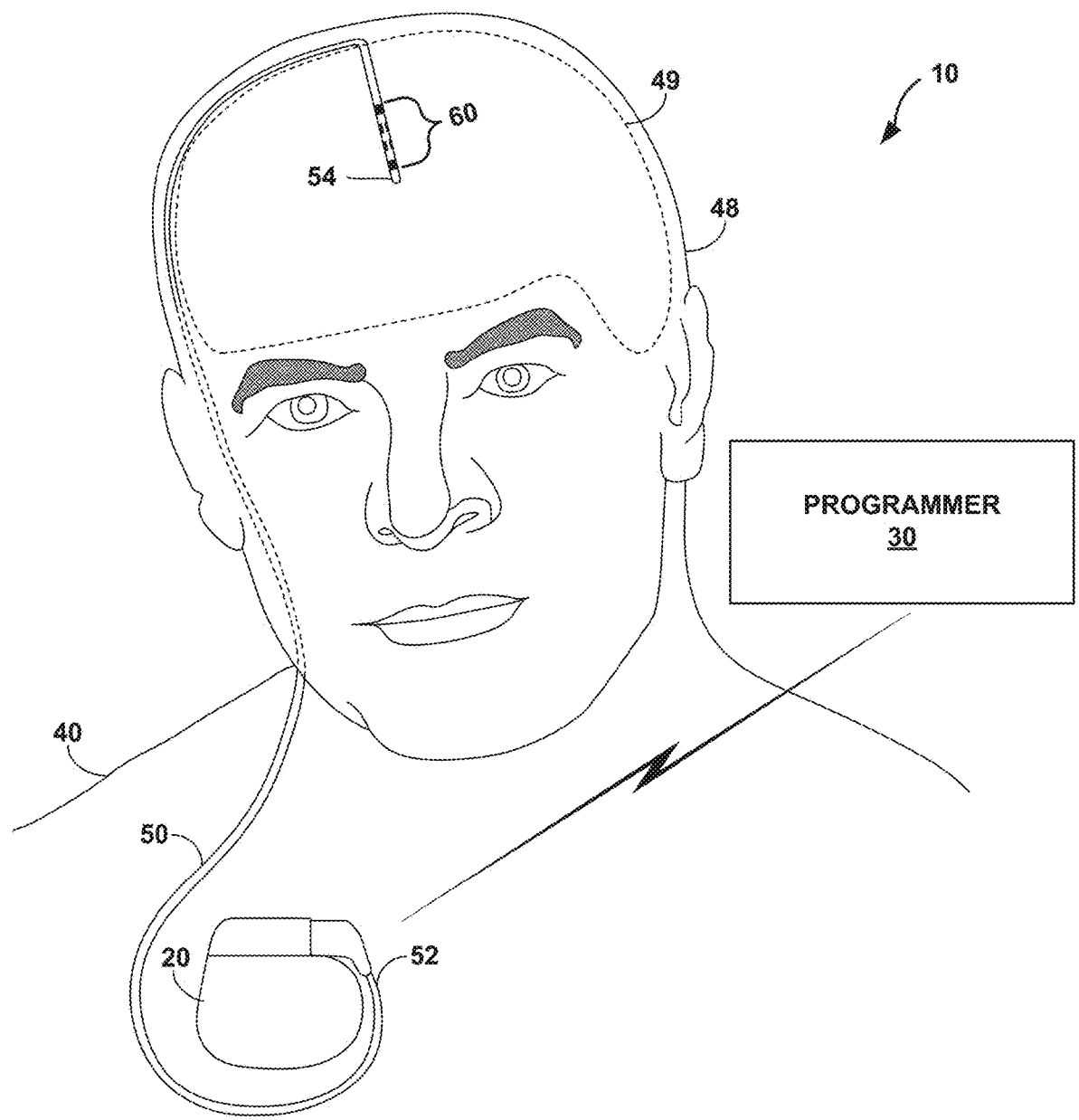
FIG. 1 is a conceptual diagram illustrating an example of a therapy system that delivers electrical stimulation therapy to a patient.

FIG. 1 is a conceptual diagram illustrating an exemplary therapy system 10 including lead 50 implanted in the brain 49 of patient 40. For ease of illustration, examples of the disclosure will primarily be described with regard to implantable electrical stimulation leads and implantable medical devices that apply neurostimulation therapy to brain 49 of patient 40 in the form of deep brain stimulation (DBS). However, the features and techniques described herein may be useful in other types of medical device systems which employ medical leads to deliver electricals stimulation to a patient and/or sense electrical signals via one or more electrodes of the lead. For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient. The medical lead system may be used with human subjects or with non-human subjects.

As shown in FIG. 1, therapy system 10 includes medical device programmer 30, implantable medical device (IMD) 20, and lead 50. Lead 50 includes plurality of electrodes 60 adjacent a distal end 54 of lead 50. IMD 20 includes a stimulation therapy module that includes an electrical stimulation generator that generates and delivers electrical stimulation therapy to one or more regions of brain 49 of patient 40 via one or more of electrodes 60. In the example shown in FIG. 1, therapy system 10 may be referred to as a DBS system because IMD 20 provides electrical stimulation therapy directly to tissue within brain 49, e.g., a tissue site under the dura mater of brain 49. In other examples, one or more of lead 50 may be positioned to deliver therapy to a surface of brain 49 (e.g., the cortical surface of brain 49).

In accordance with examples of the disclosure, lead 50 includes distal end 54 and a proximal end 52. As lead 50 is assembled, respective electrical connection sleeves (not shown in FIG. 1) adjacent proximal end 52 provide an electrical connection between IMD 20 and the conductive pathways of lead 50 running to electrodes 60 adjacent distal end 54 defined by the plurality of conductors of lead 50. Using the conductive pathways, IMD 20 may deliver electrical stimulation to patient 40 and/or sense electric signals of patient 40 using lead 50. While FIG. 1 illustrates proximal end of lead 50 connected directly to the header of IMD 20, in other examples, the proximal end of lead 50 may be connected to one or more lead extensions which are connected to the header of IMD 20 to electrically connect lead 50 to IMD 20.

In the example shown in FIG. 1, IMD 20 may be implanted within a subcutaneous pocket below the clavicle of patient 40. In other examples, IMD 20 may be implanted within other regions of patient 40, such as a subcutaneous pocket in the abdomen or buttocks of patient 40 or proximate the cranium 48 of patient 40. Proximal end 52 of lead 50 is coupled to IMD 20 via a connection sleeve block (also referred to as a header), which may include, for example, electrical contacts that electrically couple to respective electrical contacts at proximal end 52 of lead 50. The electrical contacts electrically couple the electrodes 60 carried by distal end 54 of lead 50. Lead 50 traverses from the implant site of IMD 20 within a chest cavity of patient 40, along the neck of patient 40 and through the cranium of patient 40 to access brain 49. Generally, IMD 20 is constructed of a biocompatible material that resists corrosion and degradation from bodily fluids. IMD 20 may comprise a hermetic housing to substantially enclose components, such as a processor, therapy module, and memory.

Lead 50 may be positioned to deliver electrical stimulation to one or more target tissue sites within brain 49 to manage patient symptoms associated with a disorder of patient 40. Lead 50 may be implanted to position electrodes 60 at desired locations of brain 49 through respective holes in cranium 48. Lead 50 may be placed at any location within brain 49 such that electrodes 60 are capable of providing electrical stimulation to target tissue sites within brain 49 during treatment. Although FIG. 1 illustrates system 10 as including a single lead 50 coupled to IMD 20, in some examples, system 10 may include more than one lead.

Lead 50 may deliver electrical stimulation via electrodes 60 to treat any number of neurological disorders or diseases in addition to movement disorders, such as seizure disorders or psychiatric disorders. Lead 50 may be implanted within a desired location of brain 49 via any suitable technique, such as through respective burr holes in a skull of patient 40 or through a common burr hole in the cranium 48. Lead 50 may be placed at any location within brain 49 such that electrodes 60 of lead 50 are capable of providing electrical stimulation to targeted tissue during treatment. In the examples shown in FIG. 1, electrodes 60 of lead 50 are shown as segmented electrodes and ring electrodes. Electrodes 60 of lead 50 may have a complex electrode array geometry that is capable of producing shaped electrical fields. In this manner, electrical stimulation may be directed to a specific direction from lead 50 to enhance therapy efficacy and reduce possible adverse side effects from stimulating a large volume of tissue.

IMD 20 may deliver electrical stimulation therapy to brain 49 of patient 40 according to one or more stimulation therapy programs. A therapy program may define one or more electrical stimulation parameter values for therapy generated and delivered from IMD 20 to brain 49 of patient 40. Where IMD 20 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 40, therapy system 10 monitors electrical signals, such as, e.g., one or more bioelectrical brain signals of patient 40. For example, IMD 20 may include a sensing module that senses bioelectrical brain signals within one or more regions of brain 49. In the example shown in FIG. 1, the signals generated by electrodes 60 are conducted to the sensing module within IMD 20 via conductors within lead 50, including one or more conductors within lead 50 between distal end 54 and proximal end 52 of lead 50.

Programmer 30 wirelessly communicates with IMD 20 as needed to provide or retrieve therapy information. Programmer 30 is an external computing device that the user, e.g., the clinician and/or patient 40, may use to communicate with IMD 20. For example, programmer 30 may be a clinician programmer that the clinician uses to communicate with IMD 20 and program one or more therapy programs for IMD 20. Alternatively, programmer 30 may be a patient programmer that allows patient 40 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 20.

Programmer 30 may be a hand-held computing device with a display viewable by the user and an interface for providing input to programmer 30 (i.e., a user input mechanism). In other examples, programmer 30 may be a larger workstation or a separate application within another multi-function device, rather than a dedicated computing device. For example, the multi-function device may be a notebook computer, tablet computer, workstation, cellular phone, personal digital assistant, or another computing device that may run an application that enables the computing device to operate as a secure medical device programmer 30.

Again, while lead 50 is described here for use in DBS applications, lead 50 or other leads may be implanted at any other location within patient 40. For example, lead 50 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 40 and adjacent to sensitive nerve tissue. Therapy may also be changed if leads migrate to new locations within the tissue or patient 40 no longer perceives therapeutic effects of the stimulation. The features or techniques of this disclosure may be useful in other types of medical applications.

Figure 2:
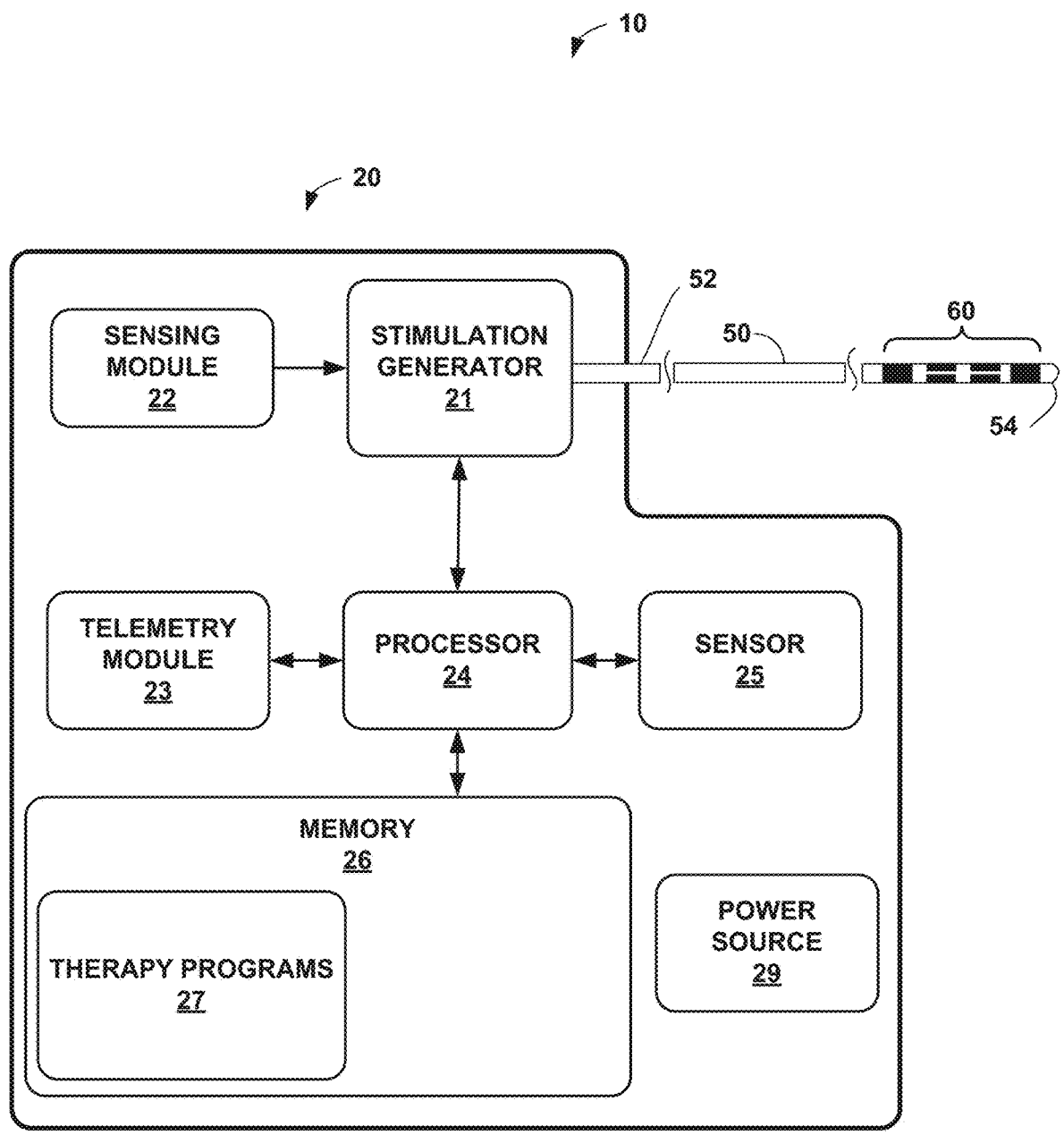
FIG. 2 is a conceptual block diagram of an example of a medical device system.

FIG. 2 is a functional block diagram illustrating components of IMD 20. As shown, therapy system 10 includes IMD 20 coupled to lead 50. In the example of FIG. 2, IMD 20 includes processor circuitry 24 (also referred to as "processor"), memory 26, stimulation generator 21, sensing module 22, telemetry module 23, sensor 25, and power source 29. Each of these components (also referred to as "modules" may be or include electrical circuitry configured to perform the functions attributed to each respective module). For example, processor 24 may include processing circuitry, stimulation generator 21 may include switch circuitry, sensing module 22 may include sensing circuitry, and telemetry module 23 may include telemetry circuitry. Memory 26 may include any volatile or non-volatile media, such as a random-access memory (RAM), read only memory (ROM), non-volatile RAM (NVRAM), electrically erasable programmable ROM (EEPROM), flash memory, and the like. Memory 26 may store computer-readable instructions that, when executed by processor 24, cause IMD 20 to perform various functions. Memory 26 may be a storage device or other non-transitory medium.

Processor 24 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 24 herein may be embodied as firmware, hardware, software or any combination thereof. Processor 24 controls stimulation generator 21 to apply particular stimulation parameter values, such as amplitude, pulse width, and pulse rate.

In the example shown in FIG. 2, lead 50 includes electrodes 60 located at distal end 54. Processor 24 also controls stimulation generator 21 to generate and apply the stimulation signals to selected combinations of electrodes of the electrode module. In some examples, stimulation generator 21 includes a switch module that couples stimulation signals to selected conductors within lead 50, which, in turn, delivers the stimulation signals across selected electrodes. Such a switch module may be a switch array, switch matrix, multiplexer, or any other type of switching module configured to selectively couple stimulation energy to selected electrodes and to selectively sense bioelectrical neural signals of the spine with selected electrodes.

In other examples, however, stimulation generator 21 does not include a switch module. In these examples, stimulation generator 21 comprises a plurality of pairs of voltage sources, current sources, voltage sinks, or current sinks connected to each of electrodes such that each pair of electrodes has a unique signal generator. In other words, in these examples, each of electrodes is independently controlled via its own signal generator (e.g., via a combination of a regulated voltage source and sink or regulated current source and sink), as opposed to switching signals between electrodes.

Stimulation generator 21 may be a single channel or multi-channel stimulation generator. In particular, stimulation generator 21 may be capable of delivering a single stimulation pulse or multiple stimulation pulses at a given time via a single electrode combination or multiple stimulation pulses at a given time via multiple electrode combinations. In some examples, however, stimulation generator 21 may be configured to deliver multiple channels on a time-interleaved basis. For example, a switch module of stimulation generator 21 may serve to time divide the output of stimulation generator 21 across different electrode combinations at different times to deliver multiple programs or channels of stimulation energy to patient 40. In another example, the stimulation generator 21 may control the independent sources or sinks on a time-interleaved bases.

Figure 3:
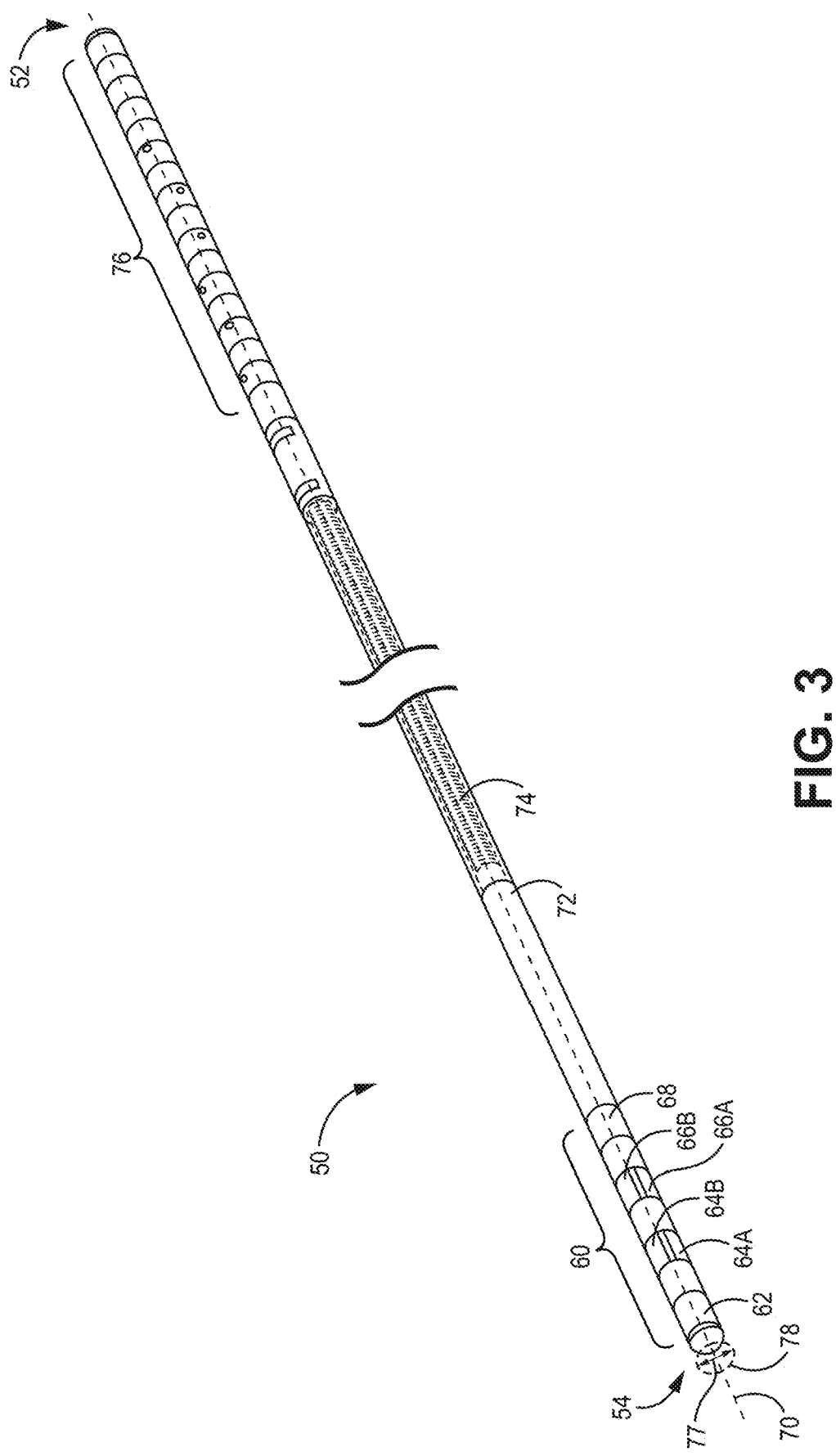
FIG. 3 is a conceptual diagram illustrating an example medical lead.

Lead 50 may include distal end 54 including a complex electrode array geometry, but may also include one or more single ring electrodes along the longitudinal axis in other examples. In one example, distal end 54 of lead 50 includes a plurality of electrodes 60 positioned at different axial positions along the longitudinal axis of the lead and a plurality of electrodes 60 positioned at different angular positions around the circumference of the lead (which may be referred to as electrode segments). In this manner, electrodes may be selected along the longitudinal axis of lead 50 and along the circumference of the lead. Selectively activating electrodes 60 of lead 50 can produce customizable stimulation fields that may be directed to a particular side of lead 50 in order to isolate the stimulation field around the target anatomical region of brain 49. In the example of FIG. 3, lead 50 includes two ring electrodes 68, 62 with two segmented electrode rings 64, 66 each having three segmented electrodes (e.g., segmented electrodes 64A, 64B, 66A, 66B shown in FIG. 3) although the techniques described herein may be applied to leads having more or fewer segmented electrodes within a segmented electrode ring and/or to leads having more or fewer than two segmented electrode rings. These techniques may also be applied to leads having more or fewer than two ring electrodes. In yet other cases, lead 50 may include only segmented electrodes or only ring electrodes.

Although sensing module 22 is incorporated into a common housing with stimulation generator 21 and processor 24 in FIG. 2, in other examples, sensing module 22 may be in a separate housing from IMD 20 and may communicate with processor 24 via wired or wireless communication techniques. Example bioelectrical signals include, but are not limited to, a signal generated from local field potentials within one or more regions of the spine or brain, for example.

Sensor 25 may include one or more sensing elements that sense values of a respective patient parameter. For example, sensor 25 may include one or more accelerometers, optical sensors, chemical sensors, temperature sensors, pressure sensors, or any other types of sensors. Sensor 25 may output patient parameter values that may be used as feedback to control delivery of therapy. IMD 20 may include additional sensors within the housing of IMD 20 and/or coupled as a separate module via one of lead 50 or other leads. In addition, IMD 20 may receive sensor signals wirelessly from remote sensors via telemetry module 23, for example.

In some examples, one or more of these remote sensors may be external to patient (e.g., carried on the external surface of the skin, attached to clothing, or otherwise positioned external to the patient).

Telemetry module 23 supports wireless communication between IMD 20 and an external programmer (e.g., such as programmer 30) or another computing device under the control of processor 24. Processor 24 of IMD 20 may receive, as updates to programs, values for various stimulation parameters such as amplitude and electrode combination, from programmer 30 via telemetry module 23. The updates to the therapy programs may be stored within therapy programs 27 portion of memory 26. Telemetry module 23 in IMD 20, as well as telemetry modules in other devices and systems described herein, such as programmer 30, may accomplish communication by radiofrequency (RF) communication techniques. In addition, telemetry module 23 may communicate with external medical device programmer 30 via proximal inductive interaction of IMD 20 with programmer 30. Accordingly, telemetry module 23 may send information to programmer 30 on a continuous basis, at periodic intervals, or upon request from IMD 20 or programmer 30.

Power source 29 delivers operating power to various components of IMD 20. Power source 29 may include a small rechargeable or non-rechargeable battery and a power generation circuit to produce the operating power. Recharging may be accomplished through proximal inductive interaction between an external charger and an inductive charging coil within IMD 20. In some examples, power requirements may be small enough to allow IMD 20 to utilize patient motion and implement a kinetic energy-scavenging device to trickle charge a rechargeable battery. In other examples, traditional batteries may be used for a limited period of time.

FIG. 3 is a conceptual diagram illustrating an example medical lead 50. In the example of FIG. 3, there are eight conductors corresponding to eight electrodes—2 ring electrodes and 6 segmented electrodes—and eight electrical terminals, such that the lead 50 defines eight isolated electrical paths or channels for delivery of therapy and/or sensing of electrical signals by IMD 20. However, in other examples, greater or fewer conductors, electrodes, and terminals may be used. Lead 50 includes a distal end 54 and a proximal end 52, corresponding to an electrode end and a terminal end, respectively. Distal end 54 and proximal end 52 may define a longitudinal axis 70 along a length of lead 50. Lead 50 includes an outer perimeter 78 that has a diameter 77. In some examples, diameter 77 of outer perimeter 78 may be between 25 and 100 mils, although other values are contemplated.

Lead 50 may include a lead body 72 extending between distal end 54 and proximal end 52. Lead body 72 may be configured to provide structure and support to lead 50 and to encase at least a portion of a plurality of conductors 74. At least a portion of lead body 72 may include conductors in a coiled arrangement. In some examples, lead body 72 may act as an insulator between the plurality of conductors 74. In some examples, lead body 72 may extend through the length of lead 50 as a monolithic form. Lead body 72 may be formed from a polymeric material including, but not limited to, polyurethanes, silicones, fluoropolymers, fluoroelastomers, polyethylenes, polyesters, and other biocompatible polymers suitable for contact with bodily tissue.

Lead 50 may include a plurality of terminals 76 near proximal end 52. Each terminal of the plurality of terminals 76 may be configured to electrically couple to a conductor 74 within lead body 72 of lead 50 and a conductor external of lead 50, such as a contact of IMD 20 of FIG. 1. The plurality of terminals 76 may be positioned at or near proximal end 52 of lead 50. In some examples, each terminal in the plurality of terminals 76 may be a ring contact that extends around outer perimeter 78 of lead 50.

Lead 50 may include the plurality of electrical conductors 74 extending about longitudinal axis 70 of lead 50. The plurality of electrical conductors 74 may be electrically isolated from one another by lead body 72 to form separate channels, circuits, or conductive paths through the lead body 72 although techniques described herein also apply to lead body 72 carrying a single conductor. As shown in FIG. 3, the plurality of conductors 74 may be in a coiled arrangement for at least a portion of lead 50 (e.g., between the electrodes 60 and terminal terminals 76). The coiled arrangement of the plurality of conductors 74 may by wound around longitudinal axis 70 of lead 50. In some examples, the plurality of electrical conductors 74 may include an electrical insulator sheath around a conductive portion. The electrical insulator sheath may be configured to electrically insulate a conductor 74 from undesired contact with an electrode or terminal for which electrical contact is not intended for the conductor 74. In some examples, each of the plurality of electrical conductors 74 may have a diameter, with or without the electrical insulator sheath, between at least about 0.0025 in. and about 0.0080 in.

Each of the plurality of electrical conductors 74 may have a distal connection portion on a distal end and a proximal connection portion on a proximal end of each conductor. The distal and proximal connection portions may be configured to electrically couple each of the plurality of electrical conductors 74 to a respective electrode of the plurality of electrodes 60 and a respective terminal of the plurality of terminals 76. In some examples, the distal and proximal connection portions may include connections sleeves around a perimeter of the respective conductor, where a diameter of each connection sleeve may be larger, smaller, or the same size as a diameter of the remainder conductor body of the respective conductor. In some examples, such as for conductors having an electrical insulator sheath described above, the plurality of conductors 74 may not have distal or proximal connection portions that include connection sleeves. For example, a distal portion of the electrical insulator sheath of a conductor may be removed to expose bare metal conductor. This bare metal conductor may operate as the distal connection portion to electrically contact an electrode or terminal. Each of the plurality of electrodes 60 may be formed from an electrically conductive material including, but not limited to, platinum, palladium, iridium, titanium and titanium alloys such as titanium molybdenum alloy (TiMoly), nickel and nickel alloys such as MP35N alloy, and the like. For example, electrodes may be formed from an 80/20 platinum/iridium alloy suitable for mechanical crimping.

Lead 50 may include a plurality of electrodes 60 near distal end 54. In the example of FIG. 3, the plurality of electrodes 60 includes ring electrodes 62 and 68, and segmented electrodes, such as segmented electrodes 64A, 64B, 66A, and 66B. While only segmented electrodes 64A, 64B, 66A, and 66B are shown, the segmented electrodes may form a discontinuous conductive ring that includes a plurality of electrodes, such as 64A, 64B, and an anterior electrode 64C (not shown) for an exemplary ring of three segmented electrodes on one ring (collectively referred to as "segmented electrode ring 64"), and 66A, 66B, and an anterior electrode 66C (not shown) on another ring (collectively referred to as "segmented electrode ring 66"). Each segmented electrode of a respective discontinuous segmented electrode ring is electrically isolated from the other segmented electrodes in the respective discontinuous segmented electrode ring. For example, segmented electrodes 64A and 64B, which are part of discontinuous segmented electrode ring 64, are electrically isolated from each other. In this example, there are two sets of three segmented electrodes forming segmented electrode rings 64 and 66 at distal end 54 of lead 50, such that each set of segmented electrodes forming segmented electrode rings 64 and 66 is aligned along a longitudinal axis of the electrode module and the sets are positioned circumferentially around outer perimeter 78 of lead 50.

The plurality of electrodes 60 of lead 50 may be constructed of a variety of different designs. For example, one or more leads 50 may include two or more electrodes at each longitudinal location along the length of the lead, such as multiple electrodes at different perimeter locations around outer perimeter 78 of lead 50 at each of the locations, such as by using electrode modules. As mentioned above, each electrode of the plurality of electrodes 60 may be electrically coupled to a respective electrical conductor of the plurality of electrical conductors 74. Each of the plurality of electrodes 60 may be formed from a biocompatible electrically conductive material including, but not limited to, platinum, palladium, iridium, and other biocompatible materials suitable for contact with bodily tissue. For example, electrodes may be formed from a 90/10 platinum/iridium alloy.

As mentioned above, an example manufacturing process for a lead having segmented electrodes may include positioning conductors along an axis of the lead, forming a lead body around the conductors, and forming electrodes around a distal end of the lead body and terminals around a proximal end of the lead body. The conductors may require external support, such as a removable fixture, to maintain proper alignment so that each of the conductors may make contact with a respective electrode and terminal. The resulting lead may contain surface electrodes and terminals that are not securely attached to the lead body. Due to their generally thin configuration, these surface electrodes may be limited to substantially planar designs near a surface of the lead.

According to some examples of the disclosure, a medical lead, such as lead 50, may be manufactured from electrode and/or terminal preformed segments ("preforms") positioned on a conductor preassembly. Rather than form discrete electrodes and terminals at a surface of a lead body, the electrodes and terminals may be formed from structured, electrically conductive rings of electrode and/or terminal preforms that may be more precisely manufactured and arranged than equivalent discrete electrodes and terminals. Similarly, rather than form a lead body around discrete conductors near electrodes, channels may be formed into the preforms that result in conductors that are more precisely manufactured and arranged than equivalent discrete conductors. During assembly, the preforms are positioned on a preassembly that includes conductors, and optionally, connection sleeves. These preforms may support the conductors during manufacture of the lead and form part of the lead with reduced external support and higher precision of placement than lead preassemblies that do not use preforms. For example, the preforms may aid in manufacturing by holding a conductor in contact with a preform for easier welding, keeping a conductor from an outer diameter of the preform to prevent grinding the conductor, or securing the conductor and/or preform during any other processing step that may move the conductor or preform. By assembling leads from preforms, a resulting lead may have precisely placed conductors within a lead, precisely placed electrodes at a surface of the lead, securely anchored electrodes within the lead.

Medical leads, such as lead 50 of FIG. 3, manufactured using the techniques described herein, may include a conductor preassembly as an intermediate during manufacture of the medical lead. The conductor preassembly may act as a conductor backbone for positioning and securing preforms to the conductors before forming a monolithic lead body throughout the lead. FIGS. 4A and 4B are conceptual diagrams illustrating an example conductor preassembly 80 for medical lead 50. Preassembly 80 will be described in terms of a preassembly for lead 50 of FIG. 3; however, similar preassemblies may be used for other lead designs, such as lead 210 of FIG. 10. FIG. 4A illustrates a distal end of preassembly 80 that corresponds to distal end 54 of lead 50, while FIG. 4B illustrates a proximal end of preassembly 80 that corresponds to proximal end 52 of lead 50. While not shown, preassembly 80 includes a longitudinal axis extending from proximal end 52 to distal end 54, as shown in FIG. 3.

In the example of FIGS. 4A and 4B, preassembly 80 may be an intermediate configuration of lead 50 configured for positioning of electrode preforms on preassembly 80. Preassembly 80 may include a central lumen 82 along a longitudinal axis of preassembly 80. The plurality of conductors 74 may be wrapped around lumen 82 from a position near proximal end 52 to a position near distal end 54. In some examples, central lumen 82 may extend through a coiled portion during positioning of the electrode preforms and may be extended during a subsequent overmold from near the coiled portion to proximal end 52. At proximal end 52, the plurality of conductors 74 may be separate and straight for coupling to structures corresponding to the plurality of terminals 76 of FIG. 3. At distal end 54, the plurality of conductors may be separate and straight for coupling to structures corresponding to the plurality of electrodes 60 of FIG. 3. For example, distal end 54 may include a conductor hub that transitions the plurality of conductors 74 from a wrapped configuration into a straight configuration. Lead body 72 may encase a portion of the plurality of conductors 74, such as up through a coiled portion of the plurality of conductors 74.

In the example of FIG. 4A, each conductor of the plurality of conductors 74 may include a connection sleeve of a plurality of distal connection sleeves 84 at distal end 54. The plurality of distal connection sleeves 84 labeled are only two instances of the element and the other elements in the figure are not labeled, e.g., for ease of illustration or description. Each connection sleeve of the plurality of distal connection sleeves 84 may be configured to couple a conductor of the plurality of conductors 74 to an electrode of the plurality of electrodes 60 of FIGS. 1-3. In the example of FIG. 4A, each of the plurality of distal connection sleeves 84 has a larger diameter than the plurality of conductors 74. However, in some examples, such as the examples of FIGS. 8-13, each conductor of the plurality of conductors 74 may have a connection portion that does not include a connection sleeve, or each of the plurality of distal connection sleeves 84 may have a smaller diameter than the plurality of conductors 74. In examples where the plurality of distal connection sleeves 84 have larger diameters than the plurality of conductors 74, an electrode preform may be positioned around a portion of the plurality of conductors 74 before attachment of the plurality of distal connection sleeves 84. In examples where the plurality of distal connection sleeves 84 have smaller diameters than the plurality of conductors 74, an electrode preform may be positioned around a portion of the plurality of conductors 74 after attachment of the plurality of distal connection sleeves 84, as will be described in more detail in FIGS. 8A and 8B. In the example of FIG. 4A, the plurality of conductors 74 extend to four different lengths, corresponding to four electrode preforms.

In the example of FIG. 4B, each conductor of the plurality of conductors 74 may include a connection sleeve of a plurality of proximal connection sleeves 86. The plurality of proximal connection sleeves 86 labeled are only two instances of the element and the other elements in the figure are not labeled, e.g., for ease of illustration or description. Each connection sleeve of the plurality of proximal connection sleeves 86 may be configured to couple a conductor of the plurality of conductors 74 to a terminal of the plurality of terminals 76 of FIG. 3. In the example of FIG. 4B, each of the plurality of proximal connection sleeves 86 has a larger diameter than each of the plurality of conductors 74; however, in some examples, the plurality of proximal connection sleeves 86 may have a smaller diameter than the plurality of conductors 74. In examples where the plurality of proximal connection sleeves 86 have larger diameters than the plurality of conductors 74, a terminal preform may be positioned around a portion of the plurality of conductors 74 before attachment of the plurality of proximal connection sleeves 86. In examples where the plurality of proximal connection sleeves 86 have smaller diameters than the plurality of conductors 74, an electrode preform may be positioned around a portion of the plurality of conductors 74 after attachment of the plurality of proximal connection sleeves 86. In the example of FIG. 4B, the plurality of conductors extends to eight different lengths, corresponding to eight terminal preforms.

In the example of FIGS. 4A and 4B, each of the plurality of distal connection sleeves 84 may be electrically coupled to one of the plurality of proximal connection sleeves 86 through a conductor of the plurality of conductors 74. For example, distal connection sleeve 84A may be coupled to conductor 74A, as shown in FIG. 4A, and proximal connection sleeve 86A may be coupled to conductor 74A, as shown in FIG. 4B, to electrically couple distal connection sleeve 84A to proximal connection sleeve 86A. Distal connection sleeve 84A and proximal connection sleeve 86A may each be coupled to one of the plurality of electrodes 60 and one of the plurality of terminals 76, respectively, to electrically couple the one of the plurality of electrodes 60 and one of the plurality of terminals 76, as described herein.

While FIGS. 4A and 4B are illustrated with a plurality of distal connection sleeves 84 and a plurality of proximal connection sleeves 86, in some examples, the plurality of conductors 74 may be configured to be directly coupled to the plurality of electrodes 60 or the plurality of terminal 76. For example, each of the plurality of conductors may include an electrically insulated sleeve around a conductive material. The electrically insulated sleeve may be absent at an end of the conductor corresponding to a position of one of the plurality of distal connection sleeves 84 or the plurality of proximal connection sleeves 86, such that the conductive material is exposed. The exposed conductive material may be directly coupled to one of the plurality of electrodes 60 or the plurality of terminals 76.

FIGS. 5-7 illustrate various intermediate steps and assemblies used to form a plurality of electrodes at a distal end of a lead, such as the plurality of electrodes 60 at distal end 54 of lead 50. Electrode preforms corresponding to electrodes, such as the plurality of electrodes 60, may be positioned on and secured to the conductor preassembly, such as the conductor preassembly 80 of FIGS. 4A and 4B, to form a preform preassembly.

Figure 5B:
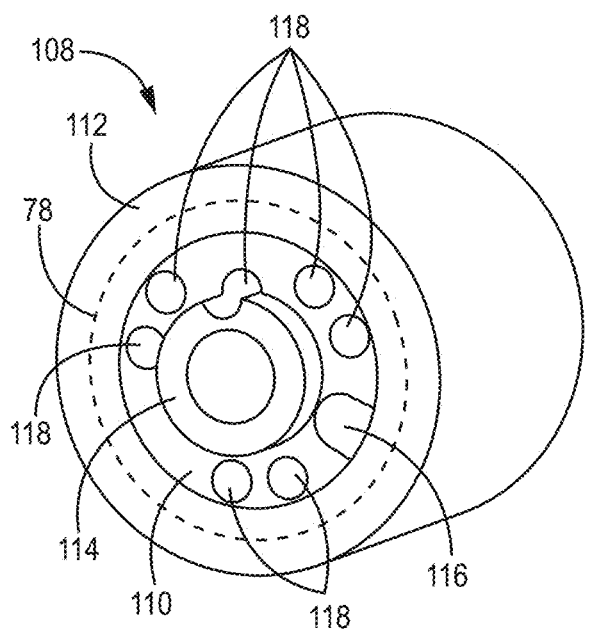
FIG. 5B is a conceptual diagram illustrating a ring electrode preform.

FIG. 5A is a conceptual diagram illustrating a distal portion of an example preform preassembly 100 for medical lead 50. The conductor preassembly and/or preform preassembly may be secured and/or positioned in a cavity during placement of the preforms and/or prior to and during welding of the conductors to the preforms. In the example of FIG. 5A, electrode preforms 102, 104, 106, and 108 have been positioned near distal end 54 of conductor preassembly 80 shown in FIG. 4A to form preform preassembly 100. For example, ring electrode preform 102 may be positioned to electrically contact distal connection sleeve 84A of conductor 74A. In the example of FIG. 5A, electrode preforms include ring electrode preforms 102 and 108 and segmented electrode preforms 104 and 106. Ring electrode preforms may be configured to form a single continuous ring electrode after grinding of an outer perimeter of a lead intermediate to a final medical lead form. As such, ring electrode preforms 102 and 108 may each include an electrically conductive ring that is continuous at a radius from a center of the electrically conductive ring that corresponds to outer perimeter 78 of lead 50, as further described in FIGS. 5B and 5E. Unlike ring electrode preforms, segmented electrode preforms may be configured to form a plurality of discrete, segmented electrodes after grinding. As such, segmented electrode preforms 104 and 106 may each include an electrically conductive ring that is discontinuous at a radius from a center of the electrically conductive ring that corresponds to outer perimeter 78 of lead 50, as further described in FIGS. 5C and 5D. In other words, the electrically conductive ring includes some portions (e.g., electrode portions 136 of FIG. 5C) that are generally at a first radius from the center of the ring that coincides with outer perimeter 78 of lead, and other portions (e.g., raised portions 134 of FIG. 5C) that are generally at a second radius from the center of the ring that extend beyond the outer perimeter 78 of lead. In preassembly 100, the ring electrode preforms 102 and 108 may correspond to ring electrodes 62 and 68, respectively, of lead 50 of FIG. 3. Similarly, the segmented electrode preforms 104 and 106 may correspond to segmented electrode rings 64 and 66, respectively, of lead 50 of FIG. 3, including segmented electrodes 64A, 64B, 64C (not shown), 66A, 66B, 66C (not shown).

Each of electrode preforms 102, 104, 106, and 108 may be formed from a continuous electrically conductive ring. Each conductive ring may be configured for use as one or more electrodes, such as an electrode of the plurality of electrodes 60 of FIG. 3. The conductive ring may be filled with an insulator portion that corresponds to a portion of lead body 72 of FIG. 3. The insulator portion may be an electrical insulator configured to electrically insulate each of the plurality of conductors 74 from each other conductor. The insulator portion may be formed with channels configured to house either a conductor or a connection sleeve configured for an end of a conductor. The conductor channels of an electrode preform may be configured to pass through conductors configured for coupling to electrode preforms distal to the electrode preform, while the connection channels may be configured to house a connection portion or connection sleeve of a conductor for coupling to the particular electrode preform. As such, a particular electrode preform may include a number of connection channels consistent with a predetermined number of electrodes or electrode portions corresponding to the particular electrode preform and a number of connection channels consistent with a predetermined number of electrodes or electrode portions associated with electrode preforms distal to the particular electrode preform. In some examples, electrode preforms may have a diameter between about 0.05 and about 0.1 inches, or between about 0.065 and about 0.075 inches, or between about 0.069 and about 0.071 inches.

FIG. 5B is a conceptual diagram illustrating ring electrode preform 108 of FIG. 5A. Ring electrode preform 108 includes a conductive ring 112. Conductive ring 112 is continuous at a radius from a center of conductive ring 112 that corresponds to outer perimeter 78 of lead 50 of FIG. 3. While a center is used as a reference for purposes of describing conductive ring 112, the center may not be required to be used during grinding, such as in centerless grinding. Ring electrode preform 108 includes an insulator portion 110 that includes a connection channel 116 and a plurality of conductor channels 118; in this instance, one connection channel 116 corresponding to electrical contact with ring electrode preform 108 and seven conductor channels 118 corresponding to electrical contact with segmented electrode preforms 106 and 104 and ring electrode preform 102 distal to ring electrode preform 108. Connection channel 116 may be configured to house a connection sleeve of the plurality of distal connection sleeves 84 of preassembly 80 of FIG. 4A. At least a portion of a wall of connection channel 116 may border conductive ring 112, such that a connection sleeve in connection channel 116 contacts the portion of the wall. The plurality of conductor channels 118 may be configured to pass through a portion of the plurality of conductors 74 of preassembly 80 of FIG. 4A that correspond to electrode preforms that are distal to ring electrode preform 108; in this case, the portion of the plurality of conductors 74 include seven conductors corresponding to electrode preforms 106, 104, and 102. Due to the configuration of the plurality of conductor channels 118 and connection channel 116, insulator portion 110 may act as both a conductor hub for conductors that couple to distal electrode preforms 102, 104, and 106, and a connection sleeve hub for a corresponding distal connection sleeve that couples to conductive ring 112.

Insulator portion 110 may be positioned around a lumen segment 114. In some examples, lumen segment 114 may be configured to protrude from a proximal and/or distal surface of ring electrode preform 108, as shown in FIG. 5B. During overmolding of preform preassembly 100, melted polymer of the overmold may contact cold polymer of the insulator portion to form a lead body extending through the preassembly 100. To improve adhesion, lumen segment 114 may protrude from the surface to increase contact area between the overmold polymer filling in gaps between electrode preforms and the electrode preforms.

In some examples, preforms described herein may include an electrically conductive ring that includes a plurality of alternating raised portions and electrode portions. The electrically conductive ring may be configured such that the plurality of raised portions is removed during grinding to result in a plurality of electrically isolated electrode portions. Grinding processes such as centerless grinding may be used to control removal of the raised portions, resulting in a lead with precise electrode spacing. For example, a lead having an electrode spacing that is too small or large may result in an electric field that may not be as effectively created as a lead with an improved electrode spacing, such as about 20 degrees. Additionally or alternatively, a lead produced from centerless grinding may be very straight and more easily or precisely placed than a lead that is not produced from centerless grinding. Additionally or alternatively, raised portions may be used as a manufacturing aid to allow for positioning and alignment of the preforms in a manufacturing mold, such as by aligning raised portions of multiple preforms.

Figure 5C:
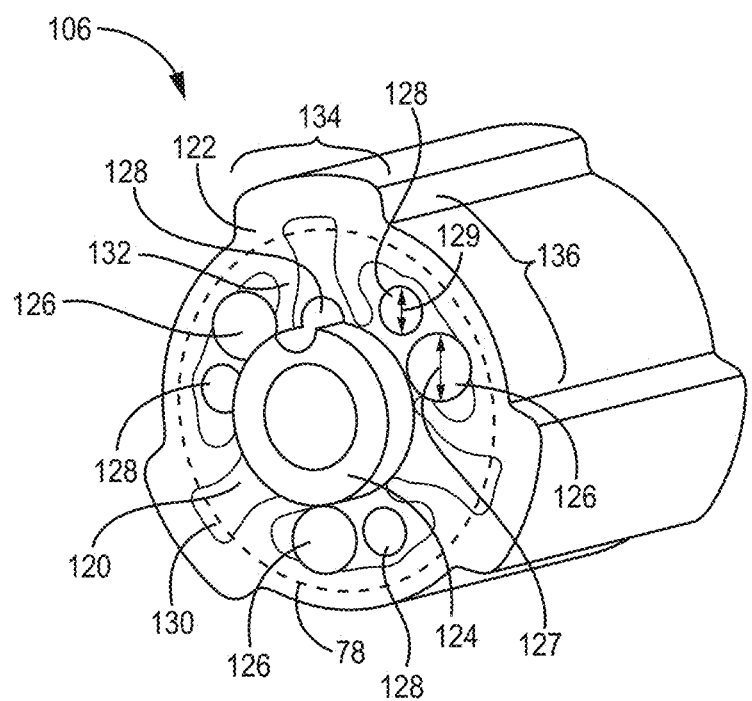
FIG. 5C is a conceptual diagram illustrating a segmented electrode preform.

FIG. 5C is a conceptual diagram illustrating segmented electrode preform 106. Segmented electrode preform 106 includes a conductive ring 122. In contrast to conductive ring 112 of ring electrode preform 108, conductive ring 122 is discontinuous at a radius corresponding to an outer perimeter 78 of lead 50. Conductive ring 122 includes a plurality of electrode portions 136 and a plurality of raised portions 134; in this instance, three electrode portions 136 and three raised portions 134. The electrode portion 136 and raised portion 134 labeled is only one instance of the plurality of electrode portions 136 and the plurality of raised portions 134, respectively, and the other elements in the figure are not labeled, e.g., for ease of illustration or description. A respective electrode portion of the plurality of electrode portions 136 alternates with a respective raised portion of the plurality of raised portion 134 continuously around conductive ring 122. Each of the plurality of electrode portions 136 may be continuous at the radius from the center of conductive ring 122 that corresponds to outer perimeter 78 of lead 50. For example, this may be seen by FIG. 5C which shows outer perimeter 78 (dashed) coinciding in a continuous unbroken manner with each of the electrode portions 136 without traversing any intervening structures or the electrode portions deviating from that perimeter 78. In contrast, each of the plurality of raised portions 134 may be discontinuous or absent at the radius from the center of conductive ring 122 that corresponds to outer perimeter 78 of lead 50 of FIG. 3. For example, this may be seen by outer perimeter 78 of FIG. 5C only partially traversing each raised portion 134 because of a respective intervening insulator portion 120 positioned adjacent raised portion 134 that is situated at, and corresponds with, the outer perimeter 78. As will be described further below, conductive ring 122 may include a plurality of electrode locking features 132. The plurality of electrode locking features 132 may include projections that extend radially inward into segmented electrode preform 106.

Segmented electrode preform 106 includes an insulator portion 120 that includes a plurality of connection channels 126 and a plurality of conductor channels 128; in this instance, three connection channels 126 four conductor channels 128. Insulator portion 120 may be an electrical insulator selected to electrically isolate each of the plurality of conductors 74 and/or connector sleeves 84. Each connection channel of the plurality of connection channels 126 may be configured to house a connection sleeve of the plurality of distal connection sleeves 84 of preassembly 80 of FIG. 4A. At least a portion of a wall of each connection channel of the plurality of connection channels 126 may border an electrode portion 136 of continuous conductive ring 122 so that a connection sleeve 84 positioned in the connection channel may be electrically coupled to the wall. The plurality of conductor channels 128 may be configured to pass through a portion of the plurality of conductors 74 so that the portion of the plurality of conductors may be electrically isolated from electrodes of segmented electrode preform 106 and may be electrically and mechanically coupled to electrodes of electrode preforms that are distal to segmented electrode preform 106. In the example of FIG. 5C, there are four conductor channels 128, corresponding to one conductor for ring electrode preform 102 and three conductors for segmented electrode preform 104, and three connection channels 126, corresponding to three conductors for the three electrode portions 136 of segmented electrode preform 106. Insulator portion 120 may act as both a conductor hub for connection sleeves that couple to distal electrode preforms and a connection sleeve hub for connection sleeves that couple to conductive ring 122. Insulator portion 120 may be positioned around a lumen segment 124. Insulator portion 120 may include a plurality of projections 130 corresponding to the plurality of raised portions 134 of conductive ring 122. Each of the plurality of projections 130 may extend radially outward beyond the radius from the center of conductive ring 122 that corresponds to outer perimeter 78 of lead 50.

As illustrated in FIG. 5C, the plurality of connection channels 126 have a diameter 127 and the plurality of conductor channels 128 have a diameter 129. In this example, diameter 127 is larger than diameter 129. Correspondingly, the plurality of distal connection sleeves 84 may each have a greater diameter than each of the plurality of conductors. This configuration may be used for sequential placement of an electrode preform on a conductor preassembly and subsequent coupling of distal connection sleeves on the next distal electrode preform. For example, segmented electrode preform 106 may be positioned on conductor preassembly 80 such that three connection sleeves 84 are positioned in the three connection channels 126 and the four other conductors 74 are positioned in the four conductor channels 128. The four other conductors may not be coupled to connection sleeves 84 at the time segmented electrode preform 106 is positioned, as the larger diameter connection sleeves may not fit through the small diameter conductor channels. Once segmented electrode preform 106 is positioned, connection sleeves may be coupled to at least three of the four conductors 74 that passed through segmented electrode preform 106. Segmented electrode preform 104 may then be positioned on the at least three conductors 74.

Figure 5D:
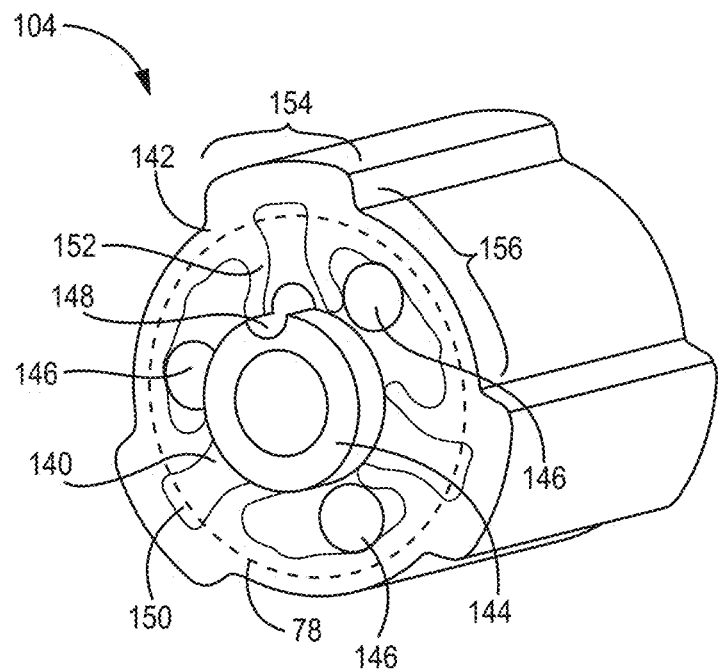
FIG. 5D is a conceptual diagram illustrating a segmented electrode preform.

FIG. 5D is a conceptual diagram illustrating segmented electrode preform 104. Segmented electrode preform 104 may have corresponding features to segmented electrode preform 106 described above, including conductive ring 142, lumen 144, connection channels 146, projections 150, electrode locking features 152, raised portions 154, and electrode portions 156. However, segmented electrode preform 104 may have only a single conductor channel for distal ring electrode preform 102.

Figure 5E:
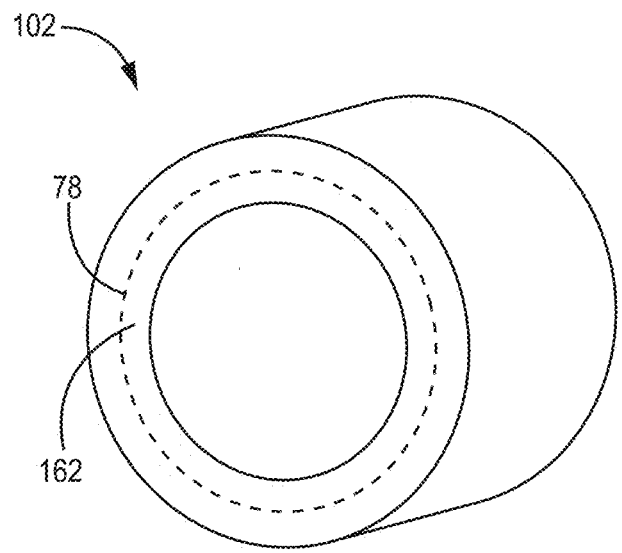
FIG. 5E is a conceptual diagram illustrating a ring electrode preform.

FIG. 5E is a conceptual diagram illustrating ring electrode preform 102. Ring electrode preform 102 includes an electrically conductive ring 162. Conductive ring 162 is continuous at the radius from the center of conductive ring 162 that corresponds to outer perimeter 78 of lead 50.

Referring back to FIG. 5A, electrode preforms 102, 104, 106, and 108, may be coupled to one or more connection sleeves of the plurality of distal connection sleeves 84. A connection sleeve of the plurality of distal connection sleeves 84 may be positioned in each connection channel 126, connection channel 146, and connection channel 116, of segmented electrode preform 106, segmented electrode preform 104, and ring electrode preform 108, respectively. The plurality of electrode portions 136 of segmented electrode preform 106, the plurality of electrode portions 156 of segmented electrode preform 104, and electrically conductive ring 112 of ring electrode preform 108 may be electrically coupled to the respectively connection sleeve of the plurality of distal connection sleeves 84.

A preform preassembly, such as preform preassembly 100 of FIG. 5A, may have an overmold applied to the preassembly to form part of the lead body. The overmold may join at least a portion of the electrode preforms and terminal preforms, and/or encase the preassembly to a substantially uniform perimeter. The resulting "pre-grind" preassembly may form a preassembly to be reduced from a larger diameter of the pre-grind preassembly to a smaller diameter of the medical lead, such as lead 50 of FIG. 3. FIG. 6 is a conceptual diagram illustrating a pre-grind preassembly 164. Preassembly 164 may have an overmold layer 166 forming a surface of preassembly 164 and joining electrode preforms 102, 104, 106, and 108 of FIG. 5A into pre-grind preassembly 164. In some examples, overmold layer 166 may include a same material as insulator portions 110, 120, and 140, of electrode preforms 104, 106, and 108, such that overmold layer 166 and the insulator portions 110, 120, and 140, may form a portion of lead body 72 of FIG. 3. In some examples, overmold layer 166 may completely or partially cover electrode preforms 102, 104, 106, and/or 108. Pre-grind preassembly 164 may have a radius of an outer perimeter 168 that is greater than a radius of outer perimeter 78 of lead 50. In some examples, outer perimeter 168 may have a diameter between 30 and 200 mils, or between about 40 and about 60 mils. In the example of FIG. 6, a surface of pre-grind preassembly 164 may include surfaces of conductive ring 162 from ring electrode preform 102, raised portions 154 of conductive ring 142 of segmented electrode preform 104, raised portions 134 of conductive ring 122 of segmented electrode preform 106, and conductive ring 112 from ring electrode preform 108.

An overmolded pre-grind preassembly, such as pre-grind preassembly 164 of FIG. 6, may be ground to a smaller diameter 77 of an outer perimeter 78 to a form of a medical lead, such as lead 50 of FIG. 3. FIG. 7 is a conceptual diagram illustrating lead 50. During the grinding process, material, including material from conductive rings 112, 122, 142, and 162 and overmold 166, may be removed so that pre-grind preassembly 164 may be reduced from an outer perimeter 168 having a larger diameter 179 to an outer perimeter 78 having a smaller diameter 77. The resulting lead 50 may include ring electrodes 62 and 68, corresponding to ring electrode preforms 102 and 108, and segmented electrode rings 64 and 66, including segmented electrodes 64A, 64B, 64C, 66A, 66B, 66C, corresponding to segmented electrode preforms 104 and 106.

FIGS. 8-14 illustrate variations of electrodes and electrode preforms at a distal end of a medical lead. Electrode preforms may include a variety of alternative design features that aid in securing electrode preforms to a conductor preassembly, decreasing current density at electrode edges, welding connection sleeves to ring electrodes preforms, and securing electrodes to a lead, among other advantages.

In some examples, as will be illustrated further in FIGS. 8A and 8B below, electrode preforms may be configured for sequential placement on a conductor preassembly in order of most proximal to most distal. In the example of FIG. 5C, it was described how an electrode preform may be placed on a conductor preassembly such that conductors intended for coupling to the particular electrode preform may include a larger diameter connection sleeve that is positioned in a correspondingly larger diameter connection channel, while conductors intended for coupling to electrode preforms distal to the particular electrode preform may not include the larger diameter connection sleeve, so that the conductor may be placed in the smaller diameter conductor channel. Once the particular electrode preform has been positioned, connection sleeves corresponding to conductors intended for coupling to the next electrode preform may be attached to the respective conductors. These alternating steps of electrode preform placement and connection sleeve attachment may continue until all the electrode preforms have been placed on the conductor assembly.

In addition to this sequential placement of electrode preform and distal connection sleeve, an embodiment may include sequential placement of electrode preforms without subsequent attachment of connection sleeves. In this example, the conductor preassembly may have a connection sleeve coupled to an end of each conductor. Each connection sleeve in the conductor preassembly may have a diameter smaller or a same size as a diameter of each corresponding conductor. Each electrode preform may have connection channels that have diameters that are correspondingly smaller or a same size as a diameter of each corresponding conductor channel of any proximal electrode preforms. During assembly of the preform preassembly, an electrode preform may be positioned onto the conductor preassembly so that the connection sleeve or connection portion of the conductor corresponding to the particular electrode preform may fit into the smaller connection channel, while conductors, corresponding to electrode preforms to be placed distally to the electrode preform, pass through the larger conductor channels. If a larger diameter connection sleeve had been attached to the pass-through conductors before placement of the electrode preform, as in the example, of FIG. 5C, the electrode preform could not pass through the conductor, as the larger diameter connection sleeve would not pass through the smaller diameter conductor channels. In examples where the connection channel is smaller than the conductor channel, the electrode preform may be prevented from further proximal movement down the conductor, as the conductor may have a larger diameter than the connection channel. In this way, electrode preforms may be efficiently positioned onto a conductor preassembly.

A resulting medical lead formed from electrode preforms as described above may have a plurality of electrical conductors, each electrical conductor having a conductor body and a distal and/or connection portion. The conductor body of each electrical conductor may be positioned in a conductor channel of the medical lead and the distal connection portion of each electrical conductor is positioned in a connection channel of the medical lead. The conductor channel and connection channel of the medical lead may correspond to conductor channels and connection channels of electrode preforms as described above. A diameter of the conductor channel of the medical lead may be greater than or equal to a diameter of the connection channel of the medical lead.

While the principles described above were with respect to electrode preforms, the same concepts may apply to terminal preforms used to form, for example, the plurality of terminals 76 of FIG. 3. Terminal preforms may be configured for sequential placement of the terminal preforms on a conductor preassembly in order of most distal to most proximal. Each conductor of the plurality of electrical conductors may include a proximal connection portion that is positioned in a connection channel corresponding to a connection channel of a terminal preform, while a portion of the conductor body of the conductor may be positioned in a portion of the conductor channel that corresponds to a conductor channel of a terminal preform.

Figure 8A:
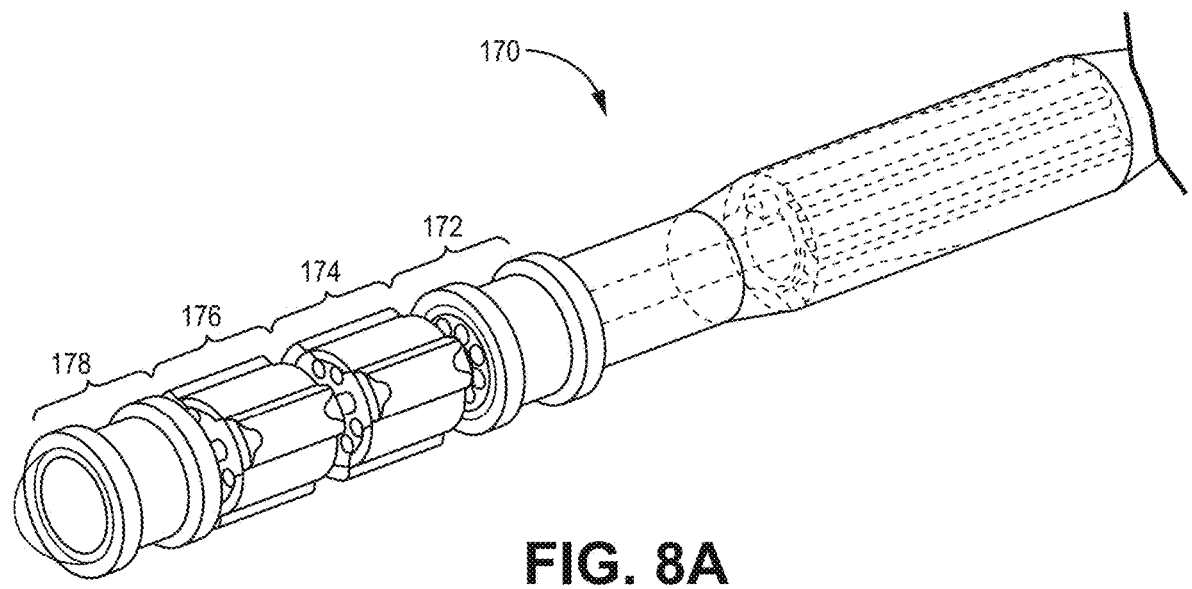
FIG. 8A is a conceptual diagram illustrating an example preform preassembly for a medical lead.

FIG. 8A is a conceptual diagram illustrating an example preform preassembly 170 for medical lead 210, wherein the preform segments have connection channels that have a smaller diameter than a diameter of conductor channels. In the example of FIG. 8A, preassembly 170 includes electrode preforms positioned on a plurality of conductors and a plurality of distal connection portions. The connection sleeves may be smaller than the conductors so that each electrode preform may be positioned on the preassembly after the connection sleeves are coupled to the conductors. In this example, the electrode preforms include electrode preforms 172, 174, 176, and 178; ring electrode preforms 172 and 178 may be similar to ring electrode preforms 102 and 108 of FIG. 5A and segmented electrode preforms 174 and 176 may be similar to segmented electrode preforms 104 and 106 of FIG. 5A. In preassembly 170, ring electrode preforms 172 and 178 may correspond to ring electrodes 212 and 218 (not shown) of lead 210 of FIG. 10. Similarly, segmented electrode preforms 174 and 176 may correspond to segmented electrode rings 214 and 216 of lead 210 of FIG. 10. Features of electrode preforms will be described in more detail in FIGS. 8B and 9-14 below.

To assemble preform preassembly 170, ring electrode preform 172 may first be positioned on a conductor preassembly. The conductor assembly may include a plurality of conductors, each having a connection portion at a distal end that has a smaller diameter than an adjacent proximal portion of the conductor. For example, each conductor of the plurality of conductors may have a larger diameter insulator sheath that is removed at the distal end of the conductor to reveal a smaller diameter conductor that represents the connection portion of the conductor. Ring electrode preform 172 may be positioned so that a connection sleeve or connection portion corresponding to ring electrode preform 172 fits into a smaller diameter connection channel and conductors, corresponding to ring electrode preform 178 and segmented electrode preforms 174 and 176, pass through a plurality of larger diameter conductor channels. Segmented electrode preform 174 may be positioned next onto the conductor assembly, followed by segmented electrode preform 176 and ring electrode preform 178. Each electrode preform may be welded to a connection sleeve after placement, or may be welded after placement of all electrode preforms.

Figure 8B:
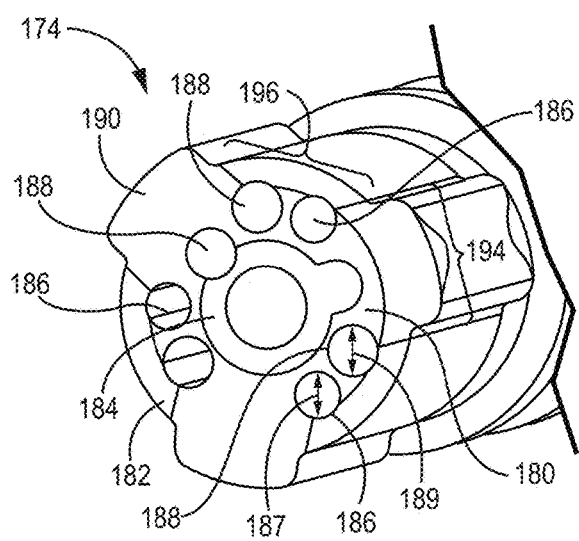
FIG. 8B is a conceptual cross-sectional diagram illustrating an example segmented electrode preform.

FIG. 8B is a conceptual diagram illustrating segmented electrode preform 174 of FIG. 8A. Segmented electrode preform 174 includes a conductive ring 182. Conductive ring 182 includes a plurality of electrode portions 196 and a plurality of raised portions 194. Each of the plurality of electrode portions 196 may be continuous at the radius for an outer perimeter of lead 210, while each of the plurality of raised portions 194 may be discontinuous or absent at the radius for the outer perimeter of lead 50.

Segmented electrode preform 174 includes an insulator portion 180 that includes a plurality of connection channels 186 and a plurality of conductor channels 188; in this instance, three connection channels 186 corresponding to the respective electrode portions 196 and four conductor channels 188 corresponding to three electrode portions of segmented electrode preform 176 and one electrically conductive ring of ring electrode preform 178. Each connection channel 186 may have a diameter 187 that is smaller than a diameter 189 of each conductor channel 188. Each connection channel 186 may be configured to house a connection sleeve of the plurality of connection sleeves 84 of preassembly 80 of FIG. 4A. At least a portion of a wall of each connection channel 186 may border conductive ring 182. The plurality of conductor channels 188 may be configured to pass through a portion of a plurality of conductors. In the example of FIG. 8B, insulator portion 180 includes four conductor channels 188, corresponding to one connection channel (not shown) of ring electrode preform 178 and three connection channels for three electrode portions (not shown) of segmented electrode preform 176, and three connection channels 186, corresponding to three electrode portions 196 of segmented electrode preform 174. Insulator portion 180 may be positioned around a lumen segment 184. Insulator portion 180 may include a plurality of projections 190 corresponding to the plurality of raised portions 194 of conductive ring 182. Each of the plurality of projections 190 may extend radially outward beyond the radius for an outer perimeter of lead 210 of FIG. 10.

Electrode preforms may also include features that reduce an amount of material to be removed during material removal. As discussed above, raised portions of segmented electrode preforms are removed during manufacture of the medical lead to create electrically isolated electrodes. As such, raised portions of segmented electrode preforms may be configured so that an amount of conductive material in the raised portions is reduced. In the example of FIG. 8B, conductive ring 182 has a substantially lower thickness at each of the plurality of raised portions 194 than at each of the plurality of electrode portions 196. A thickness of conductive ring 182 at each of the plurality of raised portions 194 may be such that conductive ring 182 retains a rigid structure during formation of insulator portion 180 while reducing the amount of conductive material of conductive ring 182 that must be removed to achieve a diameter of an outer perimeter of lead 210. In some examples, the raised portions of segmented electrode preforms or ring electrode preforms may be between 0.0001 and 0.001 in. thinner than an adjacent electrode portion.

Figure 9:
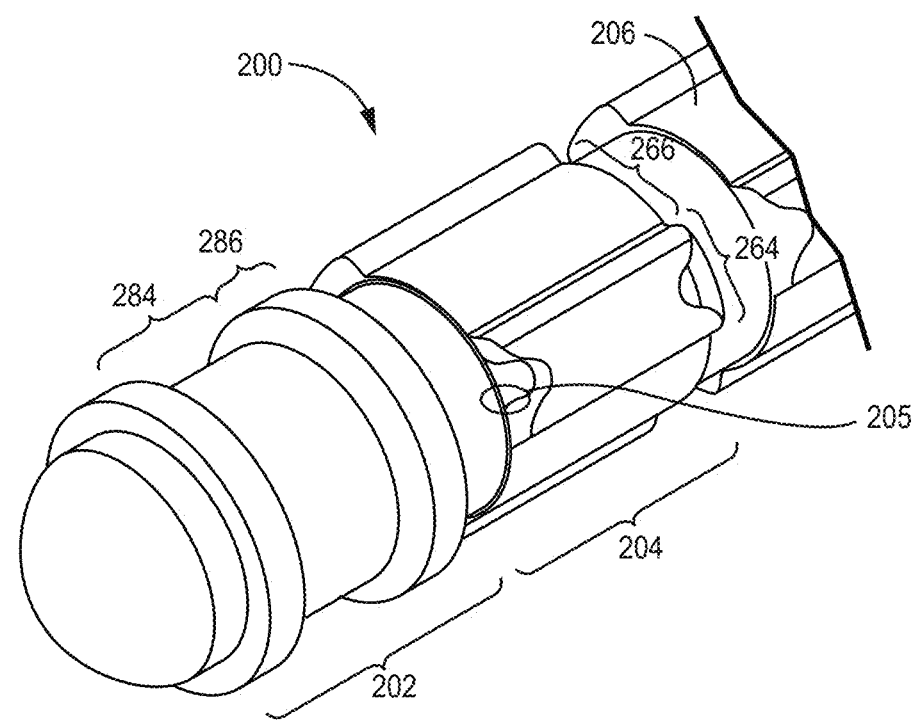
FIG. 9 is a conceptual diagram illustrating an example pre-grind preassembly of a lead.

FIG. 9 is a conceptual diagram illustrating an example pre-grind preassembly 200 of lead 210 before grinding of preassembly 200 to a radius of an outer perimeter of lead 210. The example of FIG. 9 illustrates preassembly 200 having electrode preforms 202, 204, 206, and 208 (not shown); however, a greater or fewer number of electrode preforms may be used.

After an electrode preform is positioned on the conductor preassembly, the conductive ring of the electrode preform may be welded to a respective connection portion. As a thickness of the conductive ring increases, the more energy and heat are required to weld the conductive ring to the connection portion. According to principles of the disclosure, the conductive ring of an electrode preform may have a decreased thickness near a connection channel. For example, as discussed in FIGS. 5C and 5D, each segmented electrode preform may include raised portions and electrode portions. An outer surface of each electrode portion may be radially inward from an outer surface of each raised portion, such that each electrode portion is closer to a respective connection channel. By reducing a thickness, less heat and/or energy may be used to weld the conductive ring, which may result in less interference of the insulator portions with the weld joint.

In addition to segmented electrode preforms, ring electrode preforms may also exhibit decreased conductive ring thickness near a connection channel. As may be seen in FIG. 8B, a distance from an outer surface of the electrode portion 196 to a center of the electrode preform 174 is less than a distance from an outer surface of the raised portion 194 to the center of the electrode preform 174. As a distance between, for example, connection channel 186 and electrode portion 196 is reduced, less energy or heat may be required to weld a connection sleeve or connection portion of a conductor to electrode portion 196. Similarly, ring electrode preforms may have electrode portions that have a reduced thickness and/or distance of an outer surface of the electrode preform to the corresponding connection channel. While the raised portions and electrode portions of segmented electrode preforms may extend down an axis and alternate across a circumference of the segmented electrode preform, raised portions and electrode portions of ring electrode preforms may extend across a circumference and alternate down an axis of the ring electrode preform. FIG. 9 illustrates an example ring electrode preform 202 that may be more easily, economically, or quickly welded to a connection sleeve. Ring electrode preform 202 may correspond to a ring electrode. Ring electrode preform 202 may include one or more raised portions 286 and one or more electrode portions 284. In the example of FIG. 9, ring electrode preform 202 includes two raised portions 286 and one electrode portion 284. Raised portion 286 may be configured to extend to an outer perimeter of preassembly 200. For example, when securing preassembly 170 of FIG. 8A for application of an overmold, each raised portion may act to secure preassembly 170 into a securing structure or to restrict overmold from contact electrode portion 284. Electrode portion 284 may be configured to decrease the amount of heat required to secure a connection sleeve to a wall of ring electrode preform 202. For example, after a connection sleeve is positioned in a connection channel of ring electrode preform 202, a heat source may be applied to an outside of ring electrode preform 202 to weld the connection sleeve with the wall. A thick wall may require more heat to weld the connection sleeve to the wall. By reducing the thickness of the electrode portion 284, a connection sleeve may be welded using less heat that is more concentrated at the connection sleeve. In the example of FIG. 9, raised portion 286 is positioned on an axial edge (i.e. an edge of ring electrode preform 202 at an end along an axis) of ring electrode preform 202; however, in other examples, raised portion 286 may be positioned at other axial positions on ring electrode preform 202.

Medical leads described herein may also exhibit reduced current density at edges of segmented electrodes. Pulses applied to segmented electrodes may create high current densities at edges of the electrode that increase non-uniformity in the current density profile. These current densities may be especially high at corners of electrodes, leading to higher impedances. According to examples of the disclosure, segmented electrode preforms may include features that, when ground from a larger intermediate diameter to a smaller final diameter, result in a segmented electrode with curved edges. These curved edges may be configured to create a more evenly distributed current density around edges of the segmented electrode while maintaining a sufficiently high surface area of the segmented electrode. A more evenly distributed current density may result in an electrode with more effective field steering leading to potentially more precise operation and/or reduced degradation, such as through corrosion, leading to potentially longer life and safer operation.

FIG. 9 illustrates an example segmented electrode preform 204 that may have curved edges for reducing current density at edges of an electrode. Segmented electrode preform 204 may include one or more raised portions 264 and one or more electrode portions 266. Each electrode portion 266 may be bounded by a circumferential perimeter that represent an edge of electrode portion 266 in a circumferential plane corresponding to outer perimeter 78 of lead 50. Once pre-grind preassembly 200 is ground down to diameter 77 of outer perimeter 78, the circumferential perimeter of an electrode portion 266 may form a circumferential perimeter of a segmented electrode, such as segmented electrode 214B in FIG. 10 below. The circumferential perimeter of an electrode portions 266 may include one or more curved portions 205. In the example of FIG. 9, only one curved portion 205 is shown for simplicity; however, each electrode portion 266 may have, for example, four curved portions corresponding to four corners of the electrode portion 266 in the circumferential plane. Characteristics of curved portion 205 will be described further with respect to curved portion 215 of FIG. 10 below; however, it is to be understood that dimensions of curved portion 215 may correspond to dimensions of 205.

Figure 10:
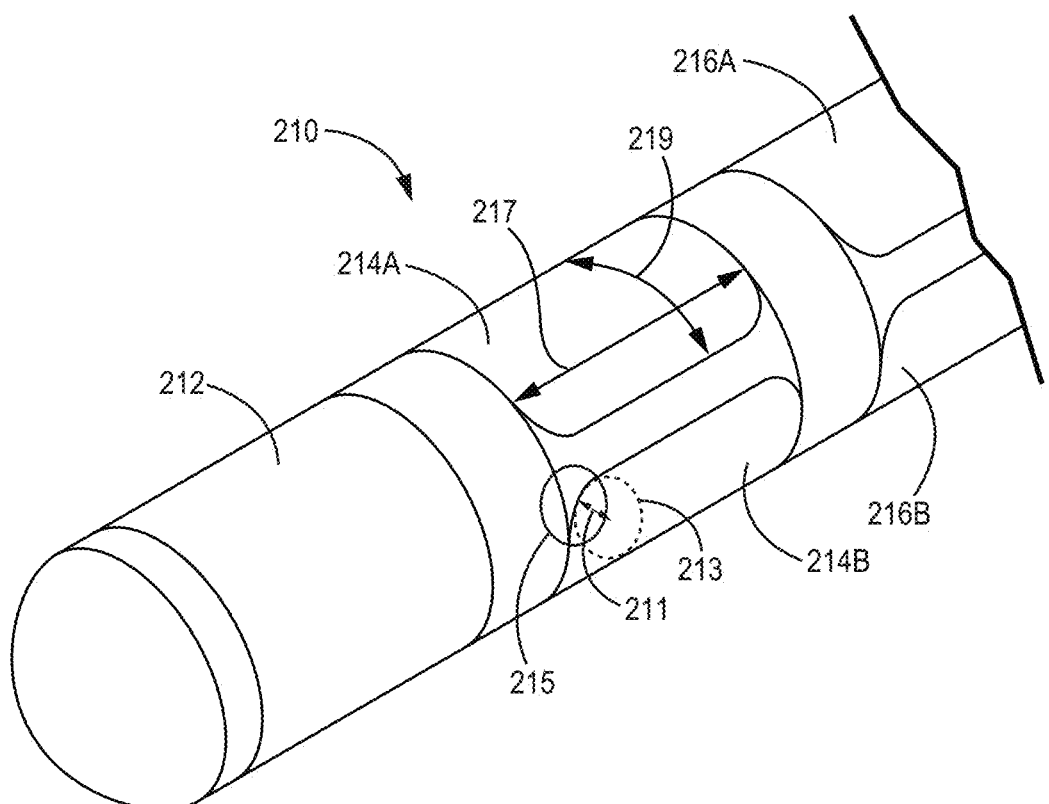
FIG. 10 is a conceptual diagram illustrating a lead formed from the pre-grind preassembly of FIG. 9.

FIG. 10 is a conceptual diagram illustrating lead 210 after grinding of pre-grind preassembly 200 from a larger diameter outer perimeter of preassembly 200 to a smaller diameter outer perimeter of lead 210. The example of FIG. 10 illustrates lead 210 having ring electrodes 212 and 218 (not shown), corresponding to ring electrode preforms 202 and 208 (not shown) of FIG. 9, and segmented electrodes 214A, 214B, and 214C (not shown), and 216A, 216B, and 216C (not shown), corresponding to segmented electrode preforms 204 and 206, respectively; however, a greater or fewer number of electrodes may be used. Raised portions 264 of FIG. 9 have been ground down to a diameter of an outer perimeter of lead 210, such as diameter 77 of outer perimeter 78 of lead 50. As illustrated with segmented electrode 214A, each segmented electrode has a length 217 and a width 219 in a circumferential plane of the outer perimeter of lead 210.

Each of segmented electrodes 214A, 214B, 216A, and 216B has a circumferential perimeter that includes a curved portion, such as electrode curved portion 215. For example, electrode curved portion 215 of segmented electrode 214B corresponds to curved portion 205 of raised portion 264 of FIG. 9. Electrode curved portion 215 may be configured to reduce a current density around the circumferential perimeter of the respective segmented electrode. Segmented electrodes having curved portions of a circumferential perimeter may have more uniform edge current densities than equivalent segmented electrodes having sharper edges in a circumferential perimeter.

In some examples, electrode curved portion 215 may be characterized by a radius 211 of a curve 213 of curved portion 215. In some examples radius 211 may be greater than one tenth of the lesser of length 217 or width 219 of the respective electrode. In some examples radius 211 may be greater than 0.001 inches. See FIGS. 21-23 for examples of segmented electrodes, each having a different radius 211 of a curve 213. In some examples, a segmented electrode may have an oval shape. In some examples, electrode curved portion 215 may be characterized by a percent displaced from a cornered electrode. In some examples, a segmented electrode with one or more curved portions may have a surface area that is at least ten percent less than a surface area of a square, such as a surface area of an equivalent cornered electrode, having length 217 and width 219. See FIG. 20 for an example of a cornered electrode.

Figure 11A:
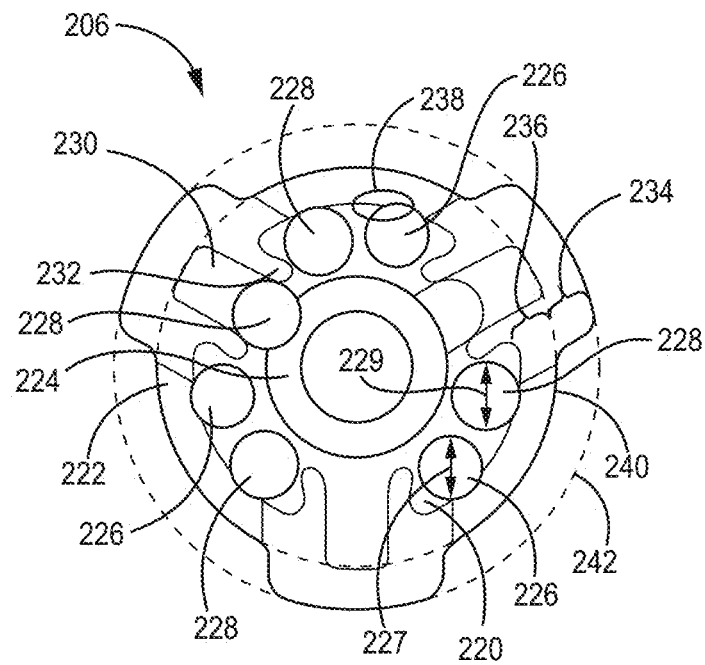
FIG. 11A is a conceptual cross-sectional diagram illustrating an example segmented electrode preform pre-grind.

FIGS. 11A-13B illustrate a difference between pre-grind electrode preforms 204, 206, and 208, and post-grind lead 210 of FIG. 10 at cross-sections corresponding to electrode preforms 204, 206, and 208. FIG. 11A is a conceptual cross-sectional diagram of example pre-grind segmented electrode preform 206. Outer perimeter 242 may represent a pre-grind outer perimeter, while outer perimeter 240 may represent a post-grind outer perimeter. Segmented electrode preform 206 may be similar to segmented electrode preform 106 of FIG. 5C, including insulator portion 220, conductive ring 222, lumen 224, projections 230, electrode locking features 232, raised portions 234, and electrode portions 236. In the example segmented electrode preform 206, electrode portions 236 are represented as portions of conductive ring 222 that are radially inward of post-grind outer perimeter 240 and raised portions 234 are represented as portions of conductive ring 222 that are radially outward of post-grind outer perimeter 240. In the example segmented electrode preform 206, each of a plurality of conductor channels 228 may have a diameter 229 that is larger than a diameter 227 of each of the plurality of connection channels 226. In some examples, the plurality of connection channels 226 and/or the plurality of conductor channels 226 may include an indentation 238 into conductive ring 222, such that a wall between the respective connection channel 226 of the plurality of connection channels 226 and an outside surface of a respective electrode portion 236 is thinner. In the example of FIG. 11A, there are four conductor channels 228, corresponding to conductors intended for connection to ring electrode preform 202 and segmented electrode preform 204, and three connection channels 226, corresponding to conductors intended for connection to segmented electrode preform 206.

Figure 11B:
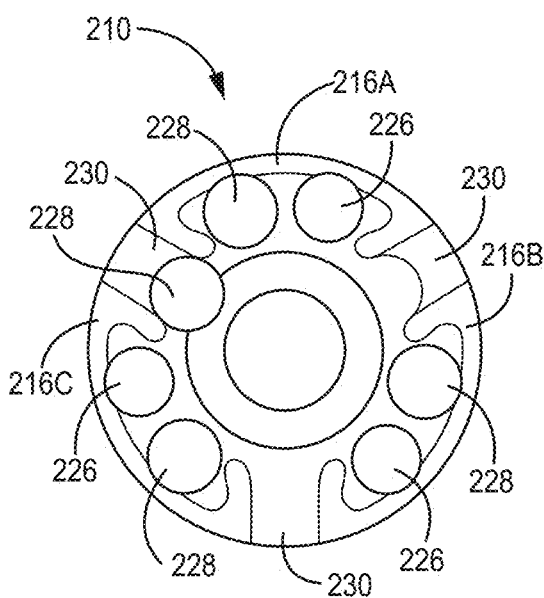
FIG. 11B is a conceptual cross-sectional diagram illustrating an example segmented electrode preform post-grind.

FIG. 11B is a conceptual cross-sectional diagram of example lead 210 at an axial position corresponding to segmented electrode preform 206. Lead 210 has been reduced from a larger diameter of outer perimeter 242 to a smaller diameter of outer perimeter 240. Lead 210 includes segmented electrodes 216A, 216B, and 216C formed from electrode portion 236 of segmented electrode preform 206 and separated by projections 230 of the lead body segment. The plurality of raised portions 234 are ground down from outer perimeter 242 to outer perimeter 240 beyond the plurality of projections 230 such that conductive ring 222 is no longer continuous. Conductive ring 222 now forms three segmented electrodes 216A, 216B, and 216C separated by the lead body portion corresponding to the projections 230 of the insulator portion 220. While not shown, each of the plurality of connection channels 226 includes a connection sleeve 84 or connection portion of a conductor 74, while each of the plurality of conductor channels 228 includes a conductor body of conductor 74.

Figure 12A:
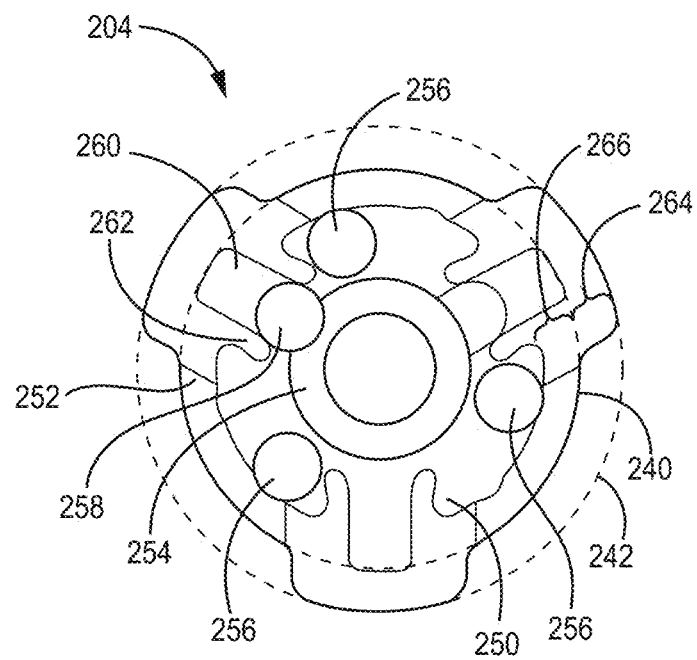
FIG. 12A is a conceptual cross-sectional diagram illustrating an example segmented electrode preform pre-grind.

FIG. 12A is a conceptual cross-sectional diagram of example pre-grind segmented electrode preform 204. Outer perimeter 242 may represent a pre-grind outer perimeter, while outer perimeter 240 may represent a post-grind outer perimeter. Segmented electrode preform 204 may be similar to segmented electrode preform 104 of FIG. 5D, including insulator portion 250, conductive ring 252, lumen 254, projections 260, electrode locking features 262, raised portions 264, and electrode portions 266. In the example segmented electrode preform 204, each of a plurality of conductor channels 258 may be larger than each of the plurality of connection channels 256. In the example segmented electrode preform 204, electrode portions 266 are represented as portions of conductive ring 252 that are radially inward of post-grind outer perimeter 240 and raised portions 264 are represented as portions of conductive ring 252 that are radially outward of post-grind outer perimeter 240. In the example of FIG. 12A, there is one conductor channel 258, corresponding to ring electrode preform 202, and three connection channels 256, corresponding to segmented electrode preform 206.

Figure 12B:
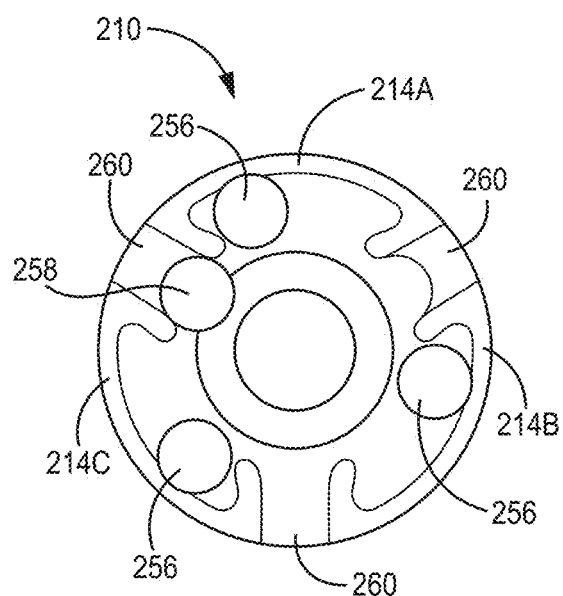
FIG. 12B is a conceptual cross-sectional diagram illustrating an example segmented electrode preform post-grind.

FIG. 12B is a conceptual cross-sectional diagram of example lead 210 at an axial position corresponding to segmented electrode preform 204. Lead 210 has been reduced from a larger diameter of outer perimeter 242 to a smaller diameter of outer perimeter 240. Lead 210 includes segmented electrodes 214A, 214B, and 214C formed from electrode portions 266 of segmented electrode preform 204 and separated by projections 260 of the lead body segment. The plurality of raised portions 264 are ground down beyond the plurality of projections 260 such that conductive ring 252 is no longer continuous. Conductive ring 252 now forms three segmented electrodes 214A, 214B, and 214C separated by the lead body portion corresponding to the projections 260 of the insulator portion 220. While not shown, each of the plurality of connection channels 256 includes a connection sleeve 84 or connection portion of a conductor 74, while the conductor channel 258 includes a conductor 74.

Figure 13A:
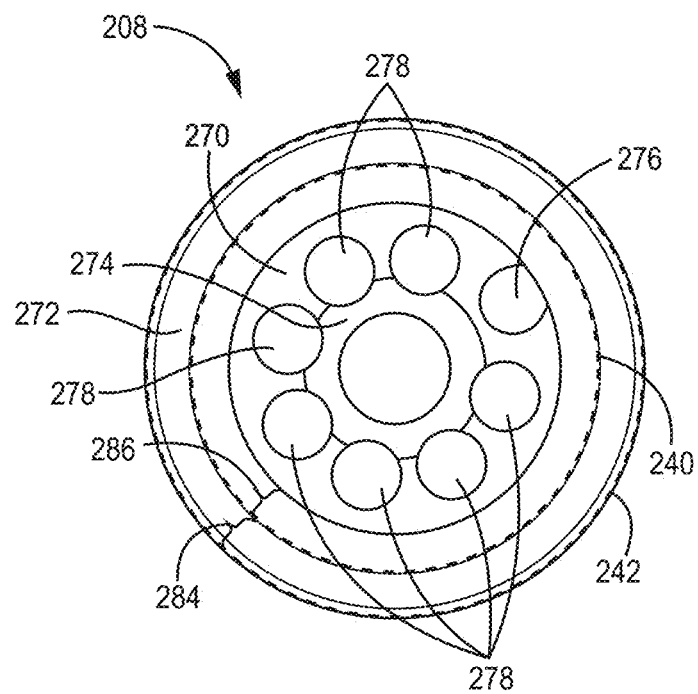
FIG. 13A is a conceptual cross-sectional diagram illustrating an example ring electrode preform pre-grind.

FIG. 13A is a conceptual cross-sectional diagram of example ring electrode preform 208. Outer perimeter 242 may represent a pre-grind outer perimeter, while outer perimeter 240 may represent a post-grind outer perimeter. Ring electrode preform 208 may be similar to ring electrode preform 108 of FIG. 5B, including insulator portion 270, conductive ring 272, and lumen 274. Ring electrode preform 208 includes a smaller connection channel 276 and a plurality of larger conductor channels 278. FIG. 13A also illustrates a raised portion of conductive ring 272 that extends circumferentially and alternates axially across conductive ring 272, such as described in FIG. 9. Conductive ring 272 may include at least one electrode portion 284 and at least one raised portion 286.

Figure 13B:
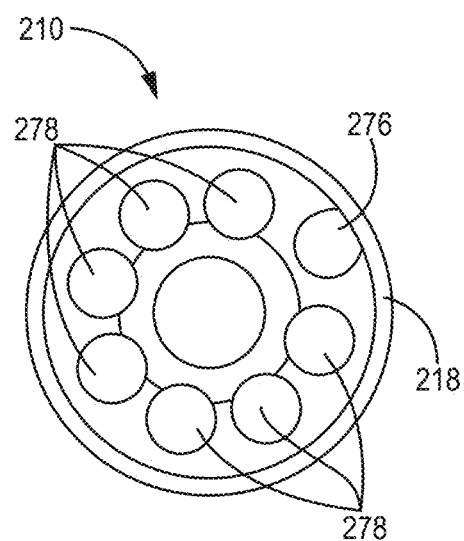
FIG. 13B is a conceptual cross-sectional diagram illustrating an example ring electrode preform post-grind.

FIG. 13B is a conceptual cross-sectional diagram of example lead 210 at an axial position corresponding to segmented electrode preform 204. Lead 210 has been reduced from a larger diameter of outer perimeter 242 to a smaller diameter of outer perimeter 240. Lead 210 includes ring electrode 218 formed from electrode portion 286 of ring electrode preform 208. While not shown, the connection channels 276 includes a connection sleeve 84 or connection portion of a conductor 74, while each of the plurality of conductor channels 278 includes a conductor 74.

Figure 14A:
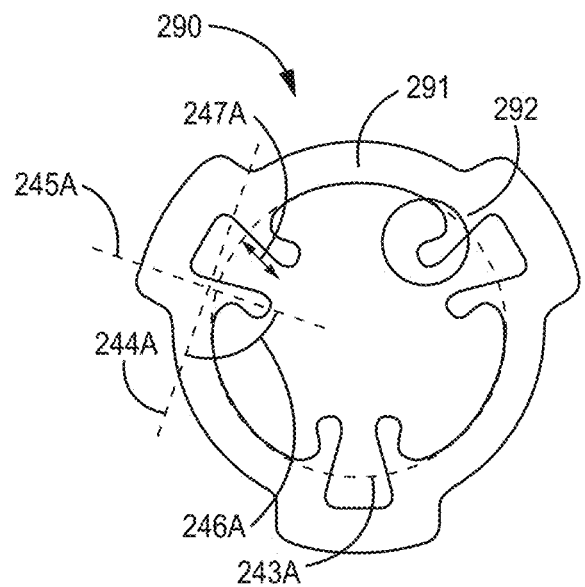
FIG. 14A is a conceptual cross-sectional diagram illustrating an example conductive ring that includes electrode locking features for each electrode portion.
Figure 14B:
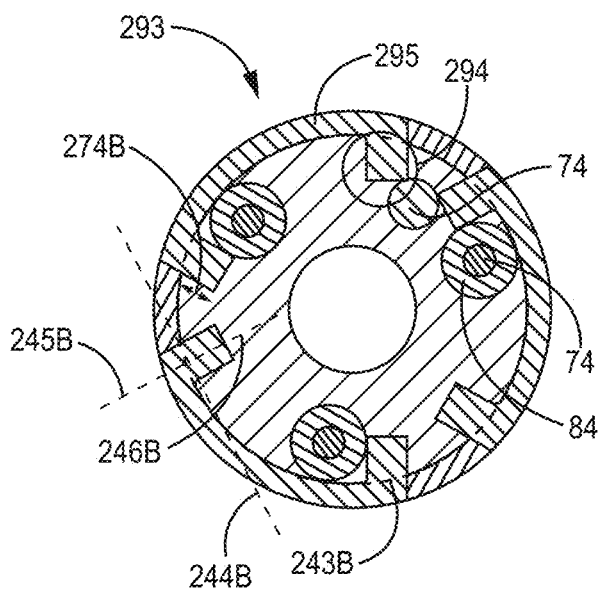
FIG. 14B is a conceptual cross-sectional diagram illustrating a section of a lead that corresponds to a segmented electrode preform post-grinding.
Figure 14C:
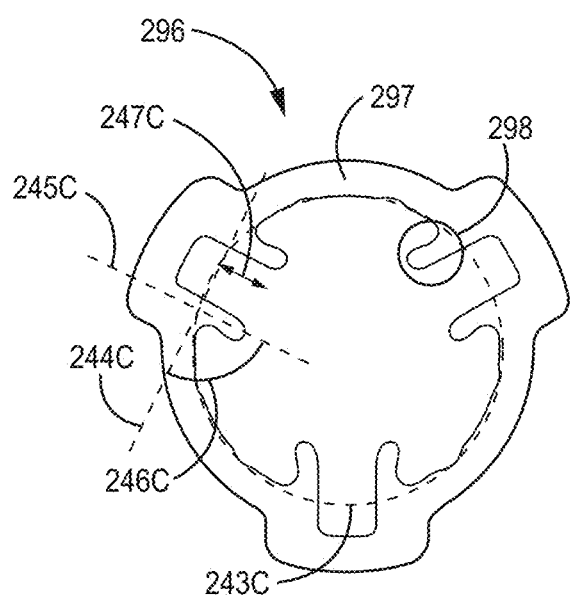
FIG. 14C is a conceptual cross-sectional diagram illustrating an example conductive ring that includes electrode locking features for each electrode portion.

FIGS. 14A-C illustrate examples of electrode locking features that may secure segmented electrodes into a lead body of the lead. As described earlier, electrodes may typically be secured to a lead body after the lead body has been formed. This superficial treatment may limit the depth and forms at which electrodes may be anchored into the lead body. According to principles of the disclosure, segmented electrodes may be secured into the lead body by forming electrode locking features into a conductive ring of a segmented electrode preform and forming the lead body in the conductive ring as an insulator portion. The resulting segmented electrode may have electrode locking features present within the lead body. By including electrode locking features that extend into a body of a lead, the electrodes may be less likely to dislodge or shift in movement, such that the lead may have a longer life, higher reliability, and/or more consistent sensing or stimulation. Such locking features may be particularly desirable when employing segmented electrodes. Unlike ring electrodes, which may be secured, at least in part, by virtue of a ring structure that surrounds the lead body, segmented electrodes do not encircle the lead body and therefore locking features as disclosed herein may be used to provide additional affixation for the segmented electrodes.

Electrode locking features may include any extension or protrusion of a segmented electrode that extends or protrudes radially inward to a center of the conductive ring or lead. Electrode locking features may assist in securing electrodes to a lead body through a variety of means including, but not limited to, physical interlocks, surface adhesion, intermolecular forces, and the like. Electrode locking features may have shapes that include undercuts, bulbs, rounded sections, flat sections, holes, steps, grooves, T-shape sections, and the like. In some examples, electrode locking features may be configured to further contact a conductor channel or connection channel. For example, connection channel may contact an inner surface of the segmented electrode and a surface of the electrode locking features, such that the segmented electrode may contact a connection sleeve at two surfaces.

FIG. 14A is a conceptual cross-sectional diagram of an example conductive ring 290 that includes one or more electrode locking features 292 for each electrode portion 291. In the example of FIG. 14A, only a single instance of each of the electrode locking features 292 and electrode portions 291 are labeled for simplicity; however, six electrode locking features 292 and three electrode portions 291 are shown. Each electrode locking feature 292 is positioned at an end of an electrode portion 291 of conductive ring 290. However, in other examples, electrode locking feature 292 may be located in a middle part of electrode portion 291, or anywhere else radially inward of electrode portion 291.

Inner surfaces of electrode portions 291 define an inner perimeter 243A of conductive ring 290, such that electrode locking features 292 are radially inward of inner perimeter 243A. For example, inner perimeter 243A may be substantially planar with a majority surface area of an inner surface of each of electrode portions 291. In another example, inner perimeter 243A may be defined by an average radius of an inner surface of electrode portions 291 from a center of conductive ring 290. In yet another example, inner perimeter 243A may be defined by a maximum radius of an inner surface of electrode portions 291 from the center of conductive ring 290. Each electrode locking feature 292 may have a centerline 245A (i.e. a line from a center of a base of electrode locking feature 292 to a center of a radial tip of electrode locking feature 292). Each electrode locking feature 292 may also have a tangential baseline 244A of inner perimeter 243A at centerline 245A (i.e. tangent to inner perimeter 243A). Centerline 245A and tangential baseline 244A may form an angle 246A that represents an angle of radial orientation of electrode locking feature 292. Each electrode locking feature 292 may have a length 247A from the base of electrode locking feature 292 (corresponding to inner perimeter 243A) to the tip of electrode locking feature 292 that represents the length of the electrode locking feature from the respective electrode or electrode portion.

Each electrode locking feature 292 may be configured to secure, as a single electrode locking feature 292 or as a plurality of electrode locking features 292, a segmented electrode corresponding to a respective electrode portion 291 to a resulting medical lead. In some examples, angle 246A may be selected such that an outward force on the respective segmented electrode will be resisted by the electrode locking feature 292. In some examples, angle 246A may be less than 120 degrees. In some examples, angle 246A may be between 30 degrees and 90 degrees. In the example of FIG. 14A, angle 246A is about 85 degrees.

In some examples, length 247A may be selected such that an outward force on the respective segmented electrode will be resisted by the electrode locking feature 292, such as through friction. In some examples, length 247A may be between about 0.005 in and about 0.015 in. In some examples, length 247A may be between about 10% and 50% of a radius of inner perimeter 243A. In the example of FIG. 14A, length 247A is about 30% of a radius of inner perimeter 243A.

In some examples, electrode locking feature 292 may have a shape that is selected such that an outward force on the respective segmented electrode will be resisted by the electrode locking feature 292. In some examples, electrode locking feature 292 may have a bulbous, straight, hooked, undercut, T-shape, or other shape. In the example of FIG. 14A, electrode locking feature 292 has a bulbous head that is wider at an end portion than at a stem portion. Such a configuration may lock electrode locking feature 292 into the lead body.

FIG. 14B is a conceptual cross-sectional diagram of a section 293 of a lead that corresponds to a segmented electrode preform. The section 293 includes one or more electrode locking features for each electrode, such as electrode locking feature 294. Electrode locking feature 294 is positioned at an end of electrode 295. The plurality of electrodes 295 may form an inner perimeter 243B, as described in FIG. 14A above. Each electrode locking 294 may have an angle 246B between a centerline 245B and a tangential baseline 244B of inner perimeter 243B, and a length 247B, such as described in FIG. 14A above. In the example of FIG. 14B, a conductor 74 is positioned in a conductor channel (not labeled) and a conductor 74 coupled to a connection sleeve 84 is positioned in each of three connection channels (not labeled).

In the example of FIG. 14B, each electrode locking feature 294 has flat sides that extend radially inward into section 293. In this example, each electrode locking feature 294 extends at least a quarter of a distance from an outer perimeter of section 293 toward a center of section 293 and at an angle that is substantially normal to an inner curve of electrode 295. Electrode locking feature 294 is also configured to contact a connection channel. Electrode locking feature 294 may provide another contact surface between a connection sleeve in connection channel and electrode 295.

FIG. 14C is a conceptual cross-sectional diagram of an example conductive ring 296 that includes one or more electrode locking features for each electrode portion, such as electrode locking feature 298. Electrode locking feature 298 is positioned at an end of an electrode portion 297 of conductive ring 296. The plurality of electrode portions 297 may form an inner perimeter 243C, as described in FIG. 14A above. Each electrode locking 298 may have an angle 246C between a centerline 245C and a tangential baseline 244C of inner perimeter 243C, and a length 247C, such as described in FIG. 14A above. In this example, length 247C of electrode locking feature 298 extends to at least a third of a radius of inner perimeter 243C and at an angle 246C that is not substantially normal to an inner curve of electrode portion 297.

Figure 27A:
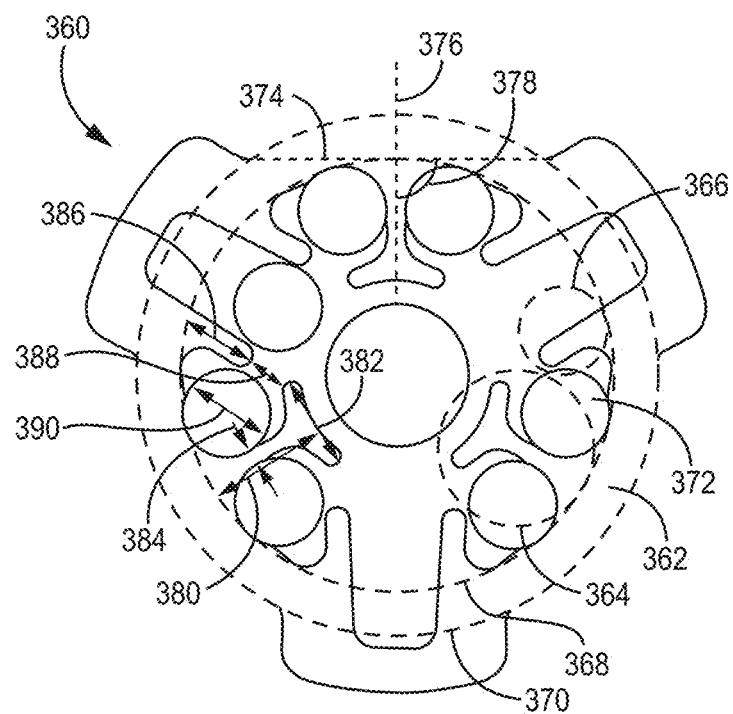
FIG. 27A is a conceptual cross-sectional diagram of an example segmented electrode preform that includes two or more electrode locking features for each electrode portion.

FIG. 27A is a conceptual cross-sectional diagram of an example segmented electrode preform 360 that include one or more electrode locking features for each electrode portion, such as electrode locking features 364 and 366. In the example of FIG. 27A, only a single instance of each of the electrode locking features 364 and 366 and electrode portions 362 are labeled for simplicity; however, three electrode locking features 364, six electrode locking features 366, and three electrode portions 362 are shown. Each electrode locking feature 364 is positioned at a middle of electrode portion 362 and each electrode locking feature 366 is positioned at an end of electrode portion 362 of electrode preform 360. However, in other examples, electrode locking feature 364 and 366 may be anywhere else radially inward of electrode portion 362. Inner surfaces of electrode portions 362 define an inner perimeter 368 of electrode preform 360, such that electrode locking features 364 and 366 are radially inward of inner perimeter 368.

As shown in FIG. 27A, electrode preform 360 may include more than one type of electrode locking feature, such as t-shaped electrode locking feature 364 and electrode locking feature 366. For example, electrode preform 360 includes electrode locking features that includes different shapes and different positions. Electrode locking feature 366 may similar to, for example, electrode locking feature 292 of FIG. 14A. Electrode locking feature 366 may have a length 386 from a base of electrode locking feature 366 to a radially inward tip of electrode locking feature 366.

Each electrode locking feature 364 may have a centerline 376 from a base of electrode locking feature 364 to a radial tip of electrode locking feature 364. Each electrode locking feature 292 may also have a tangential baseline 374 of inner perimeter 368 at centerline 376. Centerline 376 and tangential baseline 374 may form an angle 378 that represents an angle of radial orientation of electrode locking feature 364. Each electrode locking feature 364 may have a length 380 from the base of electrode locking feature 364 (corresponding to inner perimeter 368) to the tip of electrode locking feature 364 that represents the length of the electrode locking feature from the respective electrode or electrode portion. Each electrode locking feature 364 may have a width 382 at the tip of electrode locking feature 364 and a width 384 at a stem of electrode locking feature 364 located between the base and the tip. Width 382 may be greater than width 384, such that the tip of electrode locking feature 364 acts as a t-shape anchor.

Each electrode locking feature 364 and 366 may be configured to secure, alone or in combination, a segmented electrode corresponding to a respective electrode portion 362 to a resulting medical lead. In some examples, length 386 of electrode locking feature 366 and length 380 of electrode locking feature 364 are selected to substantially surround a channel 372 of electrode preform 360, such that a distance 388 between a tip of electrode locking feature 364 and a tip of electrode locking feature 366 is less than a diameter 390 of channel 372 (and, correspondingly, a diameter of an electrical conductor). In some examples, angle 378 may be approximately 90 degrees, such as between about 85 degrees and about 95 degrees.

In some examples, width 382 may be selected such that an outward force on the respective segmented electrode will be resisted by electrode locking feature 366, such as through rigidity. In some examples, width 382 may be between about 0.005 in and about 0.015 in. In some examples, width 382 may be between about 20% and 100% of length 380. In the example of FIG. 14A, width 382 is about 60% of length 380.

In some examples, electrode locking features 364 and 366 may be configured to increase a surface area of channel 372 that is available for coupling to electrode portions 362 and/or guide placement of channel 372. In some examples, at least one of electrode locking features 364 and 366 borders at least a portion of channel 372, electrode portion 362 may be electrically coupled to a respective electrical conductor positioned in channel 372. In some examples, electrode locking features 364 and 366 may be configured to define channels 372, such as by guiding placement of channels 372 in electrode preform 360. For example, during grinding of an insulator portion of electrode preform 360, electrode locking features 364 and 366 may assist in guiding a grinding tool to produce channel 372, such that channels are at appropriate positions and/or adjacent channels are separated.

Figure 27B:
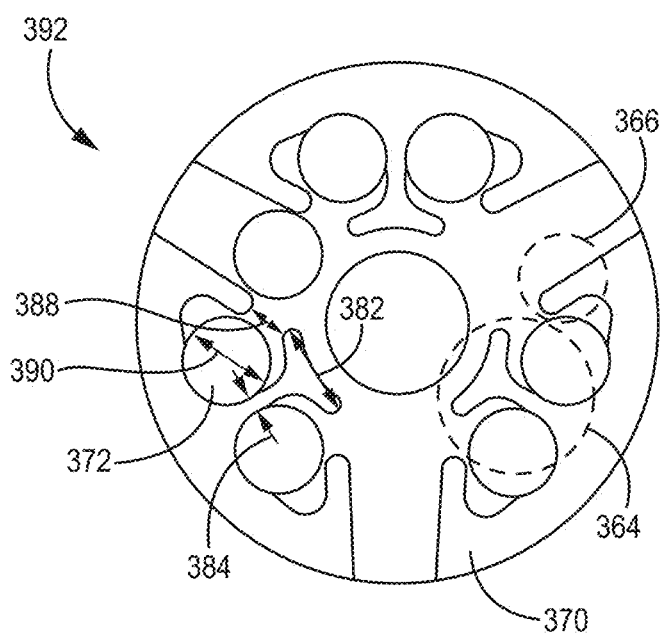
FIG. 27B is a conceptual cross-sectional diagram of an example section of lead corresponding to segmented electrode preform of FIG. 27A having segmented electrodes.

FIG. 27B is a conceptual cross-sectional diagram of an example section of lead 392 corresponding to segmented electrode preform 360 of FIG. 27A having segmented electrodes 394 (shown without conductors in channels 372). As shown in FIG. 27B, electrode locking features 364 and 366 operate to secure segmented electrodes 394 to lead 392. For example, width 382 of an end of electrode locking feature 364 may be greater than width 382 of a stem of electrode locking feature 364, such that segmented electrode portion 362 may remain fixed to lead 392. As another example, distance 388 between a tip of electrode locking feature 364 and a tip of electrode locking feature 366 may be greater than diameter 390 of channel 372, such that an electrical conductor positioned in channel 372 may not pass through distance 388. By using a t-shaped electrode locking feature, as shown in FIGS. 27A and 27B, a lead may include electrodes that are more securely anchored into the lead and that may include more precisely positioned or coupled conductors.

In addition to electrodes formed through electrode preforms, terminals may also be formed through terminal preforms. Terminal formation may be subject to many of the same production issues as electrode formation, such as difficulty in maintaining alignment of terminal rings and poor attachment of terminals formed from a sheet rather than a terminal ring.

According to principles of the disclosure, terminals may be formed by positioning terminal preforms on a conductor preassembly, securing the terminal preforms to their respective conductors, applying an overmold, and grinding the overmolded preassembly to a final lead form. Many of the same advantageous features of the electrode preforms and assemblies, such as distally decreasing hole size and axially inset conductive rings, may apply to formation of the terminals from terminal preforms.

Figure 15A:
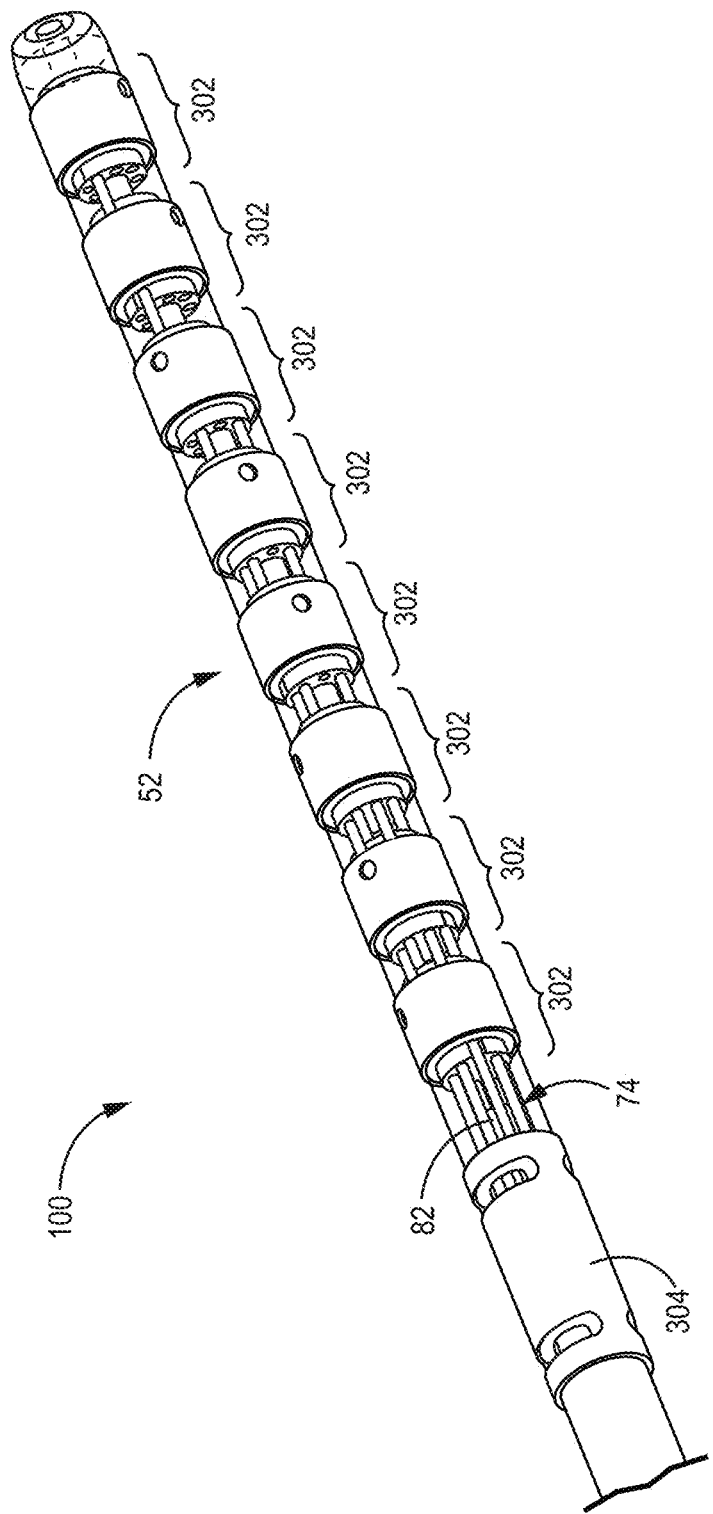
FIG. 15A is a conceptual diagram illustrating a proximal end of an example preform preassembly for a medical lead.
Figure 15B:
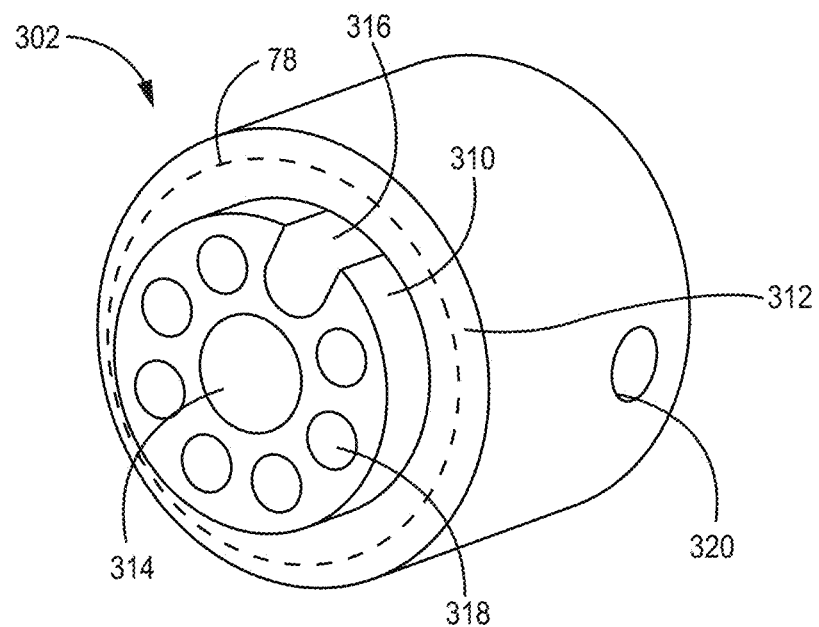
FIG. 15B is a conceptual diagram illustrating a terminal preform.
Figure 15C:
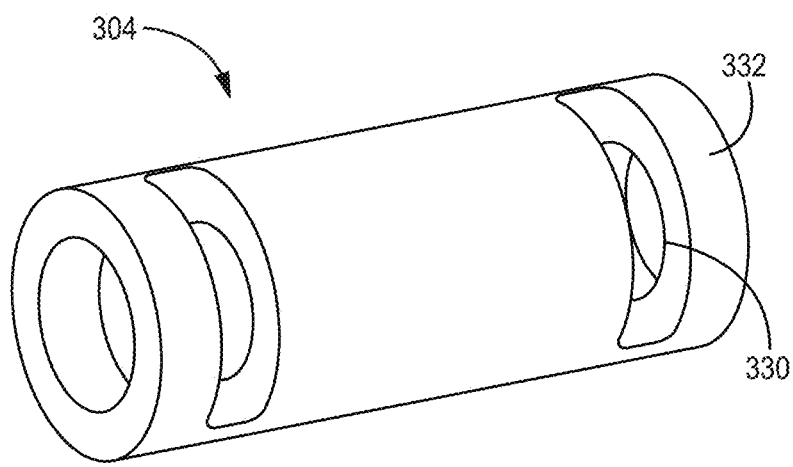
FIG. 15C illustrates a premold retention sleeve.
Figure 16:
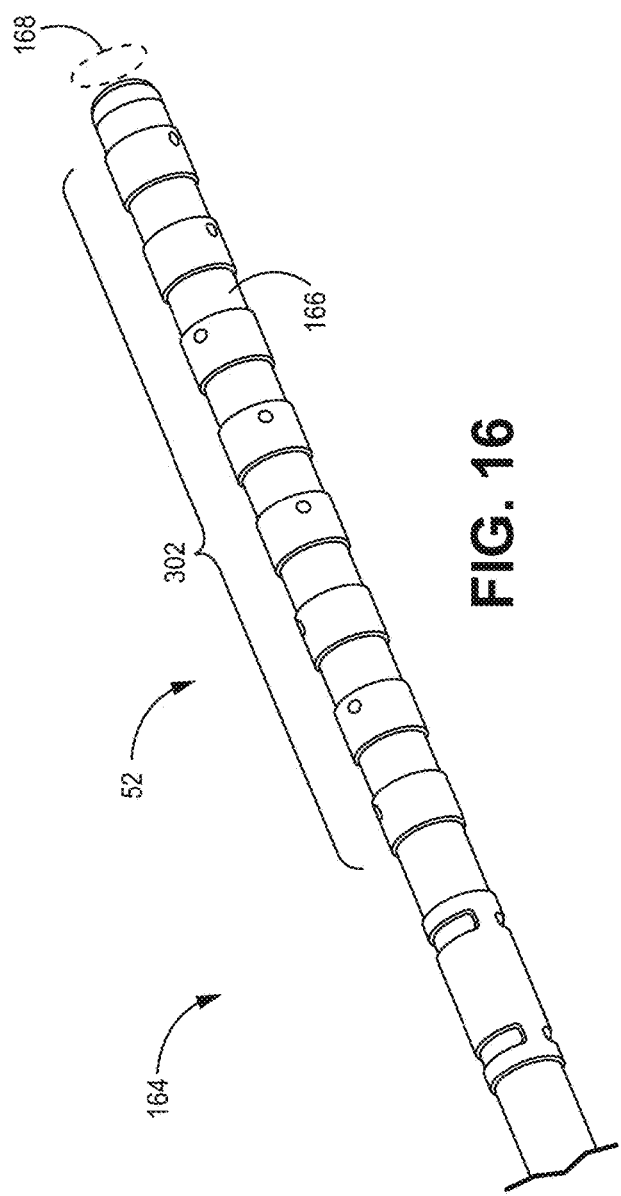
FIG. 16 is a conceptual diagram illustrating a proximal end of an example pre-grind preassembly.
Figure 17:
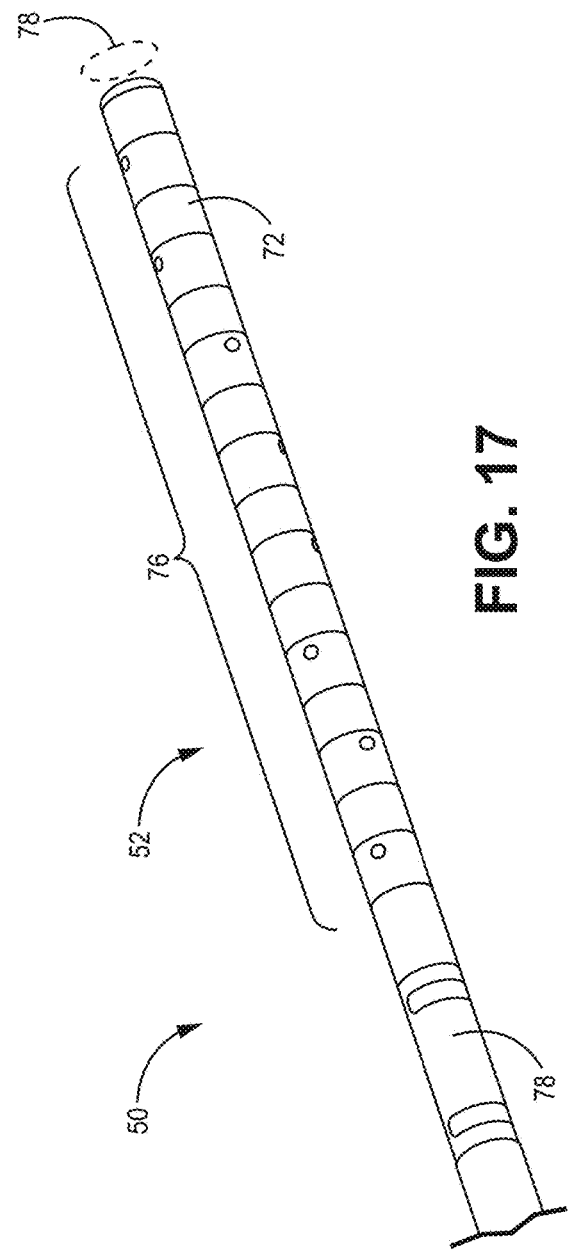
FIG. 17 is a conceptual diagram illustrating a proximal end of a lead.

FIGS. 15-17 illustrate formation of a plurality of terminals at a proximal end of a lead from terminal preforms. FIG. 15A is a conceptual diagram illustrating a proximal portion of an example preform preassembly 100 for medical lead 50. In the example of FIG. 15A, preassembly 100 includes a proximal end of preassembly 80 of FIG. 4B and a plurality of terminal preforms 302 positioned on preassembly 80. Each of the plurality of terminal preforms 302 may include electively conductive rings that are continuous at a radius from a center of the terminal segment that corresponds to an outer perimeter of lead 50, as further described in FIG. 15B. In preassembly 100, each of the plurality of terminal preforms 302 may correspond to terminal of the plurality of terminals 76 of lead 50 of FIG. 3. Preassembly 100 may also include a premold retention sleeve 304.

Each of the plurality of terminal preforms 302 may be formed from a continuous, electrically conductive terminal ring. Each conductive ring may be configured for use as a terminal, such as a terminal of the plurality of terminals 76 of FIG. 3. The conductive ring may be filled with an insulator portion. The insulator portion may be ground with channels configured to house either a conductor or a connection sleeve. The conductor channels may be configured to pass through conductors configured for coupling to proximal terminal preforms, while the connection channel may be configured to house a connection sleeve for coupling to a corresponding terminal preform.

FIG. 15B is a conceptual diagram illustrating a terminal preform 302. Terminal preform 302 includes a continuous terminal ring 312. Continuous terminal ring 312 is continuous at a radius corresponding to outer perimeter 78 of lead 50. Terminal preform 302 includes an insulator 310 that includes a connection channel 316 and a plurality of conductor channels 318. Connection channel 316 may be configured to house a connection sleeve of the plurality of proximal connection sleeves 86 of preassembly 80 of FIG. 4B. At least a portion of a wall of connection channel 316 may border continuous terminal ring 312. The plurality of conductor channels 318 may be configured to pass through a portion of the plurality of conductors 74 of preassembly 80 of FIG. 4B. The configuration of the plurality of conductor channels 318 and connection channel 316 may allow insulator portion 310 to act as both a conductor hub for connection sleeves that couple to proximal terminal preforms and a connection sleeve hub for a connection sleeve that couples to continuous terminal ring 312. Insulator portion 310 may be positioned around a lumen segment 314. Continuous terminal ring 312 may include a terminal hole 320 for coupling to another conductor, such as a contact of IMD 20.

FIG. 15C illustrates premold retention sleeve 304. Premold retention sleeve 304 may include a continuous sleeve 332 with one or more retention inlets 330 formed in continuous sleeve 332. The one or more retention inlets 330 may be configured to maintain alignment of preassemblies and leads during fabrication and attachment of the lead to an external device.

A preformed segment preassembly, such as preform preassembly 100 of FIG. 15A, may have an overmold applied to the preassembly. The overmold may join at least a portion of the terminal preforms and/or encase the preassembly to a substantially uniform perimeter. The resulting pre-grind preassembly may form a preassembly to be ground at a later time to form a medical lead, such as lead 50 of FIG. 3. FIG. 16 is a conceptual diagram illustrating proximal end 52 of pre-grind preassembly 164. As described in FIG. 6, preassembly 100 of FIG. 15A may have overmold layer 166 applied to preassembly 100 that joins the plurality of terminal preforms 302 into pre-grind preassembly 164. Pre-grind preassembly 164 may have a radius of outer perimeter 168 that is greater than a radius of outer perimeter 78 of lead 50. In the example of FIG. 16, a surface of pre-grind preassembly 164 may include surfaces of continuous terminal rings 312 from the plurality of terminal preforms 302. In some examples, overmold layer 166 may completely or partially cover terminal preforms 302.

An overmolded pre-grind assembly, such as pre-grind assembly 164 of FIG. 6, may be ground to a form of a medical lead, such as lead 50 of FIG. 3. FIG. 17 is a conceptual diagram illustrating proximal end 52 of lead 50. Material, including material from the conductive rings 312 of the plurality of terminal preforms 302 and overmold 166, may be removed so that pre-grind preassembly 164 having an outer perimeter 168 may be reduced to lead 50 having an outer perimeter 78. The proximal end 52 of the resulting lead 50 may include the plurality of terminals 76 and a retention sleeve 79.

Figure 18:
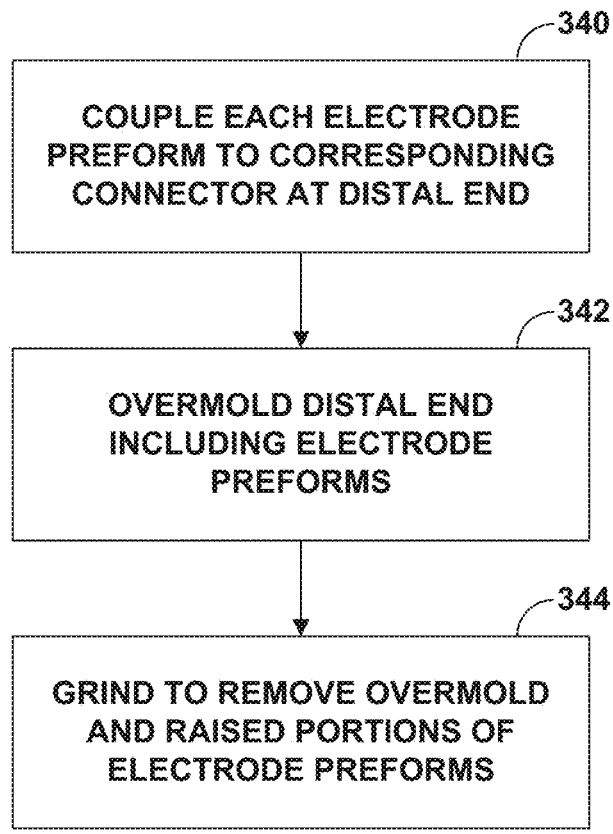
FIG. 18 is a flow diagram of an example technique for fabricating a medical lead.

FIG. 18 is a flow diagram of an example technique for fabricating a medical lead, such as medical lead 50 of FIG. 3. Reference may be made to lead 50 of FIGS. 3, 7, and 17, conductor preassembly 80 of FIGS. 4A and 4B, preform preassembly 100 of FIGS. 5A and 15A, and pre-grind preassembly 164 of FIGS. 6 and 16. However, the example technique of FIG. 18 may be used with a variety of leads and lead preassemblies.

The example technique may include coupling each electrode preform 102, 104, 106, 108, to a corresponding connection sleeve of the plurality of distal connection sleeves 84 at distal end 54 of conductor preassembly 80 (340). Distal connection sleeves 84 may be crimped onto an end of the conductors of the conductor preassembly. Before coupling the connection sleeve to the electrode preform, the electrode preform may be positioned so that the corresponding connection sleeve is in a connection channel of the electrode preform and conductors for distal electrode preforms are passed through conductor channels. The connection sleeve may be coupled to the electrode preform using any method that creates sustained electrical contact between a conductive ring of the electrode preform and the connection sleeve including, but not limited to, welding, soldering, and the like. In some examples, a connection sleeve may be coupled to a corresponding electrode preform after positioning of the electrode preform, while in other examples, two or more electrode preforms may be positioned before coupling the corresponding connection sleeves to the electrode preforms.

As an example, ring electrode preform 108 may be positioned on preassembly 80 at a first position. Electrode preform may have a connection sleeve in a connection channel and seven conductors in seven conductor channels. A heat source may be applied to an outer surface of ring electrode preform 108 proximate to the connection sleeve, so that the connection sleeve attaches to an inner wall of a conductive ring of ring electrode preform 108. A similar process may be sequentially performed for segmented electrode preforms 104 and 106 and ring electrode preform 102.

The example technique may also include coupling each terminal preform 302 to a corresponding connection sleeve of the plurality of proximal connection sleeves 86 at proximal end 52 of conductor preassembly 80. The terminal preforms 302 may be positioned and coupled as described for the electrode preforms above.

The example technique may include overmolding a distal end of preform preassembly 100 (342), as seen in FIG. 5A. Overmolding may include applying an overmold, such as a lead body material, to preform preassembly to form a pre-grind preassembly of a particular outer perimeter. The particular outer perimeter may correspond to an outer radius of electrode preforms 102, 104, 106, and 108, so that the resulting pre-grind preassembly has a substantially uniform outer perimeter. The applied overmold may join together components of the preform preassembly, including electrode preforms to other electrode preforms and conductors to conductor channels. In some examples, the applied overmold may join with insulator portions of the electrode preforms, such that lead body may be a monolithic body. Preform preassembly may be held by a mold. The mold may locate off, for example, the raised portions of electrode preforms 102, 104, 106, and 108 that extend to an outer diameter of preform preassembly 100. Preform preassembly 100 may be located in the center of the mold. The overmold may include a biocompatible polymer, such as 55D polyurethane. The polymer may be injected into the mold through side gates in between electrode preforms 102, 104, 106, and 108. The polymer may cure in the mold.

The example technique may also include overmolding a proximal end of preform preassembly 100, as seen in FIG. 15A. The proximal end of preform preassembly 100 may be overmolded as described for the distal end of preform preassembly 100 above. In some examples, the proximal end and the distal end may be overmolded at the same time, while in other examples, each end may be overmolded at different times.

The example technique may include grinding the pre-grind assembly to remove overmold and portions of electrode preforms and/or terminal preforms that have an outer perimeter greater than an outer perimeter of lead 50, such as raised portions of the electrode preforms (344). Raised portions of the conductive rings of segmented electrode preforms 104 and 106 may be ground off so that their conductive rings are no longer continuous. The resulting lead 50 may have circumferentially continuous portions of ring electrode preforms 102 and 108 that form ring electrodes 62 and 68, respectively, and circumferentially discontinuous portions of segmented electrode preforms 104 and 106 that form segmented electrode rings 64 and 66, respectively. Grinding the pre-grind preassembly may involve any technique that removes material from an outer perimeter of the pre-grind preassembly 164 to the outer perimeter of lead 50 including, but not limited to, centerless grinding, abrasive cutting, filing, and the like. For example, for centerless grinding, a center of pre-grind preassembly 164 may not be used as a reference; rather, a grinder may locate pre-grind preassembly 164 off the outer perimeter. Centerless grinding may allow for symmetrical and asymmetrical features of the resulting lead 50. After grinding, the resulting medical lead 50 may fit in a cannula or needle, which may have a particular inner diameter associated with an outer diameter of medical lead 50. In some examples, grinding may be configured to have a tolerance within 0.005 in. of a desired outer diameter, such as an outer diameter of medical lead 50 of 0.05 in.

Figure 19:
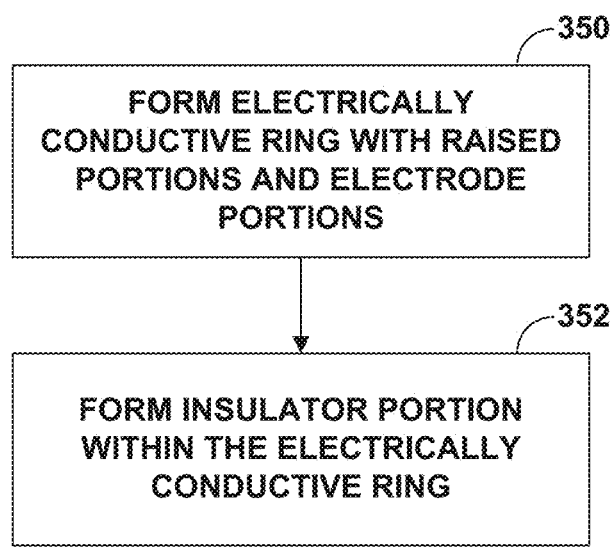
FIG. 19 is a flow diagram of an example technique for fabricating segmented electrode preforms for positioning on a conductor preassembly.

FIG. 19 is a flow diagram of an example technique for fabricating segmented electrode preforms for positioning on a conductor preassembly. Reference may be made to segmented electrode preforms 104 and 106 of FIGS. 5C and 5D. However, the example technique of FIG. 19 may be used with a variety of electrode and/or terminal preforms.

The example technique may include forming an electrically conductive ring 122, 142 with raised portions 134, 154 and electrode portions 136, 156 (350). Each raised portion 134, 154, may have an inner surface at a radius greater than a radius of an outer perimeter of the desired lead, such that grinding to the radius of the outer perimeter removes the raised portion and/or creates a discontinuity in the raised portion. Each electrode portion 136, 156, may have an inner surface at a radius less than the radius of the outer perimeter of the desired lead, such that grinding to the radius of the outer perimeter does not remove the electrode portion. The electrode portions 122, 142, may include electrode locking features 132, 152, at one or both ends of electrode portions 122, 142. Conductive rings 122, 142, may be formed using a variety of processes including, but not limited to, electrical discharge machining, molding, deposition, and other processes capable of fabricating small parts from electrically conductive materials.

The example technique may include forming an insulator portion 120, 140 within the electrically conductive ring (352). Each insulator portion 120, 140 may include one or more projections 130, 150 corresponding to one or more raised portions 134, 154. In some examples, a segment of lumen 124, 144, may be placed at a center of the conductive ring 122, 142, and the insulator portion 120, 140, may be formed around the segment of lumen 124, 144. In some examples, a polymer may be injection molded into conductive ring 122, 142, to form the insulator portion 120, 140.

The example technique may include forming conductor and connection channels (not shown). In some examples, connection channels 126, 146, and conductor channels 128, 148, may be formed during formation of the insulator portion 120, 140. For example, a mold form may include projections for connection channels 126, 146, and conductor channels 128, 148, around which insulator portion 120, 140, is formed. In some examples, connection channels 126, 146, and conductor channels 128, 148, may be formed after formation of insulator portion 120, 140. For example, holes may be drilled in the insulator portion 120, 140, to form connection channels 126, 146, and conductor channels 128, 148.

The above features and techniques are examples. Any suitable techniques may be used to fabricate the structures described herein and may vary based on the particular materials employed for the respective components.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided.

These examples may be combined in any permutation or combination. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Example 1. An assembly comprising: at least one electrode preform, the at least one electrode preform comprising: an electrically conductive ring; and an insulator portion within the electrically conductive ring, wherein the insulator portion includes at least one connection channel, and wherein at least a portion of the at least one connection channel is bounded by the electrically conductive ring.

Example 2. The assembly of Example 1, wherein the at least one electrode preform is a ring electrode preform, and wherein the electrically conductive ring includes at least one raised portion extending around a perimeter of the ring and at least one electrode portion.

Example 3. The assembly of Example 2, wherein the at least one raised portion includes two raised portions, each raised portion positioned on an axial edge of the electrically conductive ring.

Example 4. The assembly of Example 1, wherein the at least one electrode preform is a segmented electrode preform, wherein the electrically conductive ring includes a plurality of electrode portions and a plurality of raised portions, wherein the ring is configured such that respective electrode portions alternate with respective raised portions continuously around the ring, wherein each of the plurality of electrode portions is continuous at a radius from a center of the electrically conductive ring that corresponds to an outer perimeter of the medical lead, wherein the insulator portion has a plurality of projections extending into a respective raised portion of the ring radially outward of the radius from the center of the conductive ring that corresponds to the outer perimeter of the medical lead, and wherein the at least one connection channel includes a respective connection channel for each of the plurality of electrode portions.

Example 5. The assembly of Example 4, further comprising: a lead body that includes a distal end and a proximal end defining a longitudinal axis of the lead body; and a plurality of electrical conductors extending about the longitudinal axis of the lead body, wherein each respective electrode portion of the plurality of electrode portions is electrically coupled to a respective electrical conductor of the plurality of electrical conductors through a connection channel of the at least one connection channel.

Example 6. The assembly of Example 5, further comprising a plurality of terminal preforms, each terminal preform comprising an electrically conductive ring and an insulator portion within the electrically conductive ring, wherein the plurality of terminal preforms corresponds to at least the number of electrode portions, and wherein each respective electrically conductive ring is electrically coupled to a respective electrical conductor of the plurality of electrical conductors.

Example 7. The assembly of Example 5, further comprising at least one ring electrode preform comprising an electrically conductive ring and an insulator portion within the electrically conductive ring, wherein each respective electrically conductive ring of the at least one ring electrode preform is electrically coupled to a respective electrical conductor of the plurality of electrical conductors.

Example 8. The assembly of Example 5, wherein the insulator portion is a portion of the lead body.

Example 9. The assembly of Example 1, wherein the plurality of electrode portions comprises three electrode portions, and wherein the plurality of raised portions comprises three raised portions.

Example 10. A method of making a preformed segment for a medical lead, the method comprising: forming an electrically conductive ring; and forming an insulator portion within the electrically conductive ring, wherein the insulator portion includes a plurality of channels, and wherein at least a portion of each channel of the plurality of channels is bounded by the electrically conductive ring.

Example 11. The method of Example 10, further comprising grinding the plurality of channels into the insulator portion.

Example 12. The method of Example 10, wherein the electrically conductive ring includes a plurality of electrode portions and a plurality of raised portions defining an outer perimeter of the ring, wherein the ring is configured such that respective electrode portions alternate with respective raised portions continuously around the outer perimeter of the ring.

Example 13. The method of Example 12, wherein the insulator portion has a plurality of projections extending into a respective raised portion of the ring radially outward of the radius from the center of the conductive ring that corresponds to the outer perimeter of the medical lead, and wherein the at least one connection channel includes a respective connection channel for each of the plurality of electrode portions.

Example 14. The method of Example 10, wherein the electrically conductive ring includes at least one raised portion extending around a perimeter of the ring and at least one electrode portion.

Example 15. The assembly of Example 10, wherein the at least one raised portion includes two raised portions, each raised portion positioned on an axial edge of the electrically conductive ring.

Example 16. The assembly of Example 12, wherein the plurality of electrode portions comprises three electrode portions, and wherein the plurality of raised portions comprises three raised portions.

Example 17. A method of making a medical lead, the method comprising: positioning at least one segmented electrode preform on an assembly, wherein the assembly includes a lead body and a plurality of electrical conductors, wherein the lead body includes a distal end and a proximal end defining a longitudinal axis of the lead body, wherein the plurality of electrical conductors extends about the longitudinal axis of the lead body, wherein each electrical conductor has a conductor body and a distal connection sleeve, wherein the at least one segmented electrode preform is positioned around at least a portion of the plurality of electrical conductors at the distal end, wherein the segmented electrode preform includes an electrically conductive ring and an insulator portion within the electrically conductive ring, wherein the ring is configured such that respective electrode portions alternate with respective raised portions continuously around the ring, and wherein each of the plurality of electrode portions is continuous at a radius from the longitudinal axis corresponding to an outer perimeter of the medical lead, and wherein the insulator portion has a plurality of projections each extending into a respective raised portion of the ring beyond the radius from the longitudinal axis corresponding to the outer perimeter of the medical lead, and wherein the insulator portion includes at least one channel; electrically coupling an electrode portion of the segmented electrode preform to the distal connection sleeve of a corresponding electrical conductor; forming an overmold on at least the segmented electrode preform; and grinding the segmented electrode preform to the outer perimeter.

Example 18. The method of Example 17, wherein each electrical conductor has a proximal connection sleeve, and further comprising: positioning at least one terminal preform around at least a portion of the plurality of electrical conductors at the proximal end, wherein the terminal preform includes an electrically conductive ring and an insulator portion within the electrically conductive ring, wherein the insulator portion includes at least one channel; and electrically coupling the electrically conductive ring of the at least one terminal preform to the proximal connection sleeve of a corresponding electrical conductor.

Example 19. The method of Example 17, further comprising: positioning at least one ring electrode preform around at least a portion of the plurality of electrical conductors at the distal end, wherein the ring electrode preform includes an electrically conductive ring and an insulator portion within the electrically conductive ring, wherein the insulator portion includes at least one channel, and wherein the electrically conductive ring includes at least one raised portion extending around a perimeter of the ring and at least one electrode portion; electrically coupling the electrically conductive ring of the at least one ring electrode preform to the distal connection sleeve of a corresponding electrical conductor; forming the overmold on at least the ring electrode preform; and grinding the segmented electrode preform to the outer perimeter.

Example 20. The method of Example 17, wherein grinding the segmented electrode preform comprises centerless grinding.

Example 21. A medical lead system comprising: a lead body including a distal end and a proximal end defining a longitudinal axis of the lead body; a plurality of electrical conductors extending about the longitudinal axis of the lead body; a plurality of electrodes positioned around an outer perimeter of the lead body, an inner surface of each of the plurality of electrodes defining an inner perimeter, wherein each respective electrode of the plurality of electrodes is electrically coupled to a respective electrical conductor of the plurality of electrical conductors, and wherein each electrode of the plurality of electrodes includes at least one electrode locking feature extending into the lead body from the inner perimeter.

Example 22. The medical lead system of Example 21, wherein the at least one electrode locking feature has: a base at the inner perimeter and an end at a radially inward tip, a length defined from the base to the end, and an angle defined by a centerline and a tangent of the inner perimeter at the centerline, wherein the centerline is a line from a center of the base to a center of the end.

Example 23. The medical lead system of Example 22, wherein the length is greater than 0.005 inches.

Example 24. The medical lead system of Example 22, wherein the length is greater than at least 30% of a radius of the inner perimeter.

Example 25. The medical lead system of Example 22, wherein the angle is less than 120 degrees.

Example 26. The medical lead system of Example 25, wherein the angle is between 30 degrees and 90 degrees.

Example 27. The medical lead system of Example 21, wherein the at least one electrode locking feature has at least one of a bulbous shape, an undercut shape, and a t-shape.

Example 28. The medical lead system of Example 22, wherein the at least one electrode locking feature has a stem between the base and the end, and wherein a width of the radially inward tip is greater than a width of the stem.

Example 29. The medical lead system of Example 21, wherein the at least one electrode locking feature comprises: a first electrode locking feature having a base at the inner perimeter and an end at a first tip; and a second electrode locking feature having a base at the inner perimeter and an end at a second tip, wherein a distance between the first tip and the second tip is less than a diameter of an electrical conductor of the plurality of electrical conductors.

Example 30. The medical lead system of Example 21, wherein at least one of the electrodes of the plurality of electrodes is electrically coupled to the respective electrical conductor of the plurality of electrical conductors at the at least one electrode locking feature.

Example 30A. The medical lead system of Example 21, wherein multiple ones of the plurality of electrodes are segmented electrodes.

Example 31. A method of making a medical lead, the method comprising: positioning at least one segmented electrode preform on an assembly, wherein the assembly includes a lead body and a plurality of electrical conductors, wherein the lead body includes a distal end and a proximal end defining a longitudinal axis of the lead body, wherein the plurality of electrical conductors extends about the longitudinal axis of the lead body, wherein each electrical conductor has a conductor body and a distal connection sleeve, wherein the at least one segmented electrode preform is positioned around at least a portion of the plurality of electrical conductors at the distal end, wherein the segmented electrode preform includes an electrically conductive ring and an insulator portion within the electrically conductive ring, wherein the electrically conductive ring includes at least one electrode locking feature extending into the lead body from the inner perimeter, and wherein the insulator portion includes at least one channel; and electrically coupling an electrode portion of the segmented electrode preform to the distal connection sleeve of a corresponding electrical conductor.

Example 32. The method of Example 31, wherein the ring is configured such that respective electrode portions alternate with respective raised portions continuously around the ring, and wherein each of the plurality of electrode portions is continuous at a radius from the longitudinal axis corresponding to an outer perimeter of the medical lead, and wherein the insulator portion has a plurality of projections each extending into a respective raised portion of the ring beyond the radius from the longitudinal axis corresponding to the outer perimeter of the medical lead, and further comprising: forming an overmold on at least the segmented electrode preform; and grinding the segmented electrode preform to the outer perimeter.

Example 33. The method of Example 31, wherein the at least one electrode locking feature has: a base at the inner perimeter and an end at a radially inward tip, a length defined from the base to the end, and an angle defined by a centerline and a tangent of the inner perimeter at the centerline, wherein the centerline is a line from a center of the base to a center of the end.

Example 34. The method of Example 33, wherein the length is greater than 0.005 inches.

Example 35. The method of Example 33, wherein the length is greater than at least 30% of a radius of the inner perimeter.

Example 36. The method of Example 33, wherein the angle is less than 120 degrees.

Example 37. The method of Example 36, wherein the angle is between 30 degrees and 90 degrees.

Example 38. The method of Example 31, wherein the at least one electrode locking feature has at least one of a bulbous shape, an undercut shape, and a t-shape.

Example 39. The method of Example 33, wherein the at least one electrode locking feature has a stem between the base and the end, and wherein a width of the radially inward tip is greater than a width of the stem.

Example 40. The method of Example 31, wherein at least one of the electrodes of the plurality of electrodes is electrically coupled to the respective electrical conductor of the plurality of electrical conductors at the at least one electrode locking feature.

Example 40A. The method of Example 31, wherein multiple ones of the plurality of electrodes are segmented electrodes.

Example 41. A medical lead system comprising: a lead body including a distal end and a proximal end defining a longitudinal axis of the lead body; a plurality of electrical conductors extending about the longitudinal axis of the lead body; a plurality of electrodes positioned around an outer perimeter of the lead body the outer perimeter defining a circumferential plane, wherein each respective electrode of the plurality of electrodes is electrically coupled to a respective electrical conductor of the plurality of electrical conductors, and wherein each electrode of the plurality of electrodes has a circumferential perimeter that includes a curved portion having a radius of a curve of the curved portion.

Example 42. The medical lead system of Example 41, wherein the radius of the curve is greater than 0.001 inches.

Example 43. The medical lead system of Example 41, wherein each electrode of the plurality of electrodes has a length and width in the circumferential plane, and wherein the radius of the curve is greater than one tenth of the lesser of the length and the width of the respective electrode.

Example 44. The medical lead system of Example 41, wherein each electrode of the plurality of electrodes has a length and a width in the circumferential plane, and wherein each electrode has a surface area that is five percent less than a surface area of a square having the length and the width of the respective electrode.

Example 45. The medical lead system of Example 41, wherein the circumferential perimeter has an oval shape.

Example 46. The medical lead system of Example 41, wherein the plurality of electrodes comprises a plurality of segmented electrodes.

Example 47. The medical lead system of Example 46, wherein the plurality of electrodes comprises at least six segmented electrodes.

Example 48. The medical lead system of Example 44, wherein the surface area is ten percent less than the surface area of the square having the length and the width of the respective electrode.

Example 49. The medical lead system of Example 43, wherein the radius of the curve is greater than 25% of the lesser of the length and the width of the respective electrode.

Example 50. The medical lead system of Example 42, wherein the radius of the curve is greater than 0.005 inches.

Example 51. A method of making a medical lead, the method comprising: positioning at least one electrode preform on an assembly, wherein the assembly includes a lead body and a plurality of electrical conductors, wherein the lead body includes a distal end and a proximal end defining a longitudinal axis of the lead body, wherein the plurality of electrical conductors extends about the longitudinal axis of the lead body, wherein each electrical conductor has a conductor body and a distal connection sleeve, wherein the at least one electrode preform is positioned around at least a portion of the plurality of electrical conductors at the distal end, wherein the at least one electrode preform includes an electrically conductive ring and an insulator portion within the electrically conductive ring, and wherein the insulator portion includes at least one channel; electrically coupling an electrode portion of the at least one electrode preform to the distal connection sleeve of a corresponding electrical conductor; forming an overmold on at least the electrode preform; and grinding the electrode preform to the outer perimeter to form a plurality of electrodes defining a circumferential plane, wherein each electrode of the plurality of electrodes has a circumferential perimeter that includes a curved portion having a radius of a curve of the curved portion.

Example 52. The method of Example 51, wherein the radius of the curve is greater than 0.001 inches.

Example 53. The method of Example 51, wherein each electrode of the plurality of electrodes has a length and width in the circumferential plane, and wherein the radius of the curve is greater than one tenth of the lesser of the length and the width of the respective electrode.

Example 54. The method of Example 51, wherein each electrode of the plurality of electrodes has a length and a width in the circumferential plane, and wherein each electrode has a surface area that is five percent less than a surface area of a square having the length and the width of the respective electrode.

Example 55. The method of Example 51, wherein the circumferential perimeter has an oval shape.

Example 56. The method of Example 51, wherein the plurality of electrodes comprises a plurality of segmented electrodes.

Example 57. The method of Example 56, wherein the plurality of electrodes comprises at least six segmented electrodes.

Example 58. The method of Example 54, wherein the surface area is ten percent less than the surface area of the square having the length and the width of the respective electrode.

Example 59. The method of Example 53, wherein the radius of the curve is greater than 25% of the lesser of the length and the width of the respective electrode.

Example 60. The method of Example 52, wherein the radius of the curve is greater than 0.005 inches.

Example 61. A medical lead system comprising: a lead body including a distal end and a proximal end defining a longitudinal axis of the lead body; a plurality of electrical conductors extending about the longitudinal axis of the lead body, each electrical conductor having a conductor body and a distal connection portion; a plurality of electrodes positioned around an outer perimeter of the distal end of the lead body, wherein each respective electrode of the plurality of electrodes is electrically coupled to the distal connection portion of a respective electrical conductor of the plurality of electrical conductors, wherein the lead body includes a plurality of conductor channels and a plurality of connector channels, wherein the conductor body of each electrical conductor extends through at least one conductor channel of the plurality of conductor channels and the distal connection portion of each electrical conductor is positioned in a connection channel of the plurality of connection channels, and wherein a diameter of the conductor channel is greater than or equal to a diameter of the connection channel of a respective electrical conductor of the plurality of electrical conductors.

Example 62. The medical lead system of Example 61, wherein a diameter of the conductor body of each electrical conductor of the plurality of electrical conductors is greater than or equal to a diameter of the distal connection portion of each electrical conductor of the plurality of electrical conductors.

Example 63. The medical lead system of Example 61, further comprising: a plurality of terminals positioned around an outer perimeter of the proximal end of the lead body, wherein each electrical conductor of the plurality of electrical conductors further includes a proximal connection portion, wherein each respective terminal of the plurality of terminals is electrically coupled to the proximal connection portion of a respective electrical conductor of the plurality of electrical conductors, and wherein the proximal connection portion of each electrical conductor is positioned in a connection channel.

Example 64. The medical lead system of Example 61, wherein each distal connection portion includes a connection sleeve.

Example 65. The medical lead system of Example 64, wherein the connection sleeve includes a 90/10 platinum/iridium alloy.

Example 66. The medical lead system of Example 62, wherein the diameter of the conductor body of each electrical conductor of the plurality of electrical conductors is substantially equal to the diameter of the distal connection portion of each electrical conductor of the plurality of electrical conductors.

Experimental Results

Current density for a variety of segmented electrode shapes was determined. A model of a medical lead was constructed in the finite-element analysis software COMSOL Multiphysics (v.4.3). The design of the electrodes was parameterized such that the parameter 'fillet radius' controlled the curvature of the edges on the electrodes. The medical lead was positioned in a large cylindrical volume conductor (200 m tall×100 mm radius) with conductivity of 0.285 S/m. A single segmented electrode was set to be a voltage source delivering −1V. The walls of the volume conductor were set to ground. The model was meshed using a prefined 'extra fine' setting which yielded 546299 tetrahedral elements. The static electric field solution was computed using a stationary solver. 500 contours were placed on the surface of the cathode electrode to evaluate the surface current density (units: $A/m^2$). The current density values on the contours were exported into Matlab to compute summary statistics such as maximum, mean and standard deviation. This entire process was done programmatically so as to iterate through different fillet radius values.

FIGS. 20-25 are example diagrams and current density maps of electrodes having a variety edge designs. Each current density map may indicate a spatial distribution of current density of an electrode. Units of an x-axis and a first y-axis of each of FIGS. 20-25 are in mm, while units of a second y-axis of FIGS. 20B-25B are in amperes per meter squared ($A/m^2$). For unlabeled axes, such as FIGS. 22A and 23A, it is understood that dimensions correspond to FIGS. 22B and 23B, respectively.

Figure 20A:
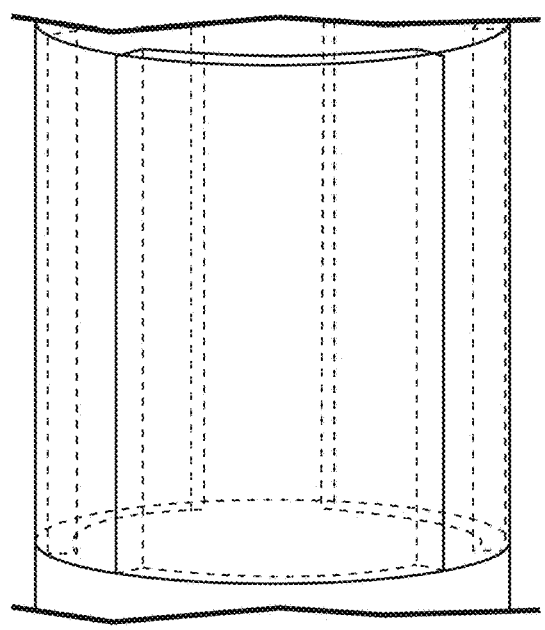
FIG. 20A is a conceptual diagram illustrating an example segmented electrode having squared corners.
Figure 20B:
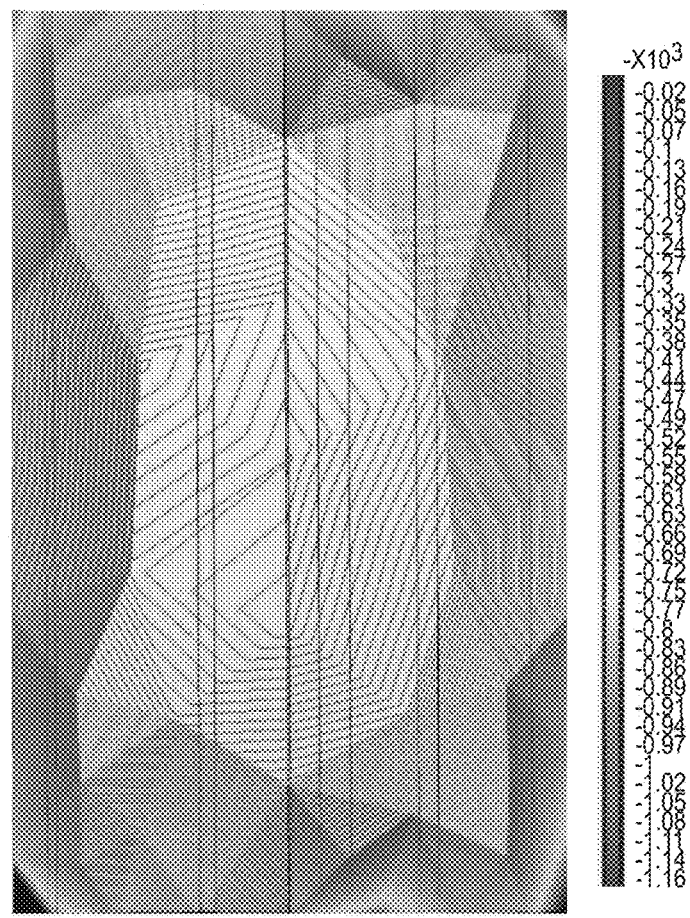
FIG. 20B is a current density map for the example segmented electrode of FIG. 20A.

FIG. 20A is a conceptual diagram illustrating an example segmented electrode having squared corners and a surface area of 1.515 $mm^2$. FIG. 20B is a current density map of charge density for the example segmented electrode of FIG. 20A. As seen in FIG. 20B, current density is significantly higher at each squared corner than along each edge of the electrode.

Figure 21A:
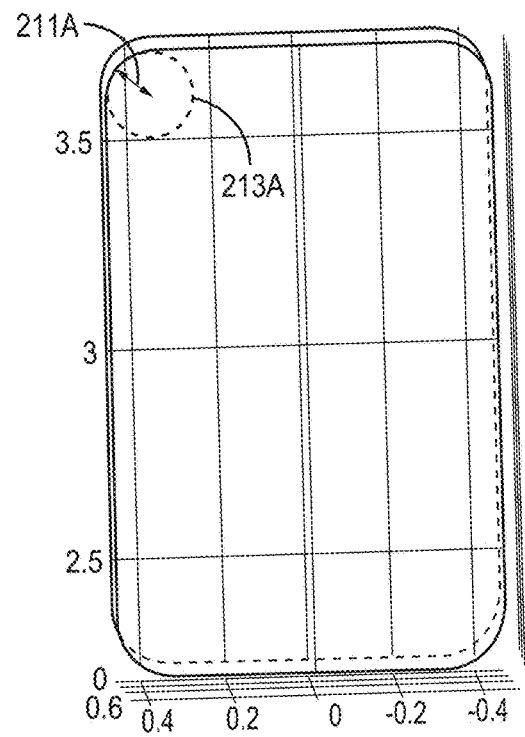
FIG. 21A is a conceptual diagram illustrating an example segmented electrode having rounded corners.
Figure 21B:
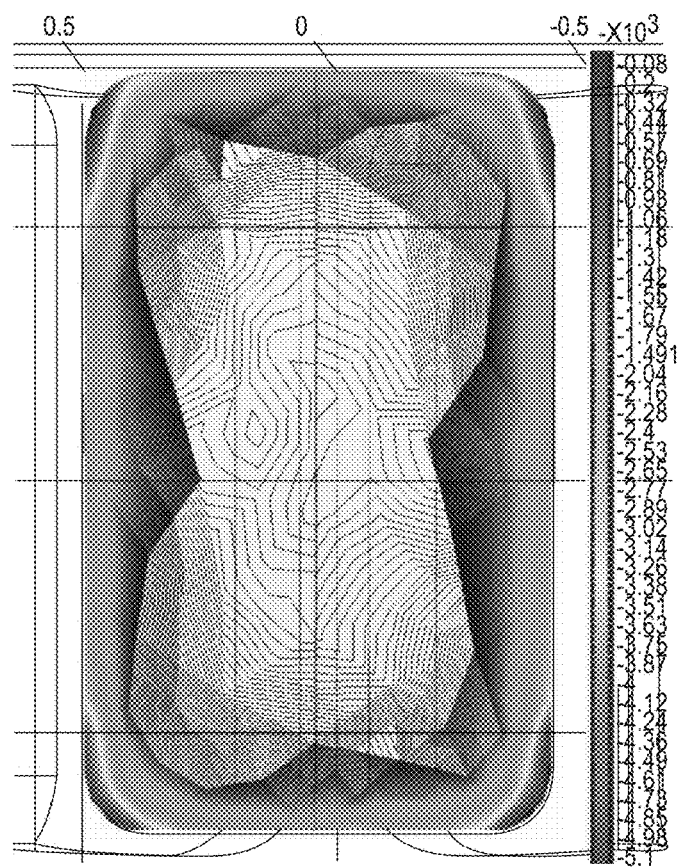
FIG. 21B is a current density map for the example segmented electrode of FIG. 21A.

FIG. 21A is a conceptual diagram illustrating an example segmented electrode having rounded corners (e.g., "curved portion") and surface area of 1.463 $mm^2$. The example segmented electrode of FIG. 21A has a curve 213A having a radius 211A. In this example, radius 211A may be approximately 0.125 mm, or greater than 10% of a length of the example segmented electrode. FIG. 21B is a current density map of charge density for the example segmented electrode of FIG. 21A. As seen in FIG. 21B, current density is more even around the edges of the electrode than with the squared corners of FIG. 20B.

Figure 22A:
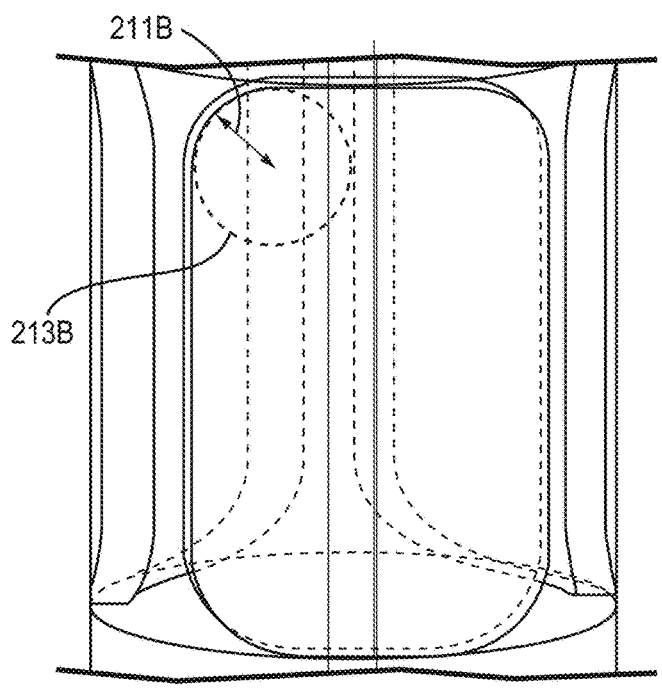
FIG. 22A is a conceptual diagram illustrating an example segmented electrode having rounded corners at a greater radius than the segmented electrode of FIG. 21A.
Figure 22B:
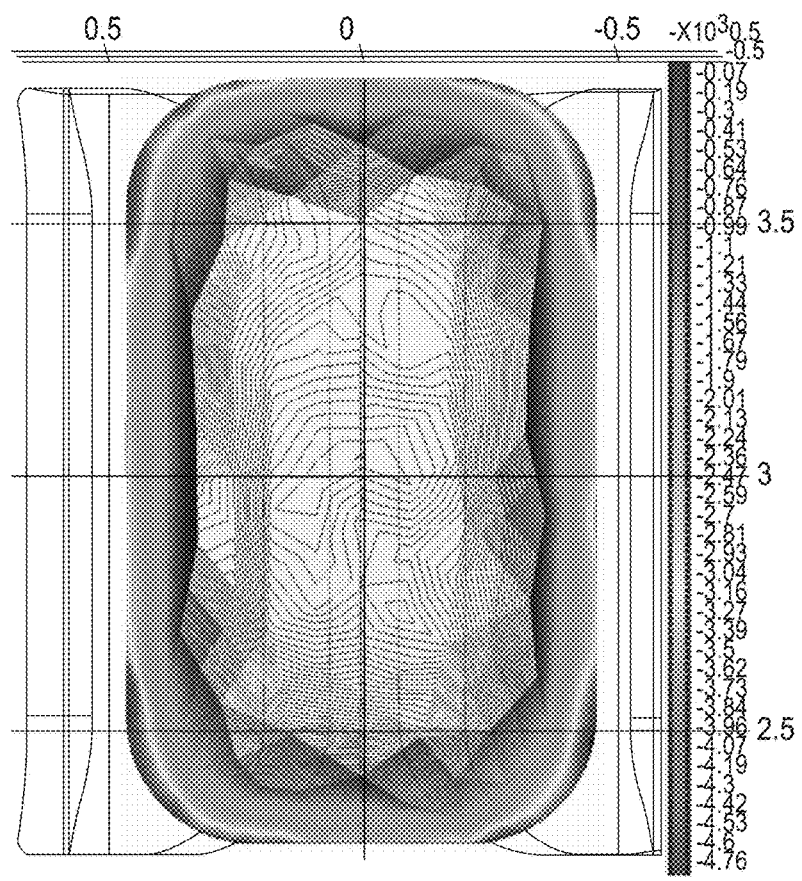
FIG. 22B is a current density map for the example segmented electrode of FIG. 22A.

FIG. 22A is a conceptual diagram illustrating an example segmented electrode having rounded corners at a greater radius than FIG. 21A and a surface area of 1.443 $mm^2$ (e.g., about 5% less than the surface area of FIG. 20A). The example segmented electrode of FIG. 22A has a curve 213B having a radius 211B that is larger than radius 211A. In this example, radius 211B may be approximately 0.25 mm, or greater than 25% of a length of the example segmented electrode. FIG. 22B is a current density map of charge density for the example segmented electrode of FIG. 22A. As seen in FIG. 22B, current density is more even around edges of the electrode than with the lower-radius rounded corners of FIG. 21B.

Figure 23A:
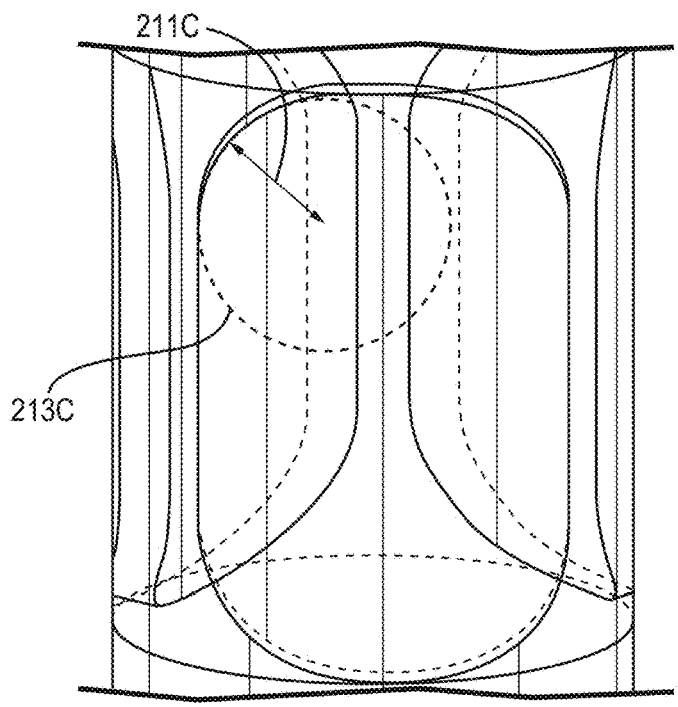
FIG. 23A is a conceptual diagram illustrating an example segmented electrode having rounded corners at a greater radius than the segmented electrodes of FIGS. 21A and 22A.
Figure 23B:
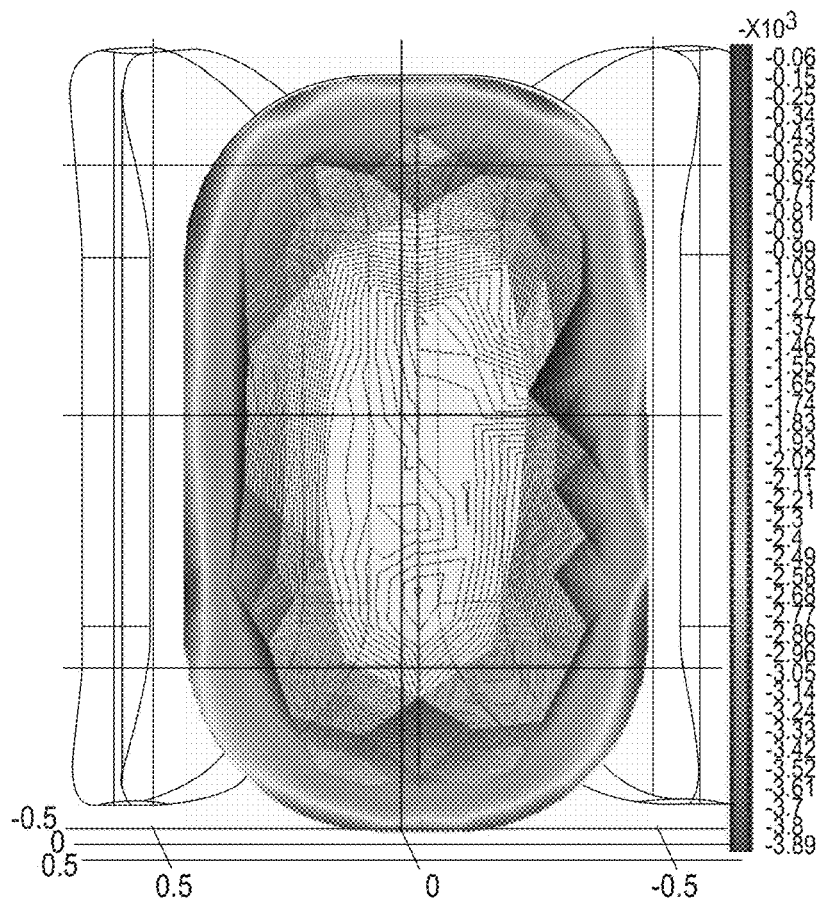
FIG. 23B is a current density map for the example segmented electrode of FIG. 23A.

FIG. 23A is a conceptual diagram illustrating an example segmented electrode having rounded corners at a greater radius than FIGS. 21A and 22A and a surface area of 1.358 $mm^2$. The example segmented electrode of FIG. 23A has a curve 213C having a radius 211C that is larger than radius 211A and radius 211B. In this example, radius 211B may be approximately 0.375 mm, or greater than 35% of a length of the example segmented electrode. FIG. 23B is a current density map of charge density for the example segmented electrode of FIG. 23A. As seen in FIG. 23B, current density is more even around edges of the electrode than with the lower-radius rounded corners of FIGS. 21B and 22B.

Figure 24A:
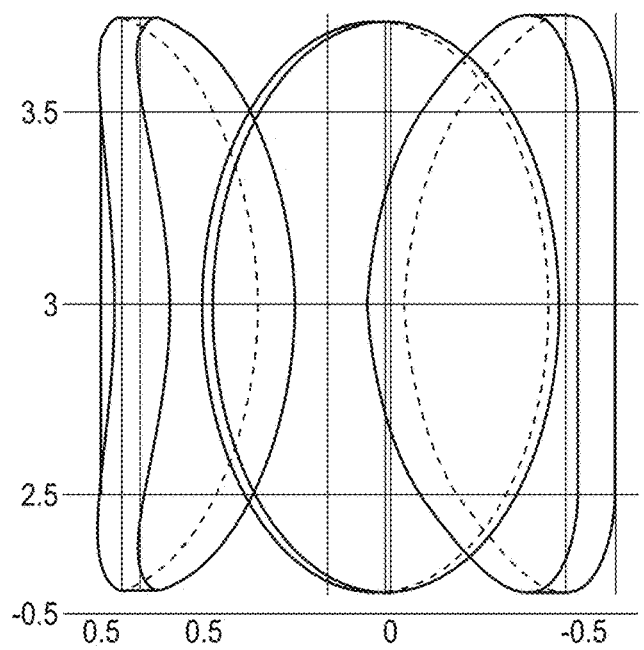
FIG. 24A is a conceptual diagram illustrating an example segmented electrode having an oval shape.
Figure 24B:
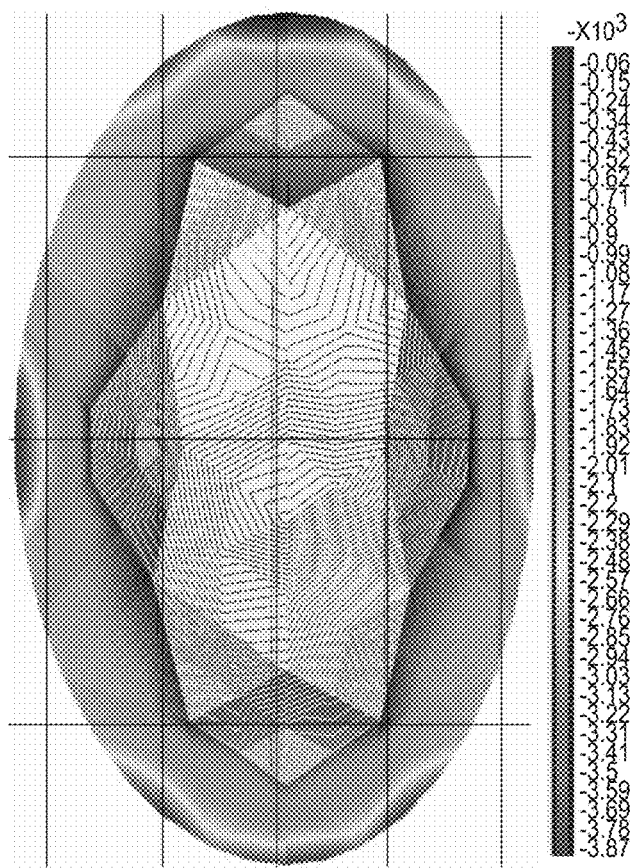
FIG. 24B is a current density map for the example segmented electrode of FIG. 24A.

FIG. 24A is a conceptual diagram illustrating an example segmented electrode having an oval shape and a surface area of 1.146 $mm^2$. FIG. 24B is a current density map of charge density for the example segmented electrode of FIG. 24A. As seen in FIG. 24B, current density is more even around the edges of the electrode than with the lower-radius rounded corners of FIGS. 21B, 22B, and 23B.

Figure 25A:
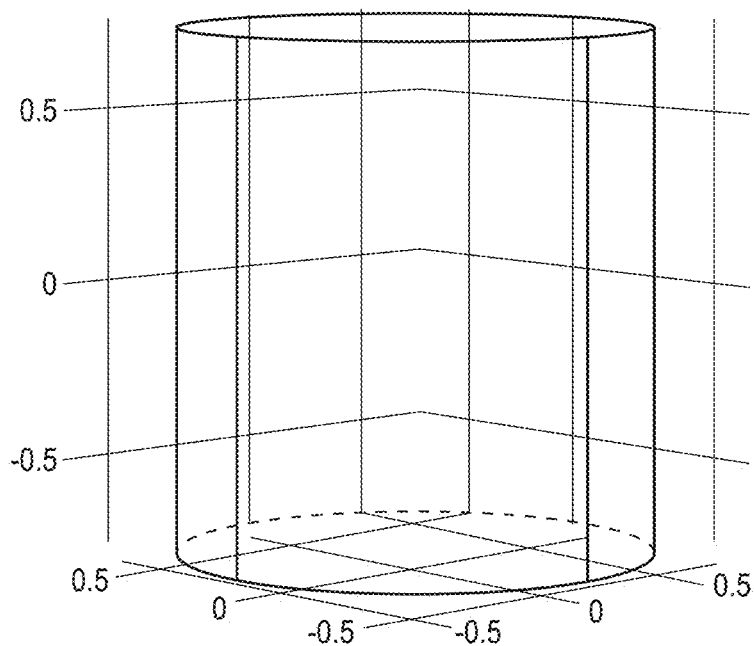
FIG. 25A is a conceptual diagram illustrating an example ring electrode having a cylindrical shape.
Figure 25B:
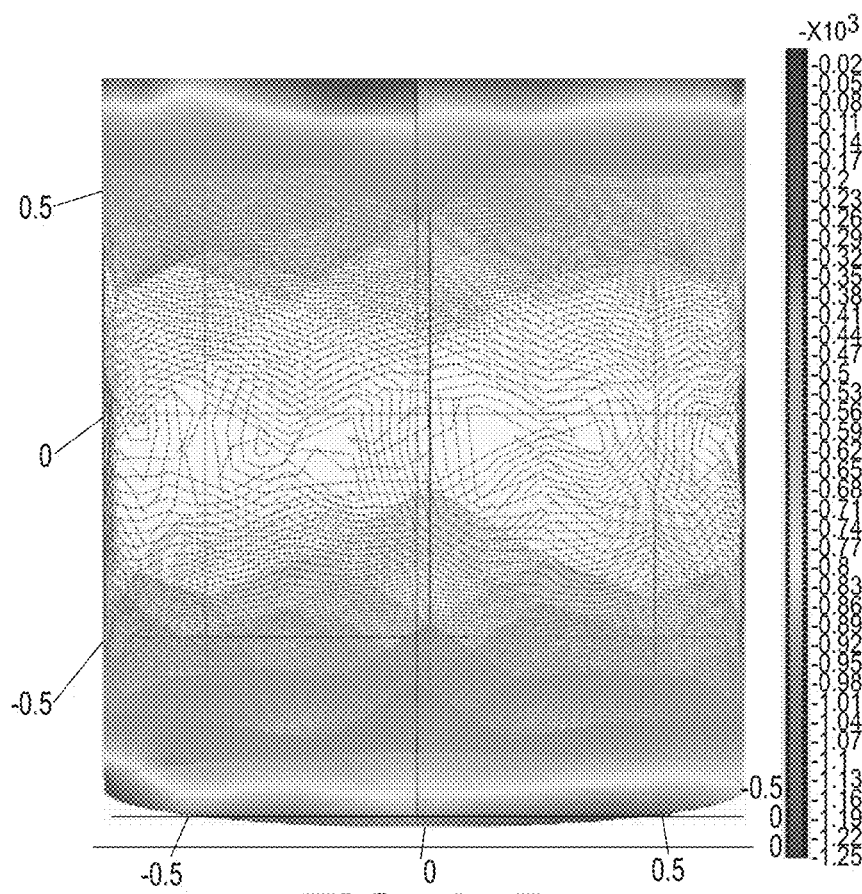
FIG. 25B is a current density map for the example ring electrode of FIG. 25A.

FIG. 25A is a conceptual diagram illustrating an example ring electrode having a cylindrical shape. FIG. 25B is a current density map of charge density for the example ring electrode of FIG. 25A. As seen in FIG. 25B, current density is highest at the edges of the ring electrode.

Figure 26A:
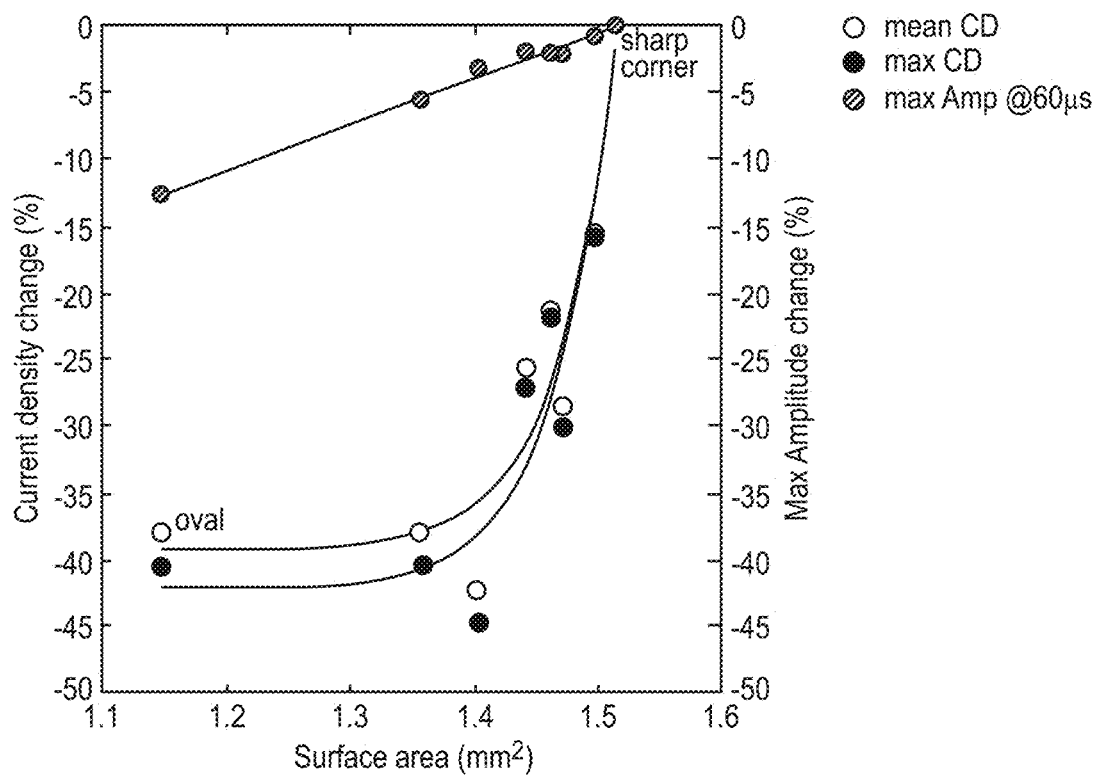
FIG. 26A is a graph of changes in current density and max amplitude from a normalized square corner electrode for various electrode surface areas.
Figure 26B:
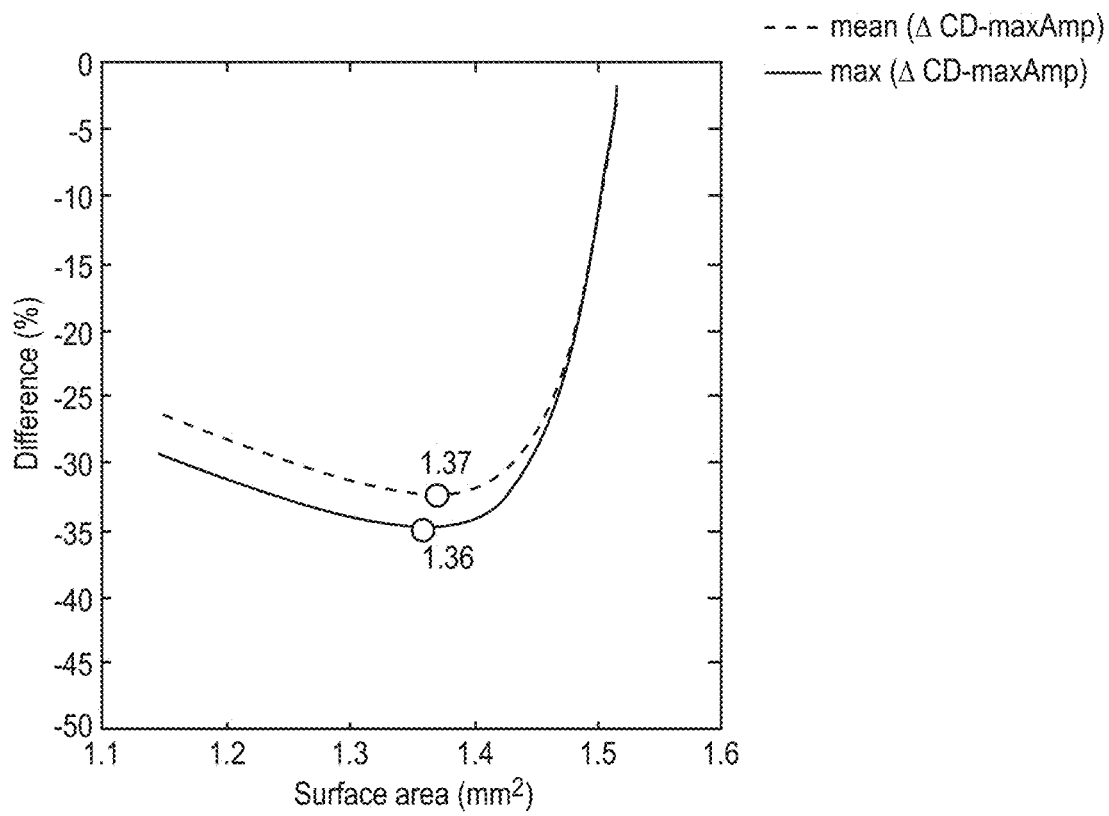
FIG. 26B is a graph of difference in changes in current density and amplitude with surface area.

FIG. 26A is a graph of changes in current density (%) and max amplitude (%) for various electrode surface areas (mm²), where a greater electrode surface area corresponds to a less rounded corner/edge. In the graph of FIG. 26A, a greater negative change in current density and/or max amplitude may indicate a more even current density distribution. As seen in FIG. 26A, as surface area decreases, corresponding to a greater radius of a corner, the negative change in current density and/or max amplitude increase. FIG. 26B is a graph of difference in changes in current density (%) and amplitude with surface area (mm²). As seen in the graph, a reduced current density may be established for a particular radius of corner/edge.

Various aspects of the disclosure have been described. These and other aspects are within the scope of the following claims.

What is claimed is:

1. A medical lead system comprising:
    a lead body including a distal end and a proximal end defining a longitudinal axis of the lead body, wherein the lead body comprises:
        two or more preforms, wherein each preform includes one or more insulator portions and a lumen segment within the one or more insulator portions; and
        an overmold between and adhered to the one or more insulator portions and the lumen segment of each preform of the two or more preforms;
    a plurality of electrical conductors extending about the longitudinal axis of the lead body;
    a plurality of segmented electrodes positioned around an outer perimeter of the lead body,
    wherein each respective electrode of the plurality of segmented electrodes is electrically coupled to a respective electrical conductor of the plurality of electrical conductors,
    wherein each segmented electrode of the plurality of segmented electrodes includes an outer curved surface defined by a perimeter that includes a curved portion having a radius of a curve of the curved portion,
    wherein the plurality of segmented electrodes comprise one or more sets of segmented electrodes,
    wherein each set of segmented electrodes includes two or more segmented electrodes secured to a respective insulator portion of the one or more insulator portions of the lead body, and
    wherein the overmold defines at least one machined surface region formed by grinding at least a portion of the overmold.

2. The medical lead system of claim 1,
    wherein the outer curved surface of each respective segmented electrode of the plurality of segmented electrodes has a length and width, and
    wherein the radius of the curve of a respective segmented electrode is greater than one tenth of the lesser of the length and the width of the respective segmented electrode.

3. The medical lead system of claim 2, wherein the radius of the curve of the respective segmented electrode is greater than 25% of the lesser of the length and the width of the respective segmented electrode.

4. The medical lead system of claim 1,
    wherein the outer curved surface of each respective segmented electrode of the plurality of segmented electrodes has a length and a width, and
    wherein a respective segmented electrode has a surface area that is five percent less than a surface area of an outer curved surface of a square perimeter electrode having the length and the width of the respective segmented electrode.

5. The medical lead system of claim 4, wherein the surface area of the outer curved surface of the respective segmented electrode is ten percent less than the surface area of the outer curved surface of the square perimeter electrode having the length and the width of the respective electrode.

6. The medical lead system of claim 1, wherein the radius of the curve is greater than 0.001 inches.

7. The medical lead system of claim 1,
    wherein the outer curved surface of each segmented electrode of the plurality of electrodes has a length and a width, and
    wherein a respective segmented electrode, in response to receiving an electrical current, is configured to produce a maximum current density that is at least 25 percent less than a maximum current density of a square perimeter electrode having the length and the width of the respective segmented electrode.

8. The medical lead system of claim 1, wherein a surface area of the outer curved surface of each segmented electrode of the plurality of segmented electrodes is between 1.3 and 1.45 square millimeters (mm²).

9. The medical lead system of claim 1, wherein the perimeter of the outer curved surface of each segmented electrode of the plurality of segmented electrodes has an oval shape.

10. The medical lead system of claim 1, wherein a center of each set of segmented electrodes is positioned at a substantially same longitudinal position along the longitudinal axis of the lead body.

11. The medical lead system of claim 1,
    wherein the outer curved surface of each respective segmented electrode of the plurality of segmented electrodes has a length and a width, and
    wherein a respective segmented electrode has a surface area that from five percent to twenty percent less than a surface area of an outer curved surface of a square perimeter electrode having the length and the width of the respective segmented electrode.

12. The medical lead system of claim 1, wherein each set of segmented electrodes is formed from a corresponding preform of the two or more preforms that includes the two or more segmented electrodes.

13. The medical lead system of claim 1, wherein a respective insulator portion includes one or more channels, each channel housing one electrical conductor of the plurality of electrical conductors.

14. A method of making a medical lead, the method comprising:
    positioning at least two segmented electrode preforms on an assembly, wherein the assembly includes a lead body and a plurality of electrical conductors, wherein the lead body includes a distal end and a proximal end defining a longitudinal axis of the lead body, wherein the plurality of electrical conductors extends about the longitudinal axis of the lead body, wherein each electrical conductor has a conductor body and a distal connection sleeve, wherein the at least two segmented electrode preforms are positioned around at least a portion of the plurality of electrical conductors at the distal end, wherein each of the at least two segmented electrode preforms includes an electrically conductive ring, an insulator portion within the electrically conductive ring, and a lumen segment within the insulator portion, and wherein the insulator portion includes at least one channel;

electrically coupling an electrode portion of the at least one segmented electrode preform to the distal connection sleeve of a corresponding electrical conductor;

forming an overmold on and between each of the at least two segmented electrode preforms, wherein the overmold adheres to the insulator portion and the lumen segment of each of the at least two segmented electrode preforms; and grinding each of the at least two segmented electrode preforms and at least a portion of the overmold to an outer perimeter to form a plurality of segmented electrodes and to define at least one machined surface region of the overmold, wherein an outer curved surface of each segmented electrode of the plurality of segmented electrodes has a perimeter that includes a curved portion having a radius of a curve of the curved portion, wherein the plurality of segmented electrodes comprise one or more sets of segmented electrodes corresponding to the at least one segmented electrode preform, and wherein each set of segmented electrodes includes two or more segmented electrodes secured to a respective insulator portion.

15. The method of claim 14, wherein the outer curved surface of each segmented electrode of the plurality of segmented electrodes has a length and width, and wherein the radius of the curve of a respective segmented electrode is greater than one tenth of the lesser of the length and the width of the respective segmented electrode.

16. The method of claim 15, wherein the radius of the curve is greater than 25% of the lesser of the length and the width of the respective segmented electrode.

17. The method of claim 14, wherein the outer curved surface of each segmented electrode of the plurality of segmented electrodes has a length and a width, and wherein the outer curved surface of a respective segmented electrode has a surface area that is five percent less than a surface area of an outer curved surface of a square perimeter electrode having the length and the width of the respective segmented electrode.

18. The method of claim 17, wherein the surface area of the outer curved surface of the respective segmented electrode is ten percent less than the surface area of the outer curved surface of the square perimeter electrode having the length and the width of the respective segmented electrode.

19. The method of claim 14, wherein the radius of the curve is greater than 0.001 inches.

20. The method of claim 14, wherein the perimeter of the outer curved surface of each segmented electrode of the plurality of segmented electrodes has an oval shape.

* * * * *